(12) United States Patent
Gole et al.

(10) Patent No.: US 9,568,448 B2
(45) Date of Patent: Feb. 14, 2017

(54) GAS SENSORS AND METHODS OF PREPARATION THEREOF

(71) Applicant: Georgia Tech Research Corporation, Atlanta, GA (US)

(72) Inventors: James Gole, Atlanta, GA (US); William Ivey Laminack, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 470 days.

(21) Appl. No.: 14/262,117

(22) Filed: Apr. 25, 2014

(65) Prior Publication Data

US 2014/0311221 A1 Oct. 23, 2014

Related U.S. Application Data

(63) Continuation of application No. 14/240,691, filed as application No. PCT/US2012/051721 on Aug. 21, 2012.

(60) Provisional application No. 61/527,294, filed on Aug. 25, 2011, provisional application No. 61/820,237, filed on May 7, 2013.

(51) Int. Cl.
*G01N 27/403* (2006.01)
*G01N 27/12* (2006.01)

(52) U.S. Cl.
CPC .......... *G01N 27/128* (2013.01); *G01N 27/127* (2013.01)

(58) Field of Classification Search
CPC .... G01N 27/414; G01N 27/403; G01N 27/02; B82Y 15/00
See application file for complete search history.

(56) References Cited

U.S. PATENT DOCUMENTS

| | | | |
|---|---|---|---|
| 4,542,640 A | 9/1985 | Clifford | |
| 5,726,463 A * | 3/1998 | Brown | H01L 29/1608 257/288 |
| 6,165,336 A * | 12/2000 | Maki | G01N 27/4074 204/415 |
| 7,452,126 B2 | 11/2008 | Arndt | |
| 7,459,732 B2 * | 12/2008 | Fleischer | G01N 27/002 257/213 |
| 7,598,584 B2 * | 10/2009 | Ohta | H01L 31/103 257/184 |
| 7,933,535 B2 | 4/2011 | Deguchi | |
| 8,399,883 B2 * | 3/2013 | Park | G01N 27/4074 204/424 |
| 2005/0193800 A1 * | 9/2005 | DeBoer | G01N 27/128 73/1.06 |
| 2007/0140908 A1 | 6/2007 | Mizuguchi | |
| 2008/0110241 A1 | 5/2008 | Rothschild | |
| 2010/0147684 A1 | 6/2010 | Park | |
| 2010/0154517 A1 | 6/2010 | Sammoura | |

OTHER PUBLICATIONS

International Search Report & Written Opinion—Nov. 16, 2012.

* cited by examiner

*Primary Examiner* — Francis Gray
(74) *Attorney, Agent, or Firm* — Thomas | Horstemeyer, LLP

(57) ABSTRACT

Embodiments of the present disclosure include sensors, arrays of conductometric sensors, devices including conductometric sensors, methods of making conductometric sensors, methods of using conductometric gas sensors, methods of enhancing sensor response with light, and the like.

23 Claims, 25 Drawing Sheets

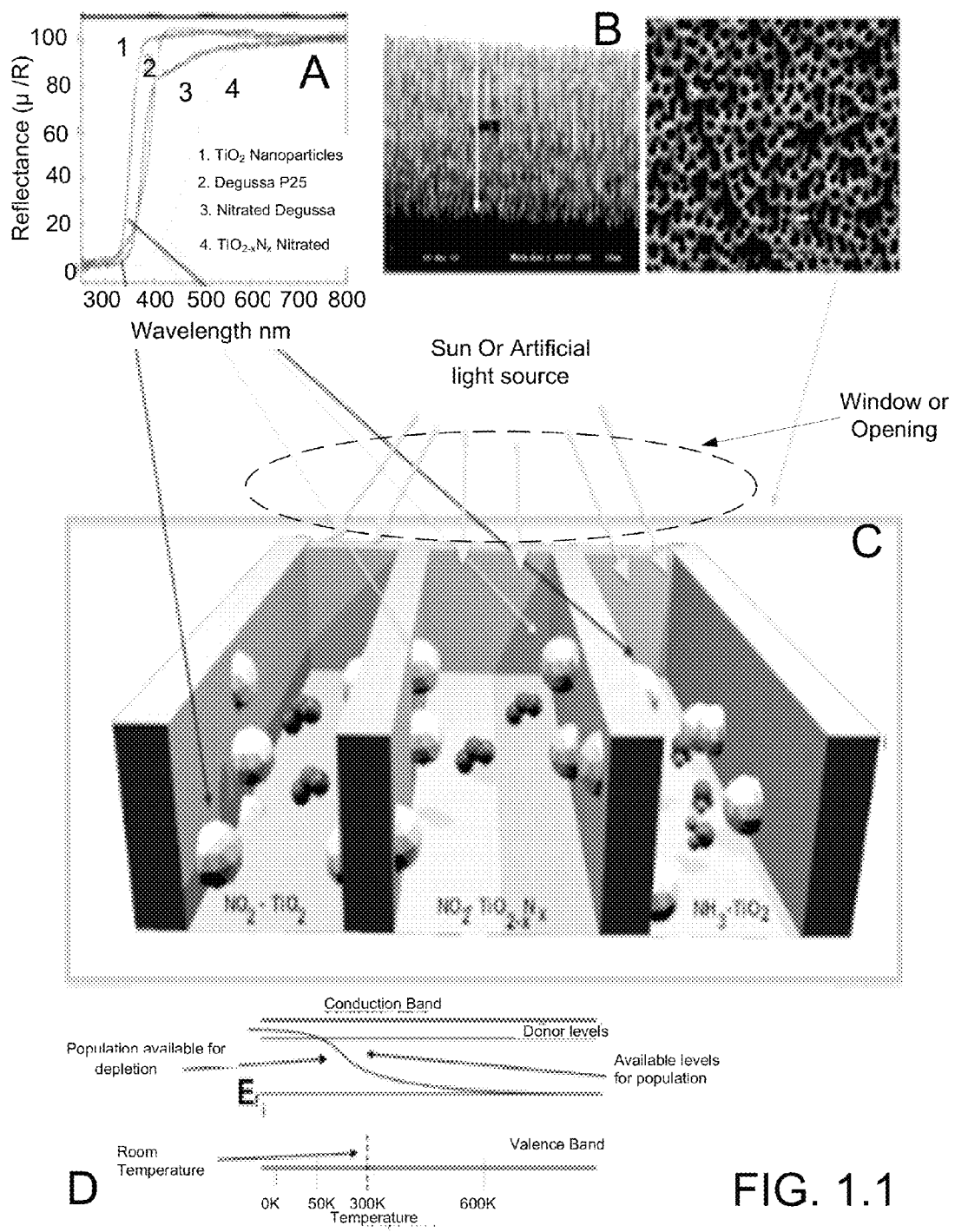
FIG. 1.1

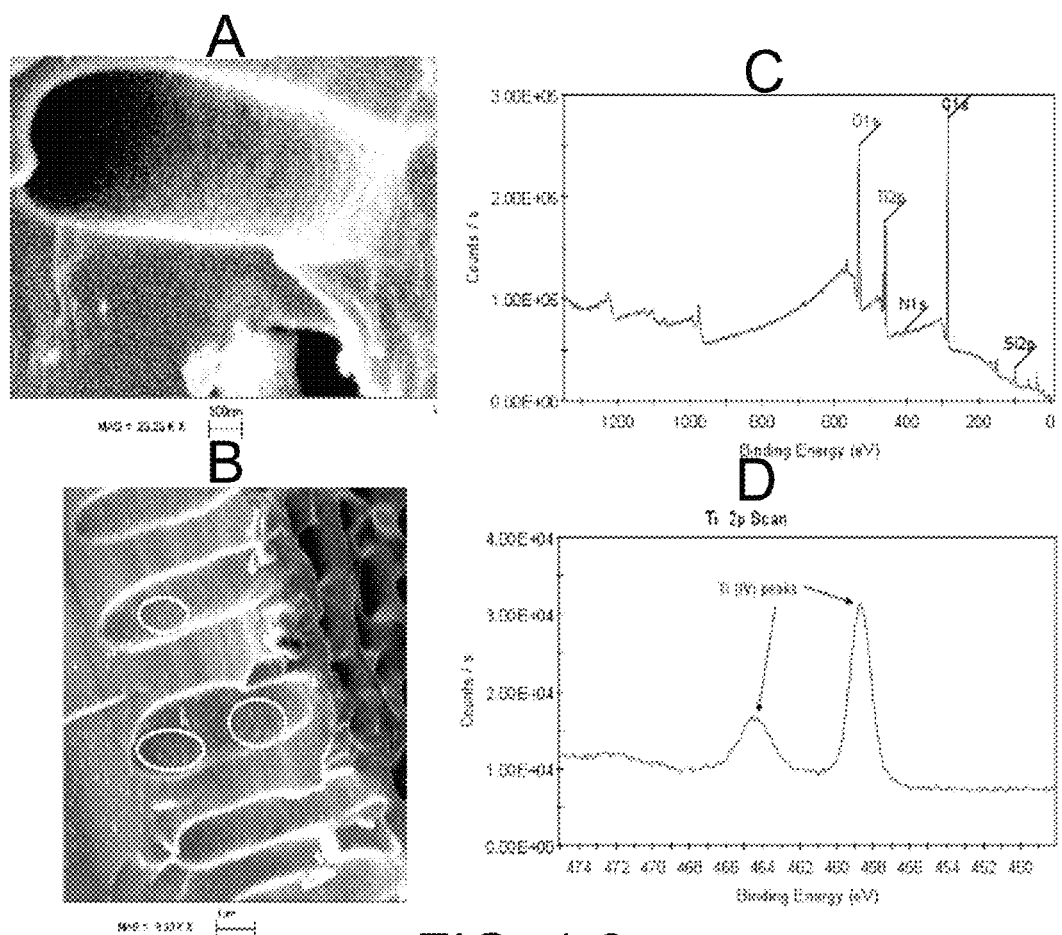
FIG. 1.2
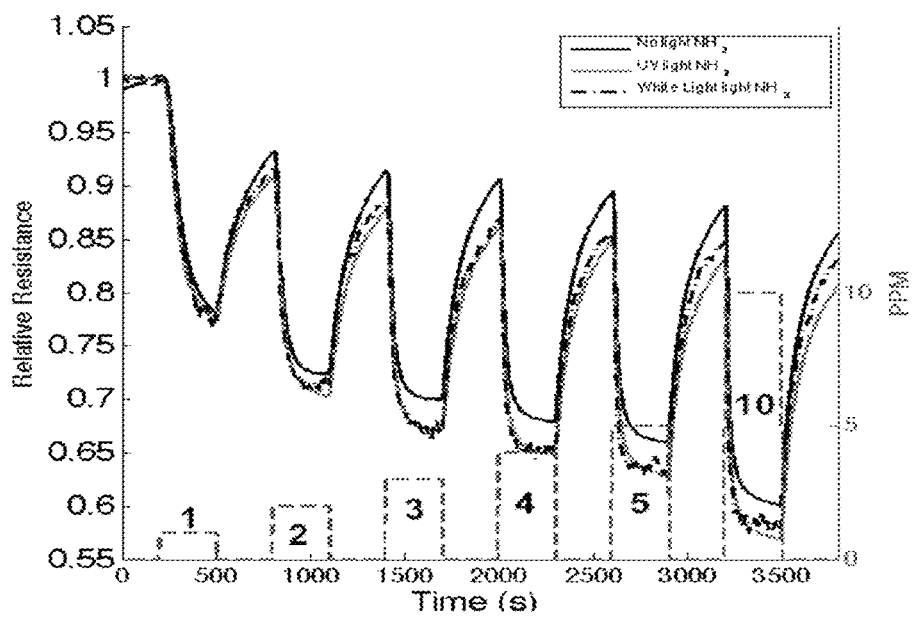
FIG. 1.3

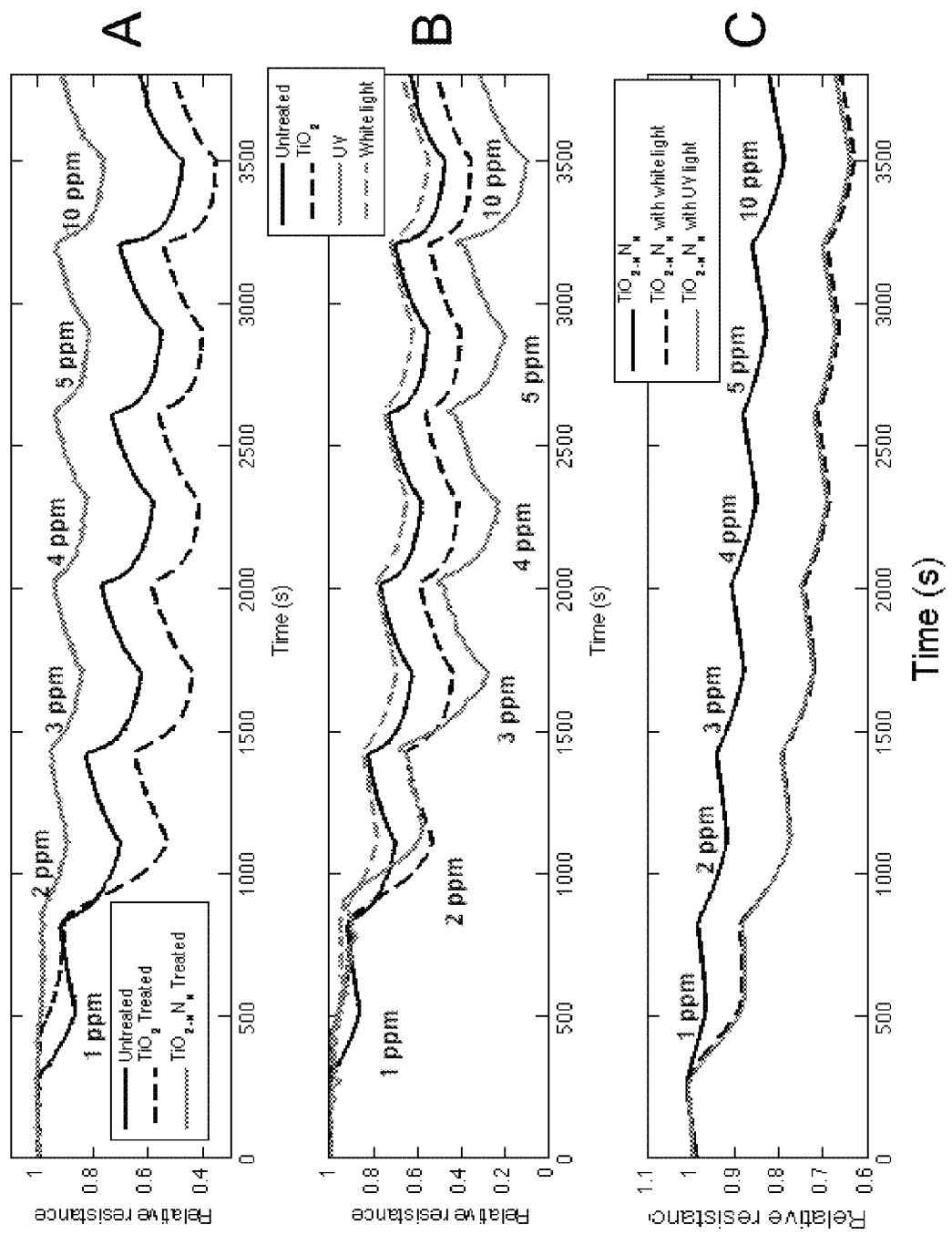
FIG. 1.4

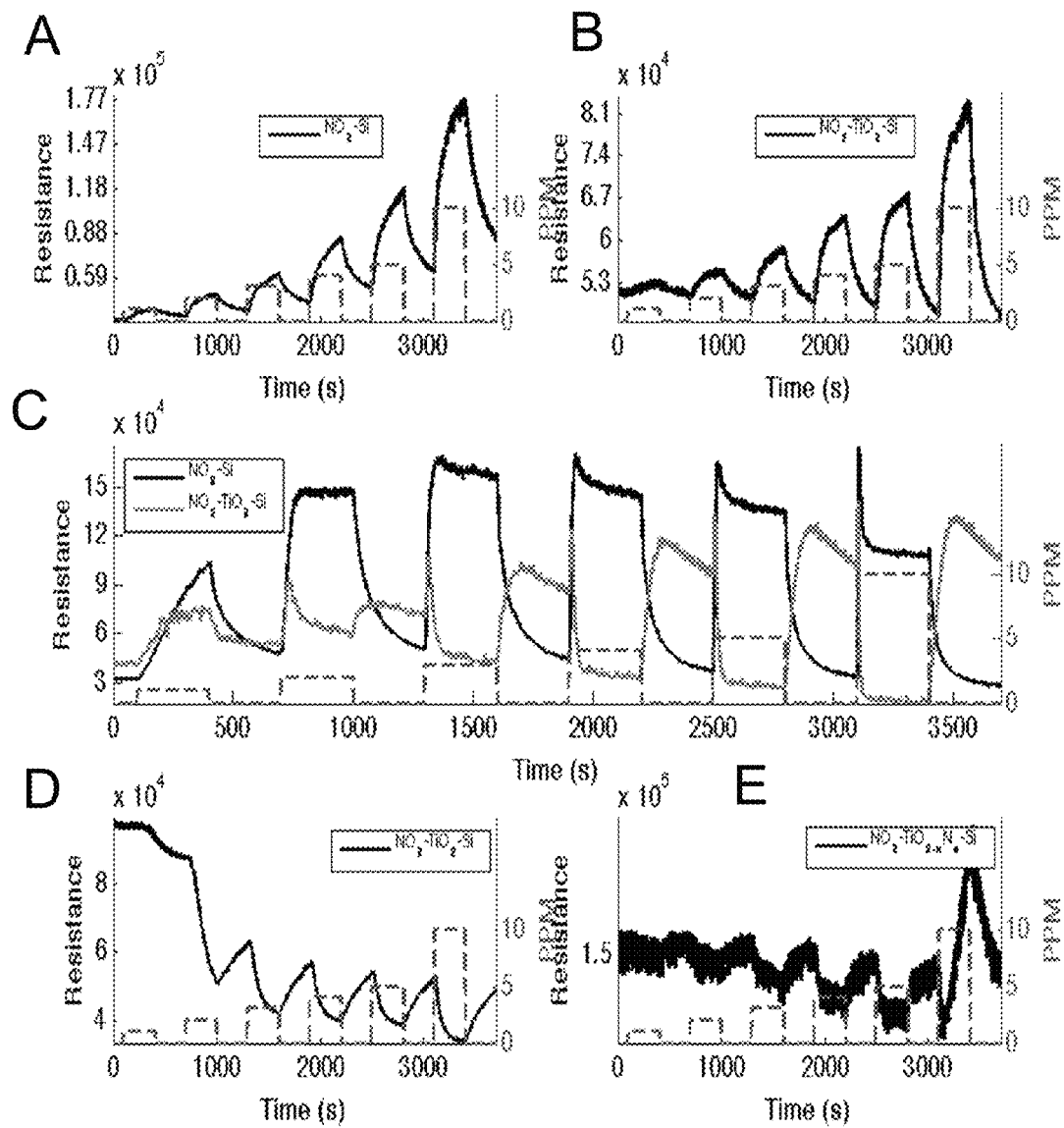
FIG. 1.5

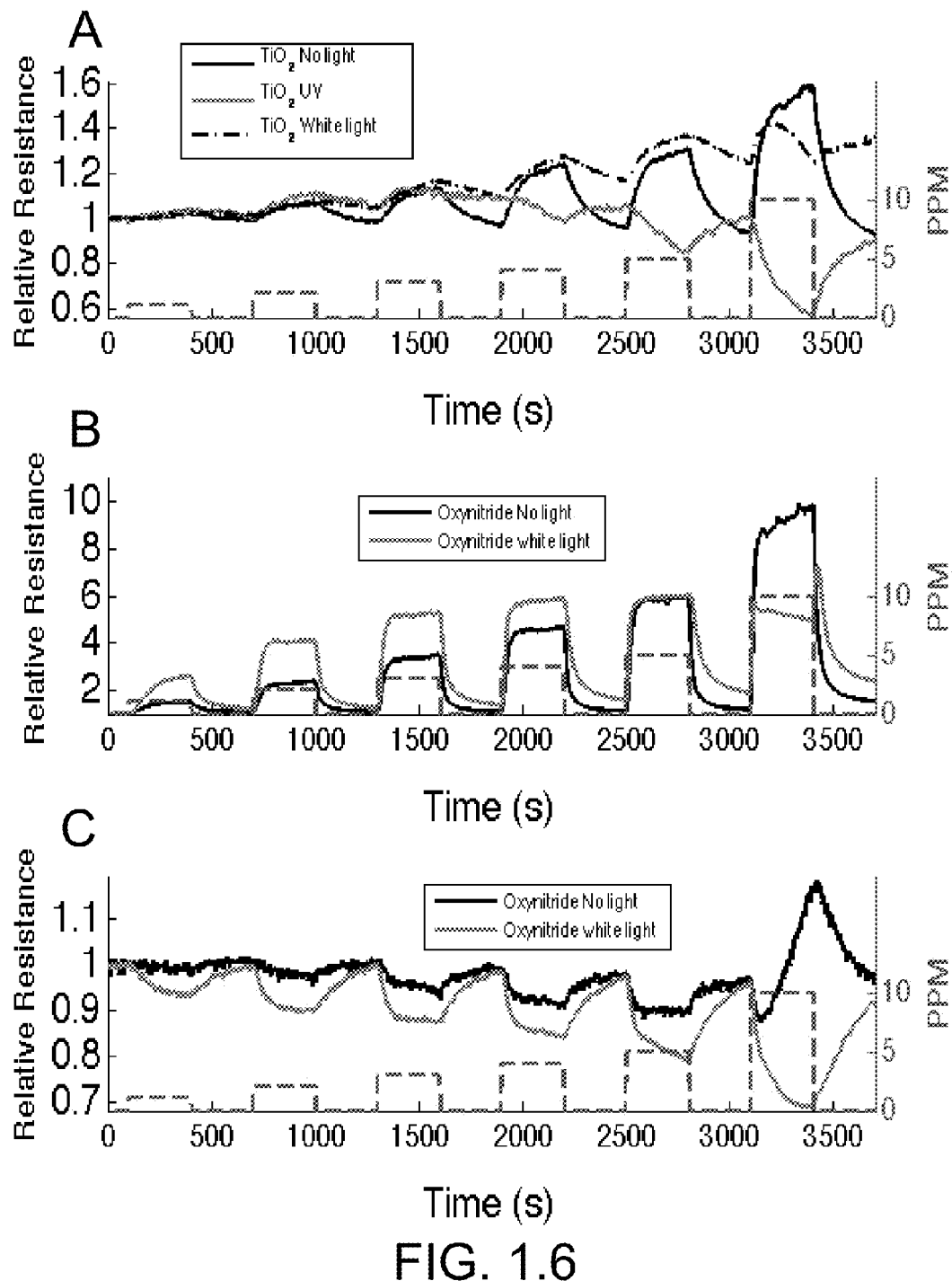
FIG. 1.6

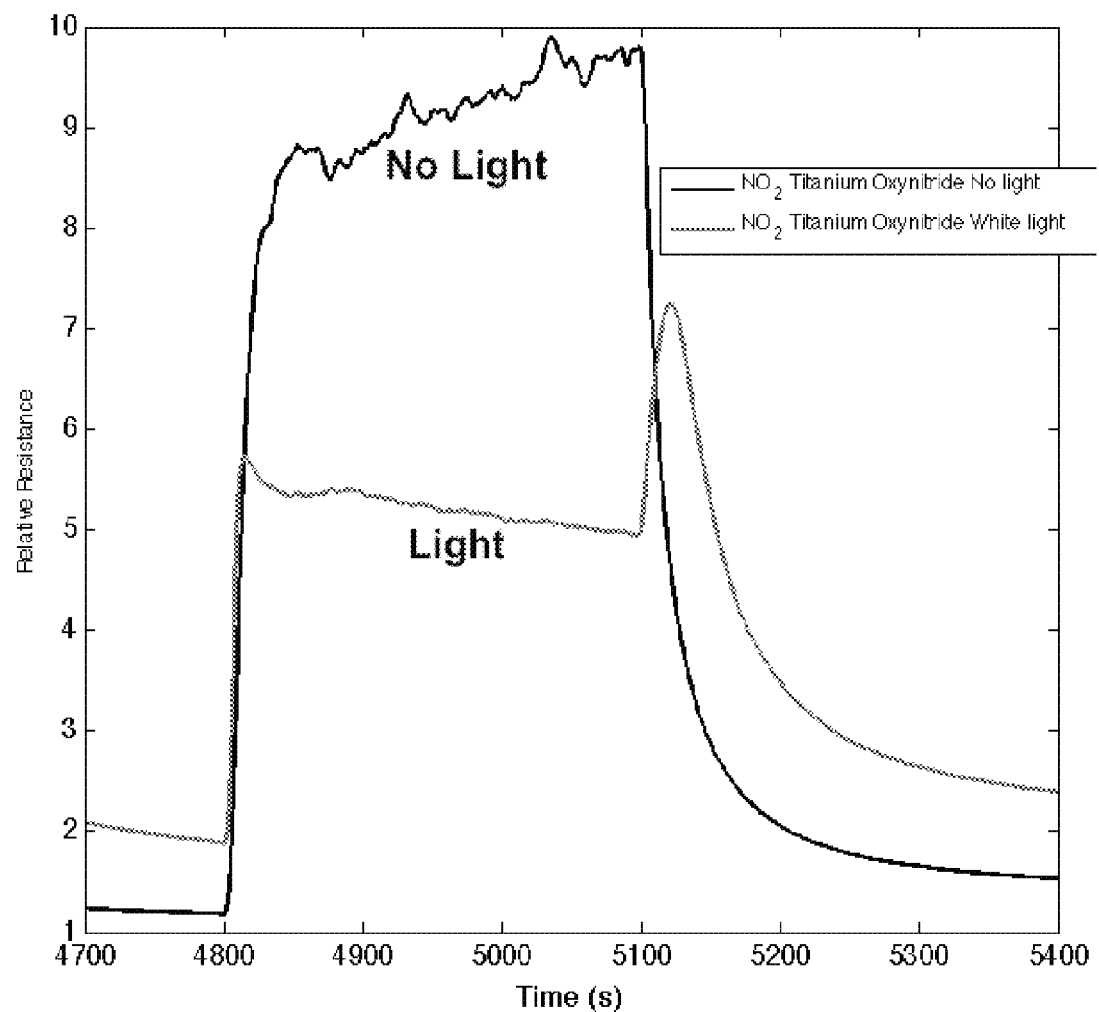
FIG. 1.7

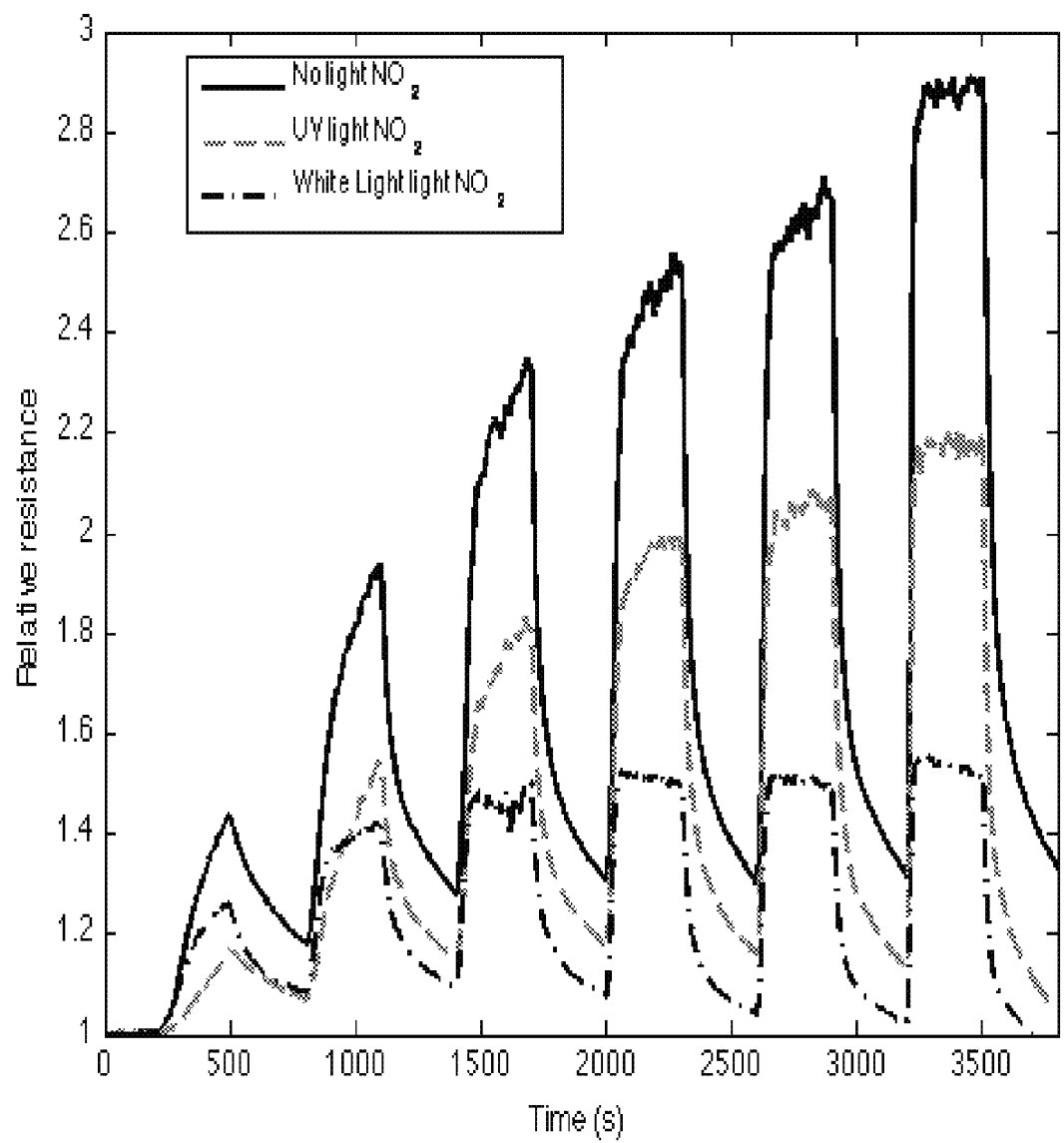
FIG. 1.8

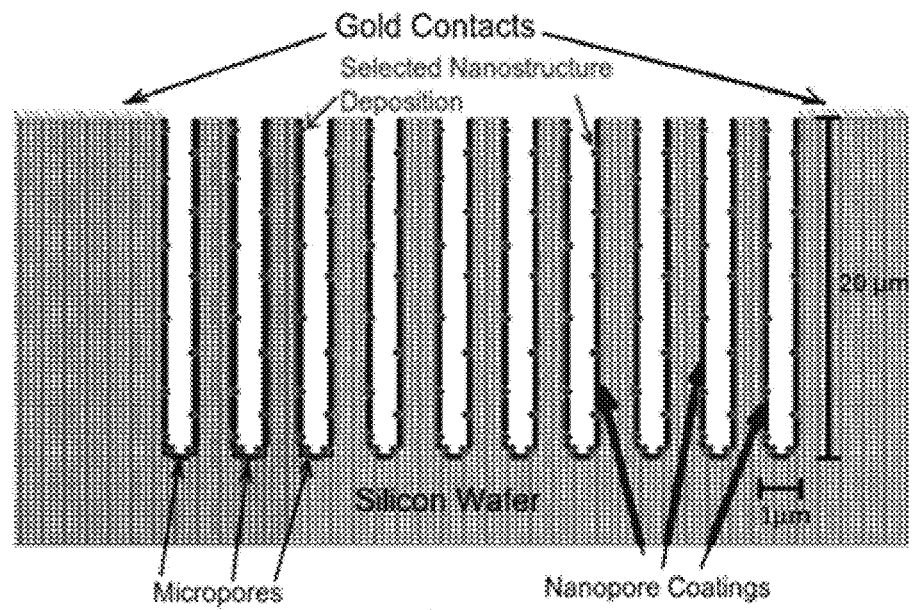
FIG. 2.1
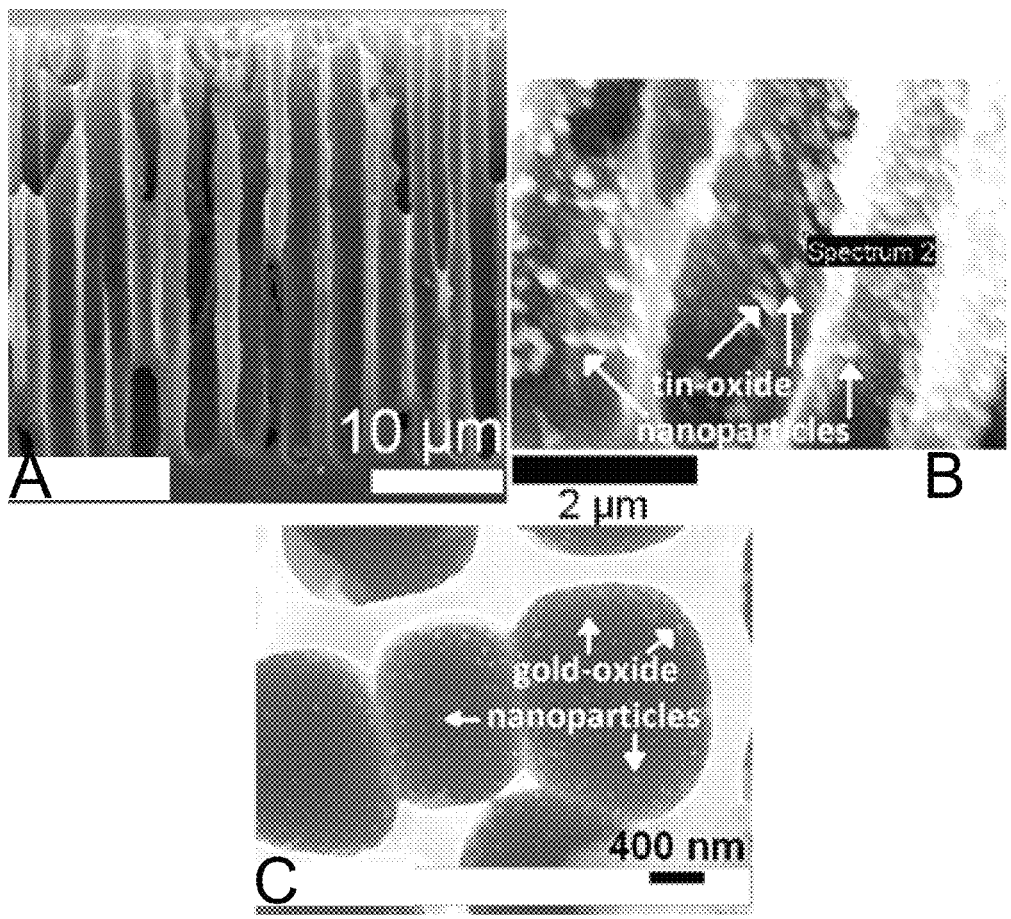
FIG. 2.2

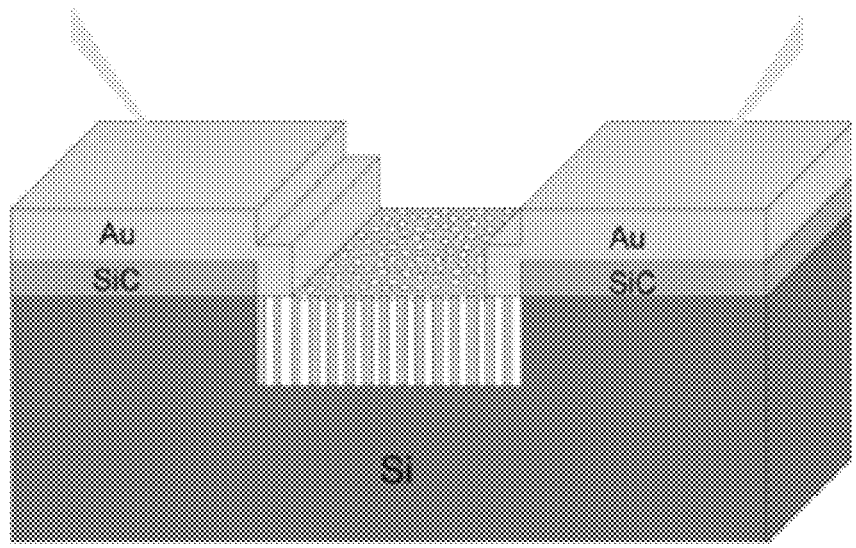
FIG. 2.3
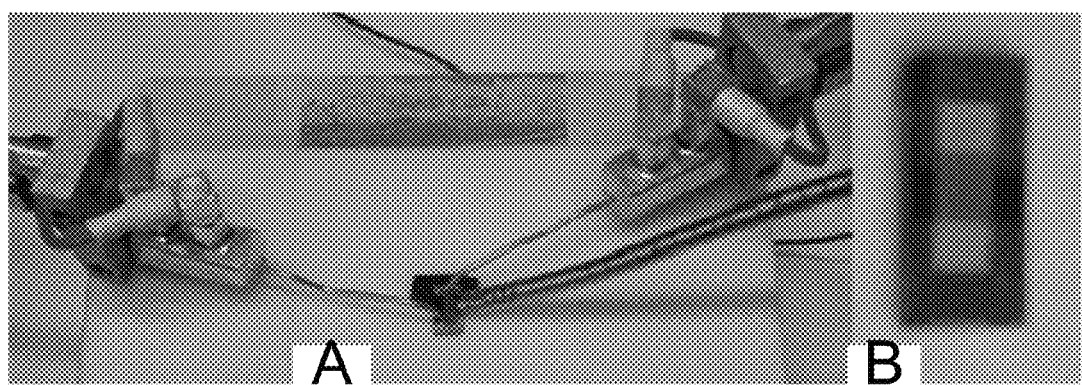
FIG. 2.4

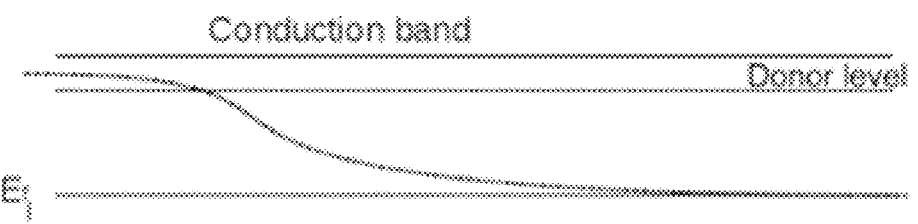
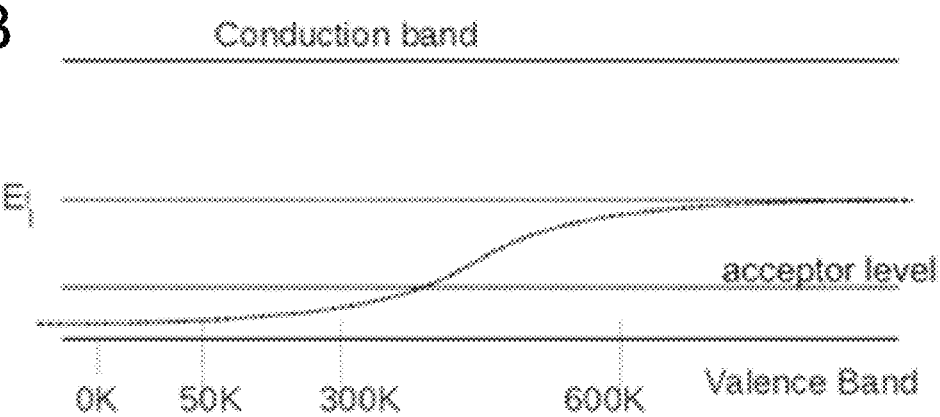
FIG. 2.5

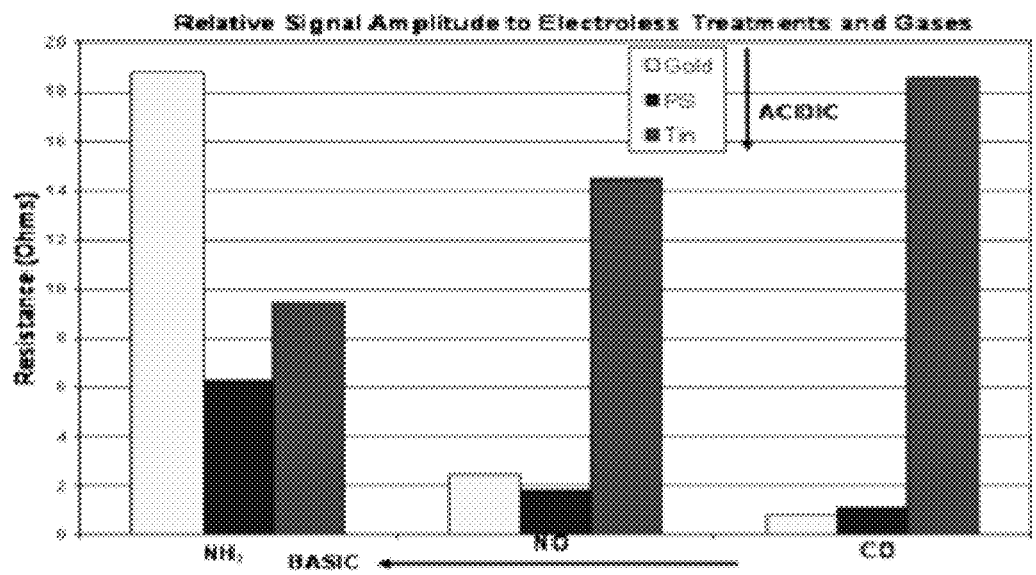
FIG. 2.6
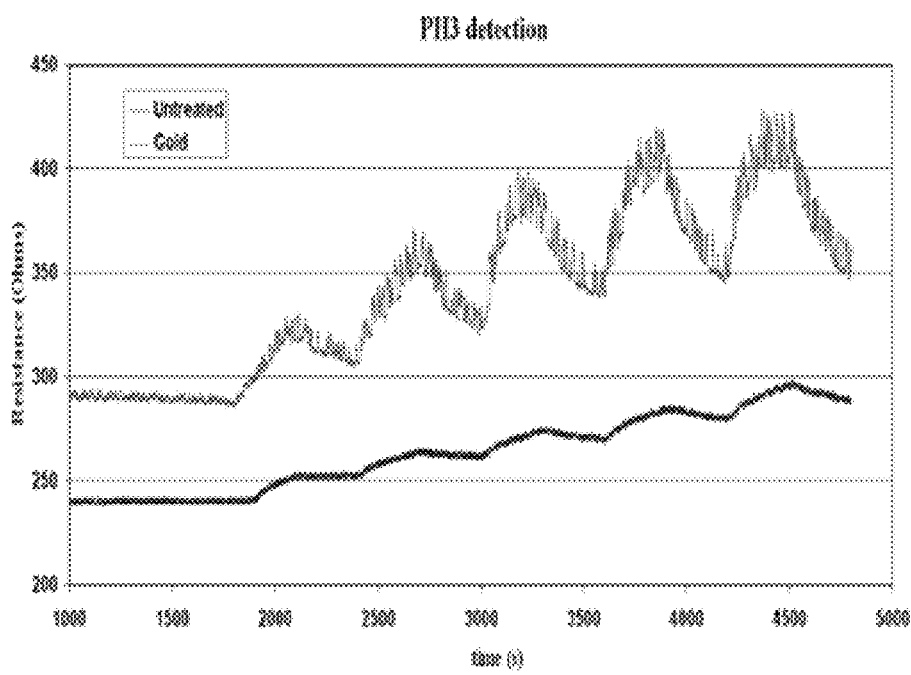
FIG. 2.7

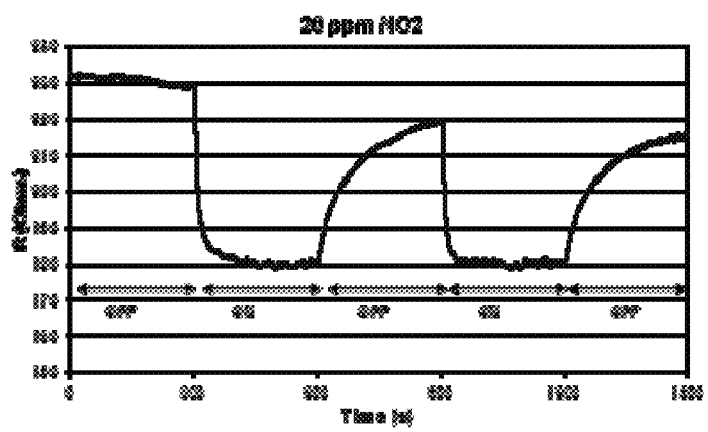
FIG. 2.8
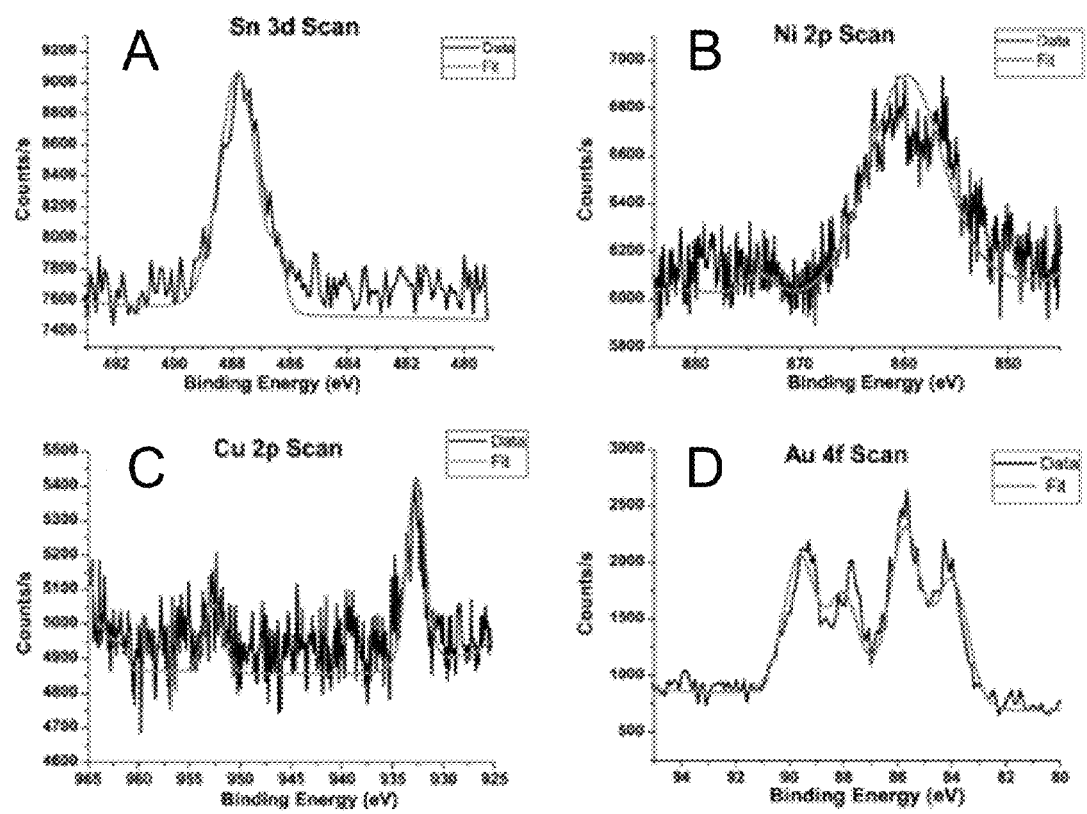
FIG. 2.9

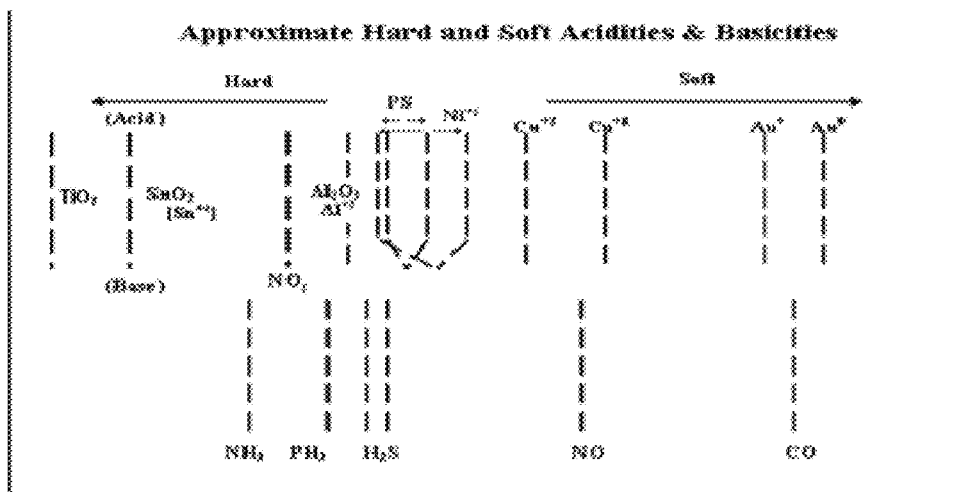
FIG. 2.10
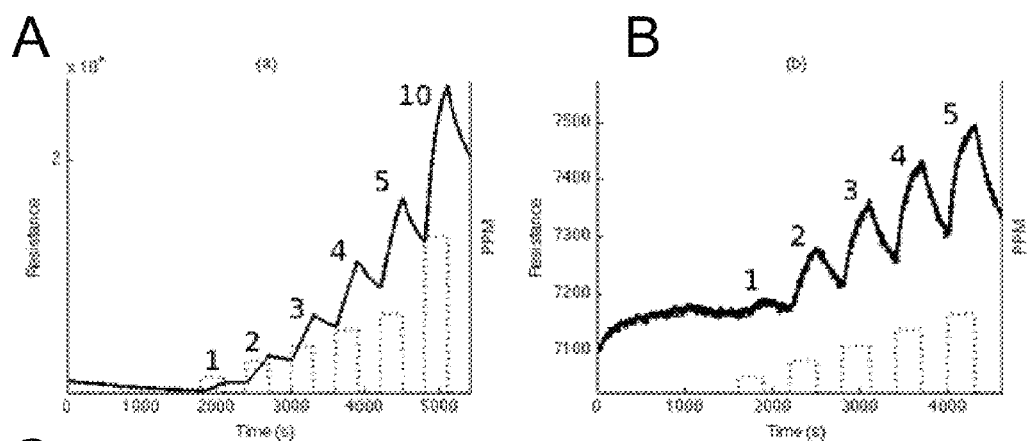
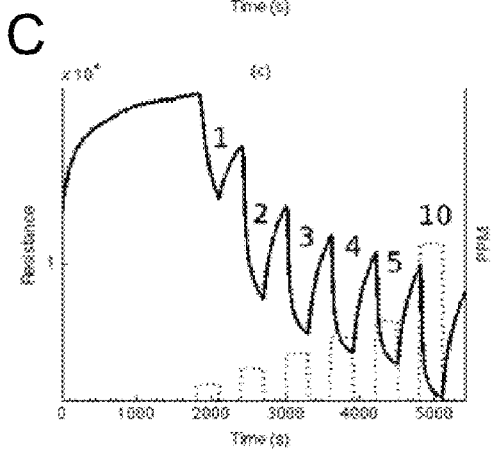
FIG. 2.11

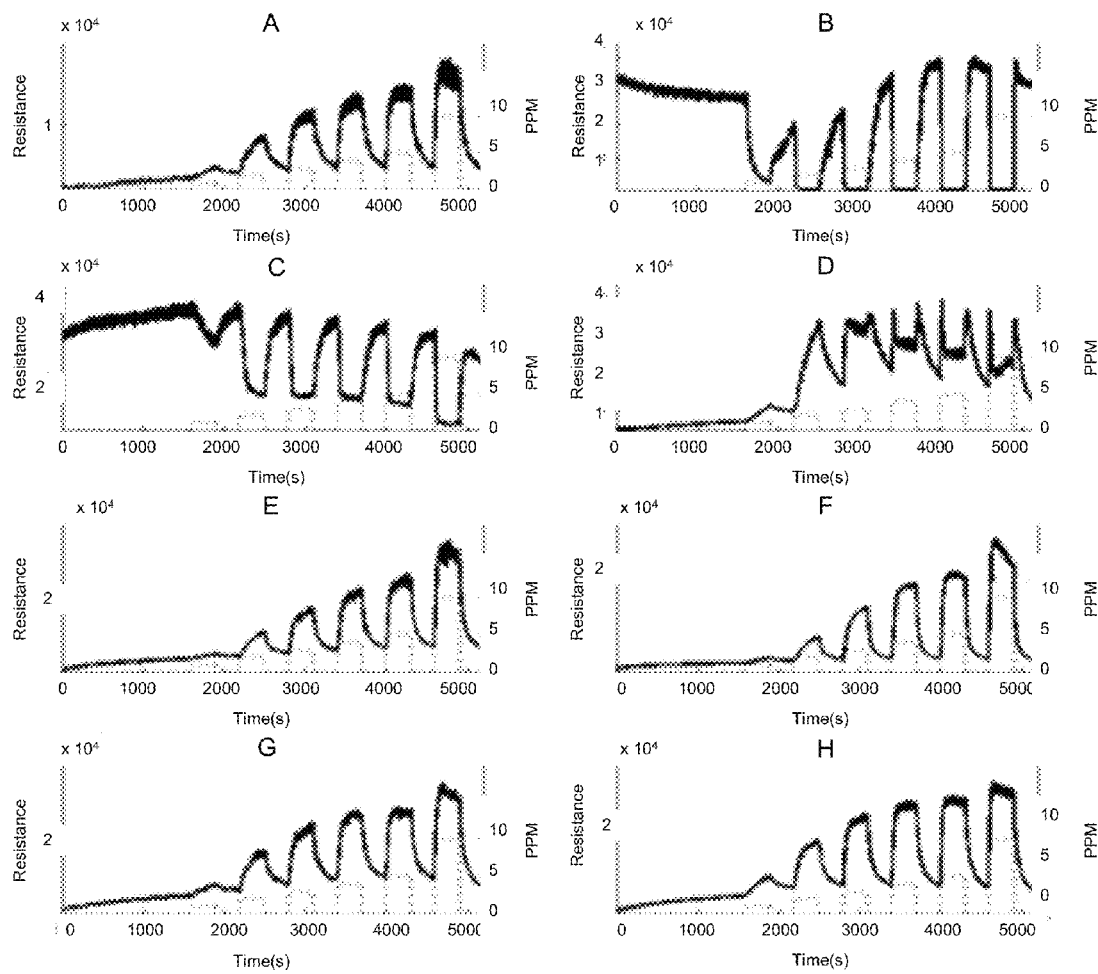
FIG. 2.12

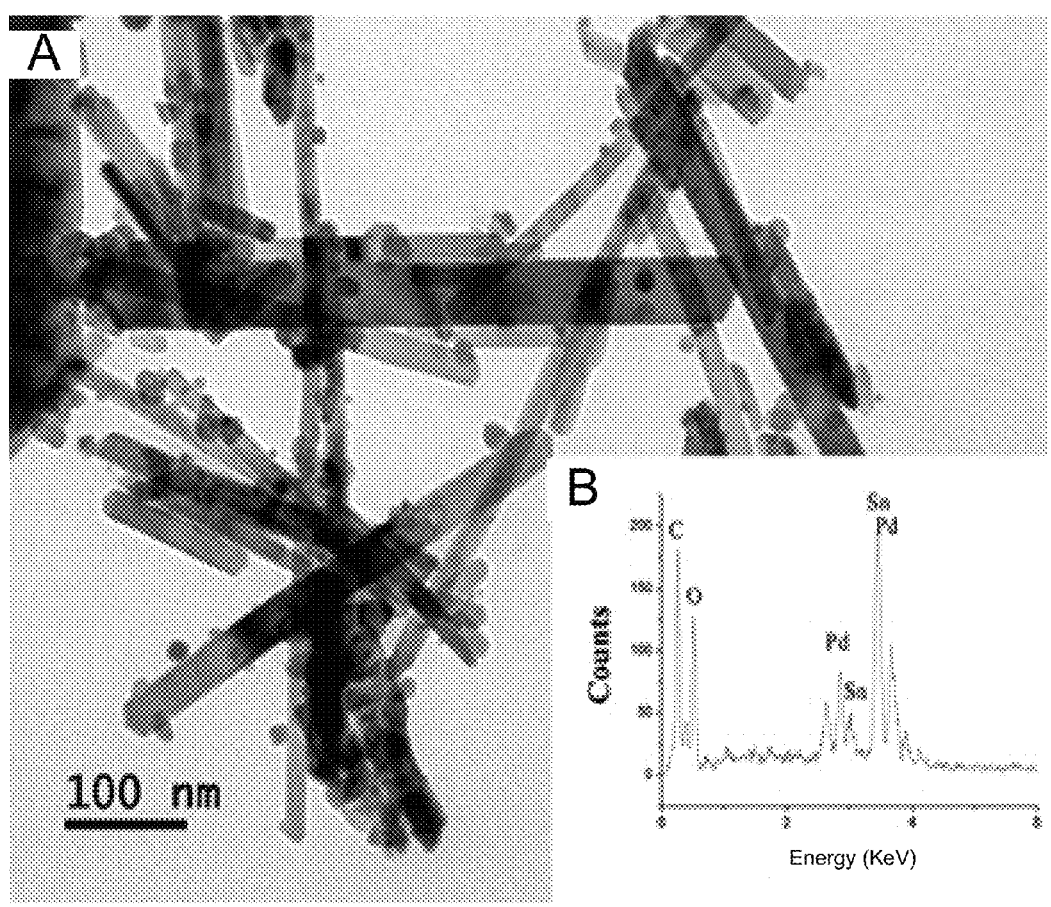
FIG. 2.13

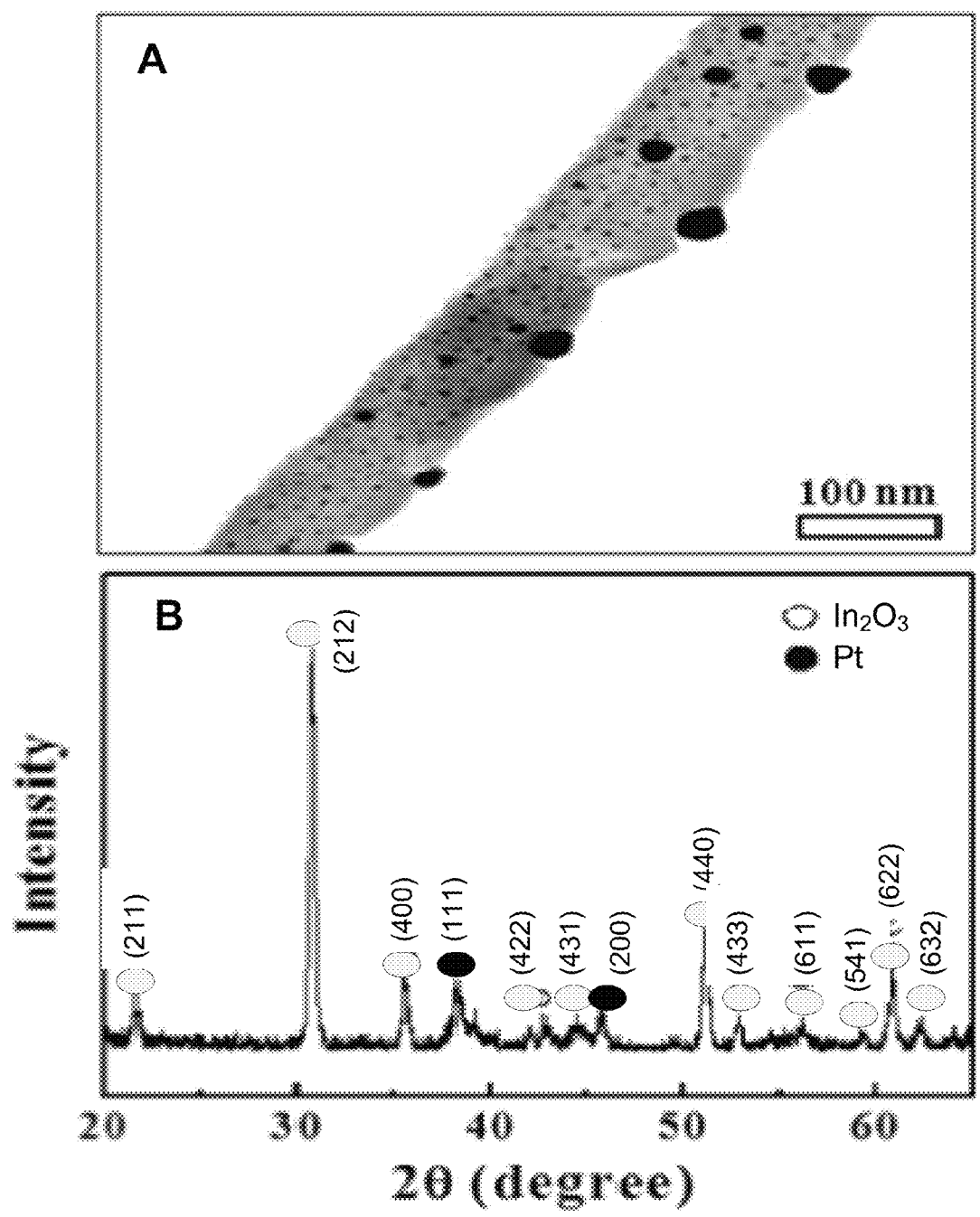
FIG. 2.14

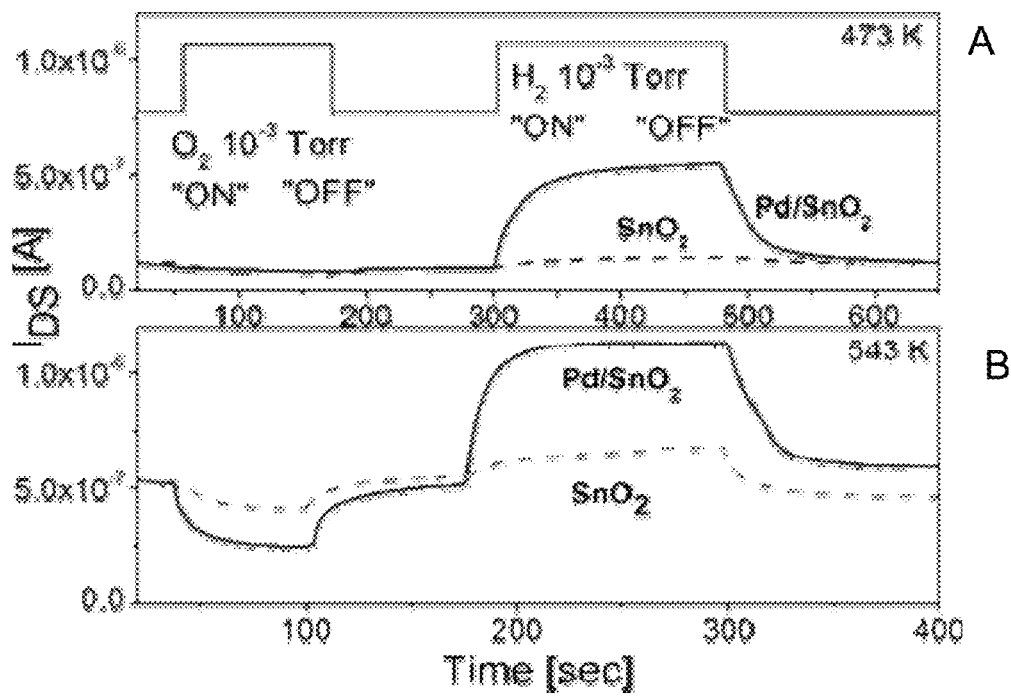
FIG. 2.15
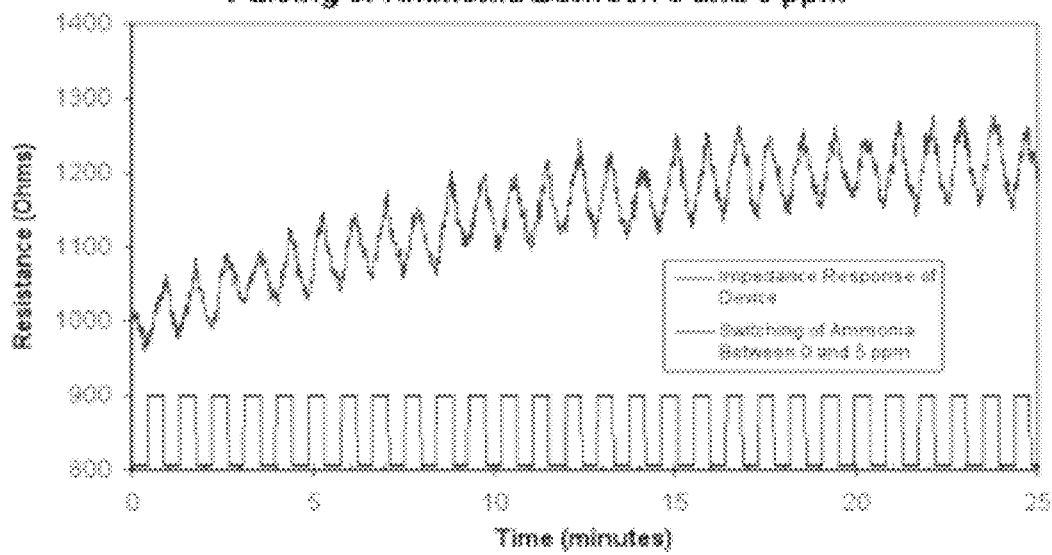
FIG. 2.16

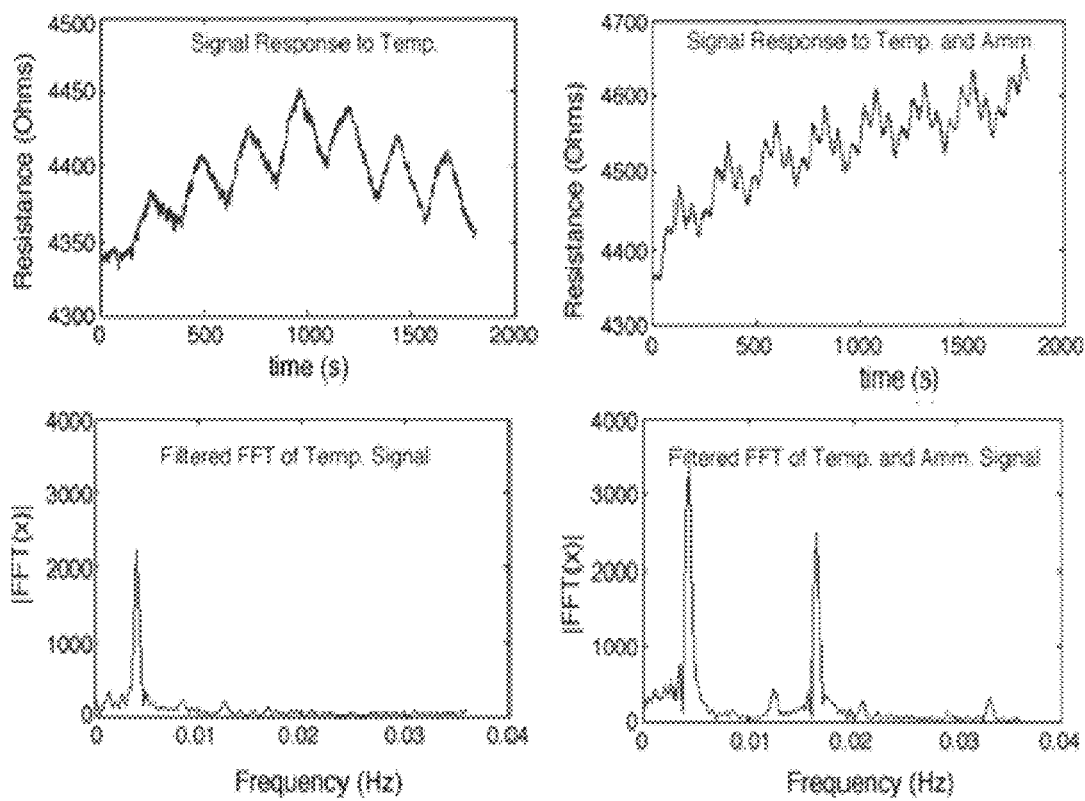
FIG. 2.17

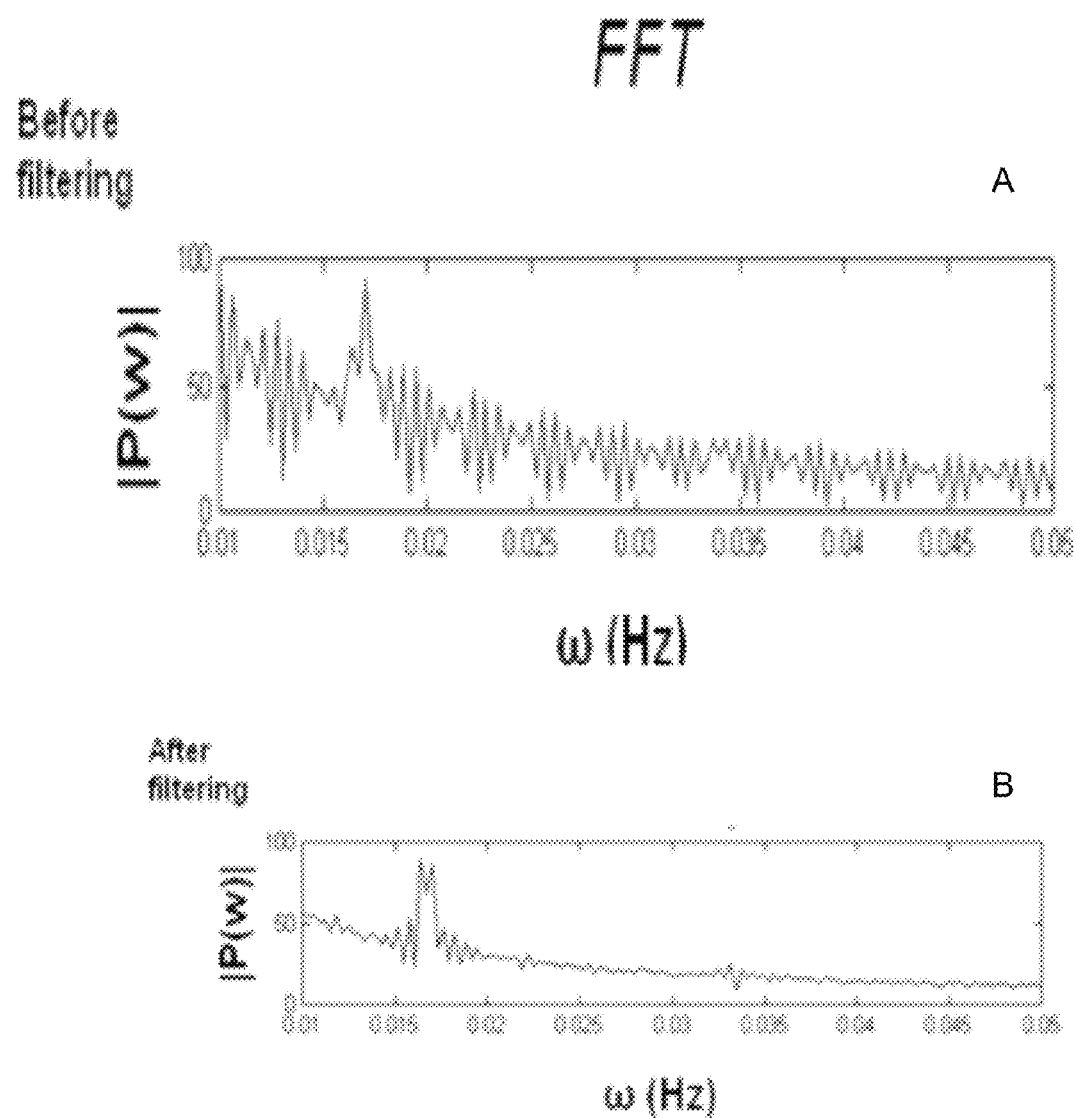
FIG. 2.18

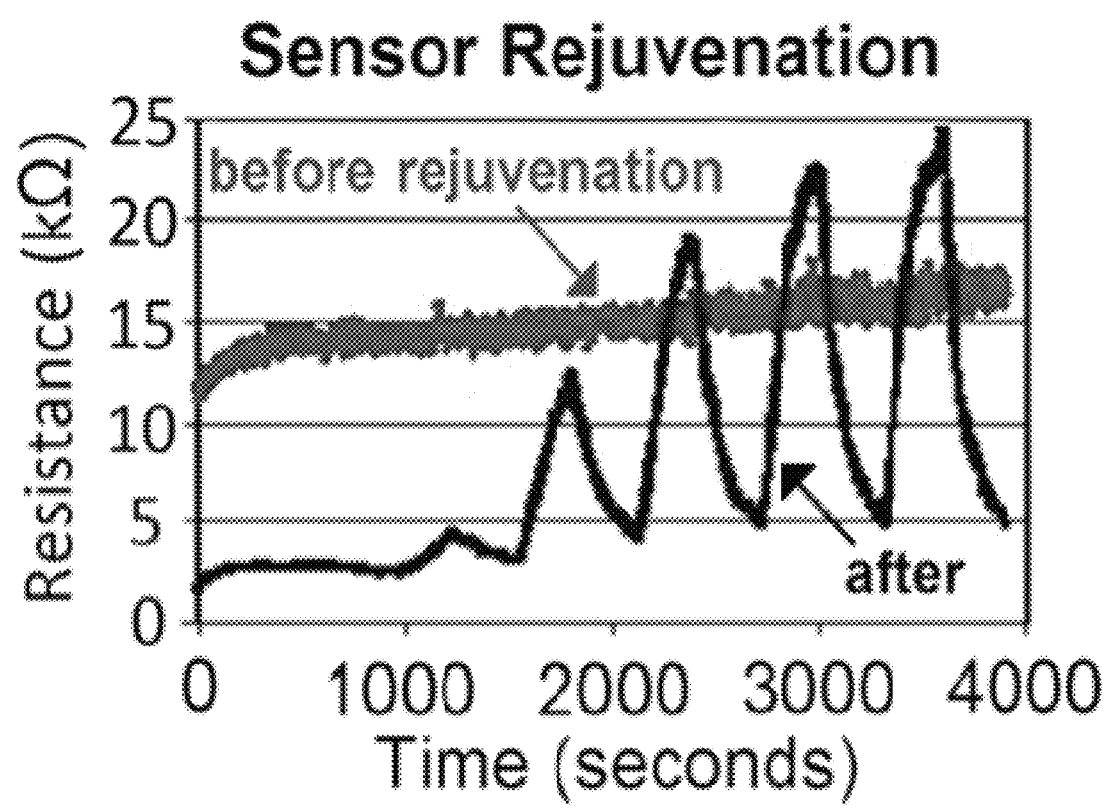
FIG. 2.19

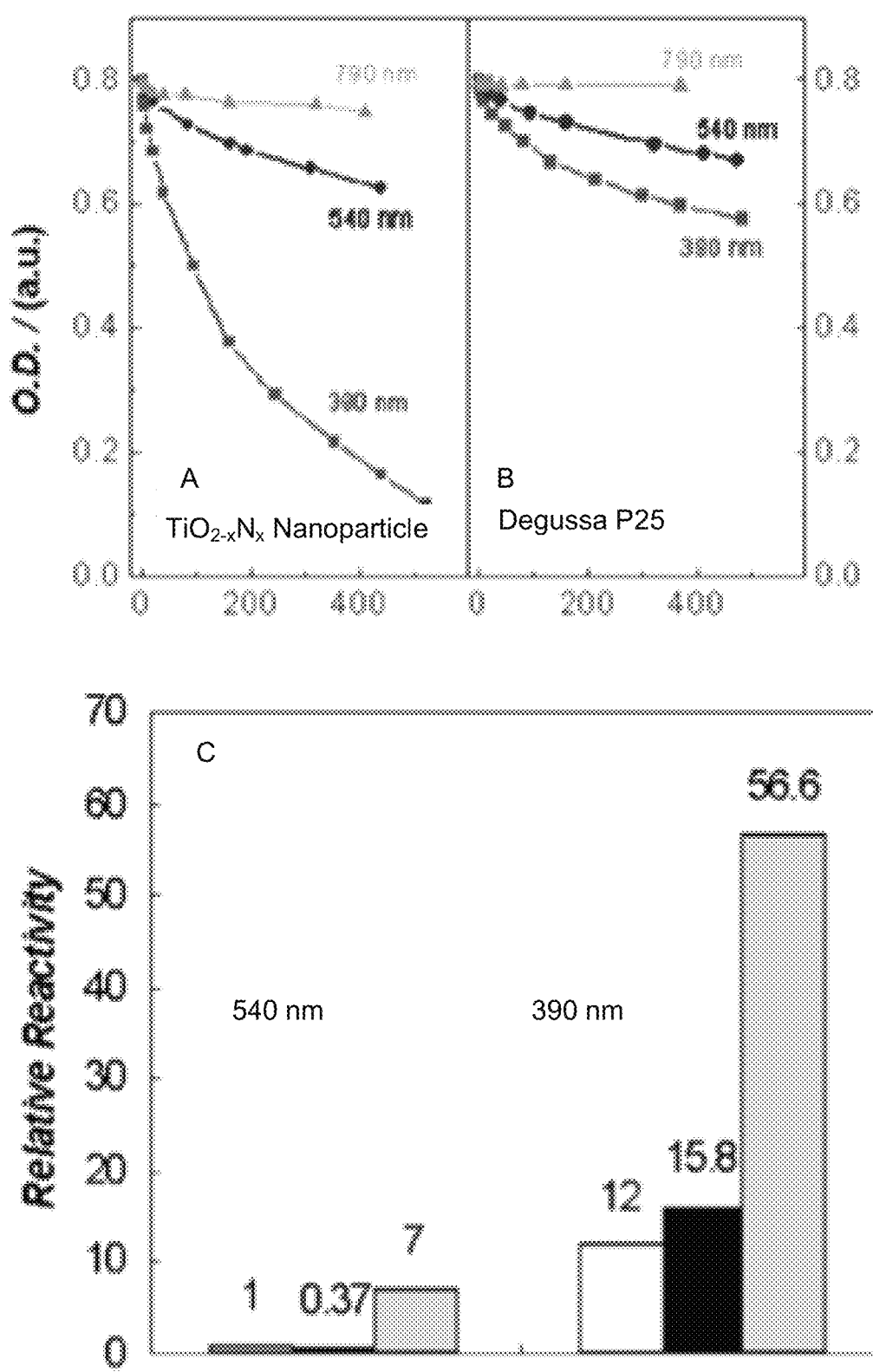
FIG. 2.20

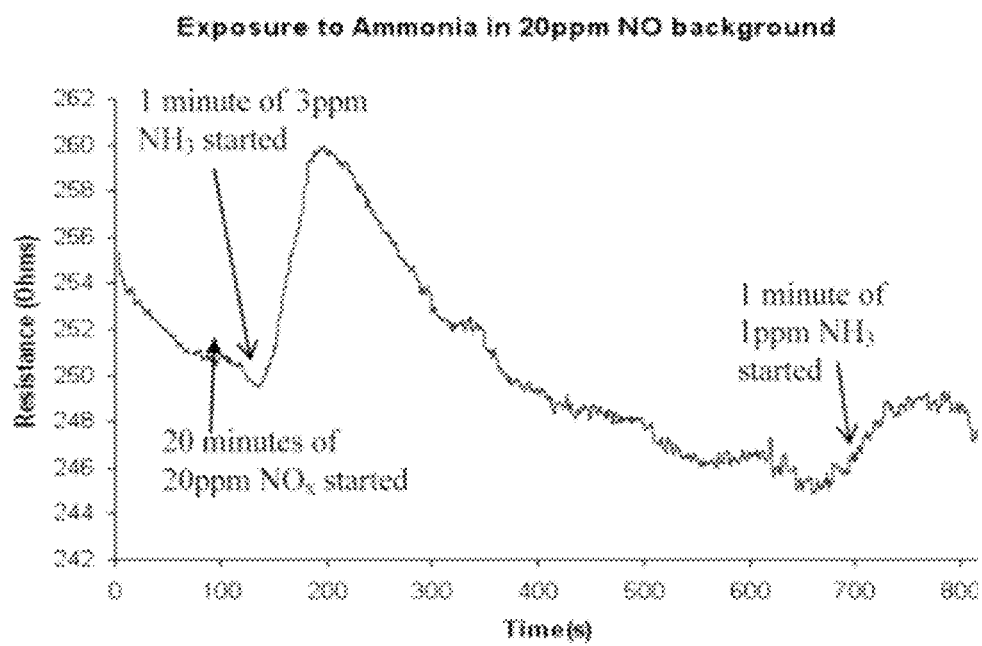
FIG. 2.21
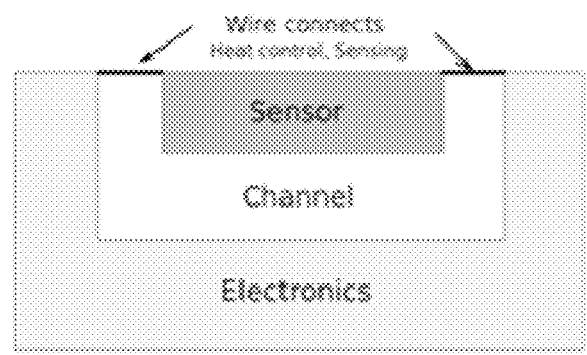
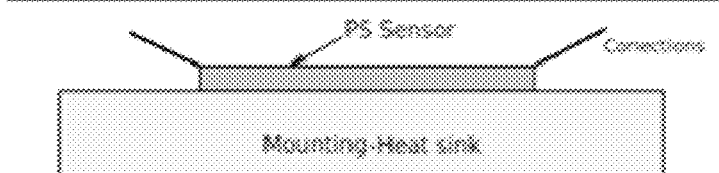
FIG. 2.22

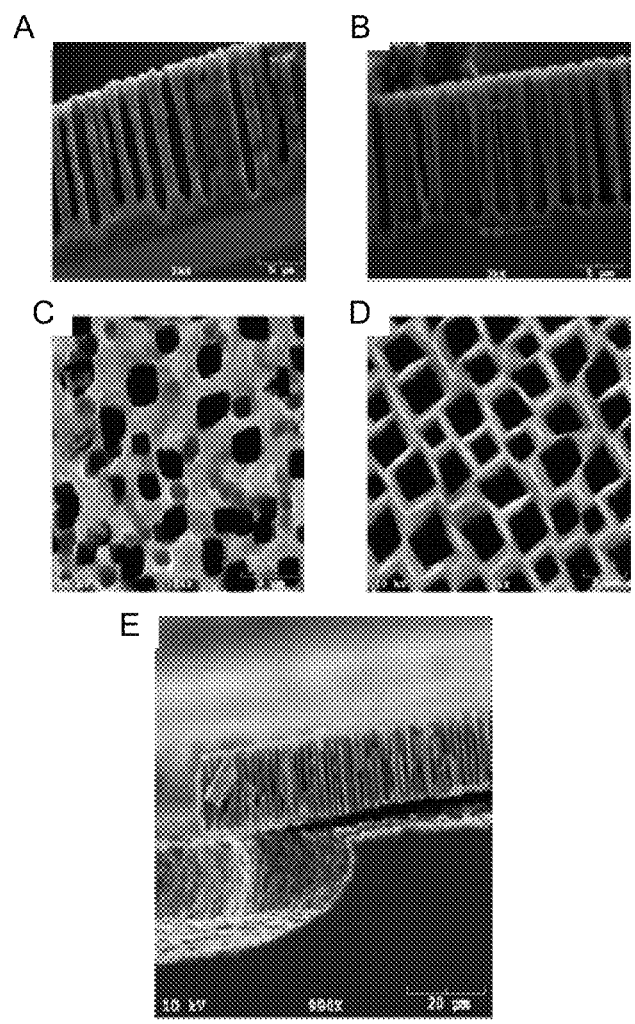
FIG. 2.23

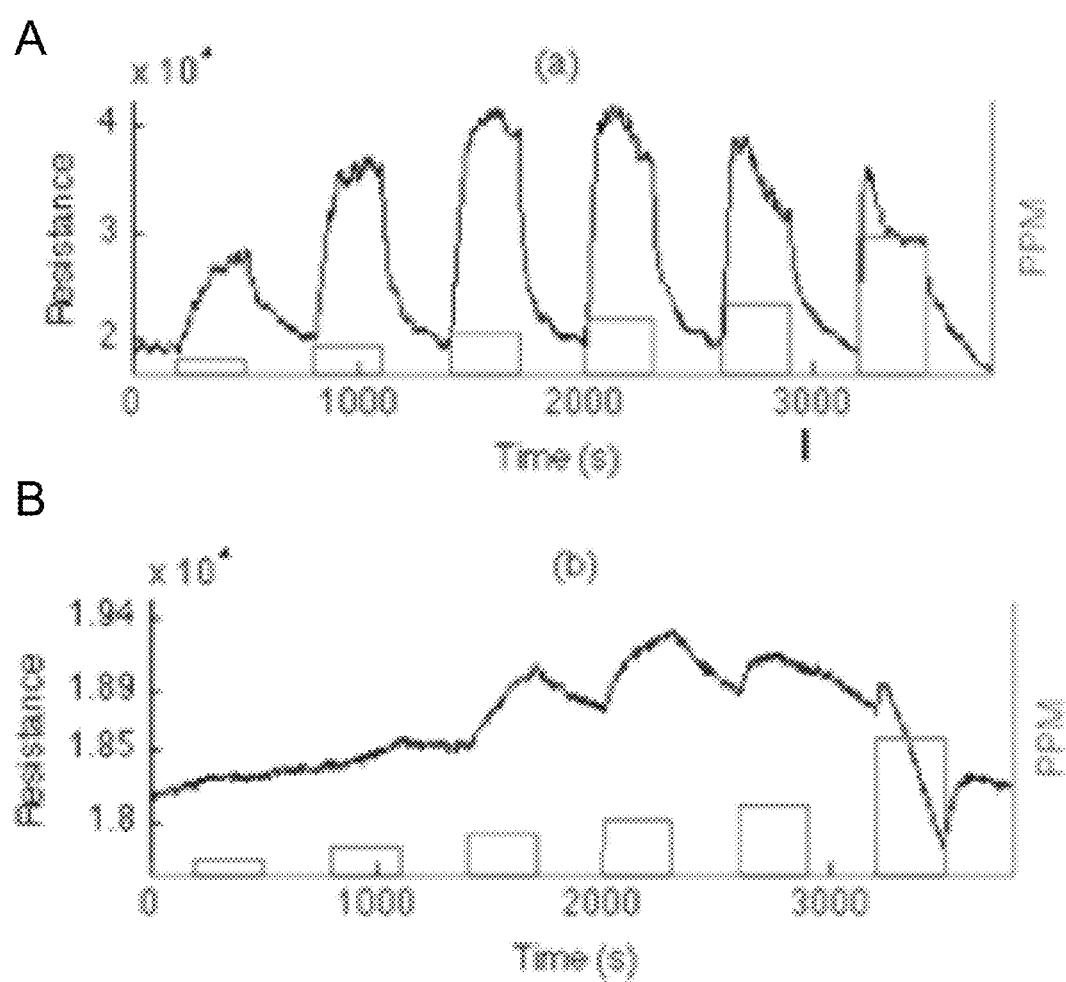
FIG. 2.24

A

| Hard | Borderline | Soft |
|---|---|---|
| Acids $H^+$, $Li^+$, $Na^+$, $K^+$ $Ag^-$, $Tl^+$, $Hg^+$ | $Fe^{2+}$, $Co^{2+}$, $Ni^{2+}$ | $Cu^+$, $Au^+$ |
| $Be^{2+}$, $Mg^{2+}$, $Ca^{2+}$ $Pt^{2+}$, $Hg^{2+}$ | $Cu^{2+}$, $Zn^{2+}$, $Pb^{2+}$ $Cd^{2+}$ | $Pd^{2+}$ |
| $Cr^{2+}$, $Cr^{3+}$, $Al^{3+}$ $SO_3$, $BF_3$, $Sn^{+4}$, $Ti^{+4}$ | $BBr_3$, $Sn^{+2}$, $NO_2$ | $BH_3$, $NO$ |
| Bases $F^-$, $OH^-$, $H_2O$, $NH_3$ $CO$, $I$ | $NO_2$, $SO_3^{2-}$, $Br^-$ | $H^-$, $R^-$, $CN^-$ |
| $CO_3^{2-}$, $NO_3^-$, $O^{2-}$ $C_6H_5$ | $N_3^-$, $N_2$, $H_2S$, $SO_2$ $R_3P$ | $SCN^-$ |
| $SO_4^{2-}$, $PO_4^{3-}$, $ClO_4^-$ | $C_6H_5N$, $SCN$ | $R_2S$, $NO$ |

B

|  | $SnO_2$ | NiO | $Cu_xO$ | $Au_xO$ |
|---|---|---|---|---|
| $PH_3$ | 2 | 2.5 | 4 | 5 |
| NO | 7-10 | 3.5 | 1 | 1.5-2 |
| $NH_3$ | 1.5 | 1.5-2 | 2-2.5 | ~3 |
| $SO_2$ | 4 | (2) | 1+ | 2 |

C

|  | $TiO_2$ | $SnO_2$ | NiO | $Cu_xO$ | $Au_xO$ |
|---|---|---|---|---|---|
| NO | -12* | -2* | 4 | 1.2 | 1.5-2 |
| $NO_2$ | 0.75 | 0.5** | (0.9-1) | 1 | 1.5-2** |
| $NH_3$* | (3.5-4) | 2.5 | 1.5 | 2 | 3 |

FIG. 2.25

GAS SENSORS AND METHODS OF PREPARATION THEREOF

CROSS-REFERENCE TO RELATED APPLICATION

This application is a continuation-in-part application of application entitled "GAS SENSORS AND METHODS OF PREPARATION THEREOF" having Ser. No. 14/240,691, filed on Feb. 24, 2014, which is a 35 U.S.C. §371 national stage of PCT Application No. PCT/US2012/051721, entitled "GAS SENSORS AND METHODS OF PREPARATION THEREOF" and filed Aug. 21, 2012, which claims priority to U.S. Provisional Application entitled "NANOSTRUCTURE DRIVEN ANALYTE-INTERFACE ELECTRON TRANSDUCTION" having Ser. No. 61/527,294, filed on Aug. 25, 2011, each of which is incorporated herein by reference.

In addition, this application claims priority to U.S. Provisional Application entitled "SOLAR PUMPING SENSING" having Ser. No. 61/820,237, filed on May 7, 2013, which is incorporated herein by reference.

BACKGROUND

Porous silicon (PS) has drawn considerable attention for sensor applications. Its luminescence properties, large surface area, and compatibility with silicon based technologies have been the driving force for this technology development. However, there exists a need in the industry to advance sensor technologies.

SUMMARY

Embodiments of the present disclosure include sensors, arrays of conductometric sensors, devices including conductometric sensors, methods of making conductometric sensors, methods of using conductometric gas sensors, methods of enhancing sensor response with light, and the like.

One exemplary embodiment of a device, among others, includes: a conductometric porous silicon gas sensor including a n-type silicon substrate having a porous silicon layer, wherein a plurality of nanostructures are disposed on a portion of the porous silicon layer to provide a fractional coverage on the porous silicon layer, wherein the sensor is configured to allow light to illuminate the porous silicon layer, wherein the conductometric porous silicon gas sensor is operative to transduce the presence of a gas into an impedance change when exposed to light, wherein the impedance change correlates to the gas concentration.

One exemplary embodiment of a method of detecting a concentration of a gas, among others, includes: providing a conductometric porous silicon gas sensor; wherein operation of the conductometric porous silicon gas sensor includes: exposing the porous silicon layer to light; introducing the gas to the sensor; and measuring an impedance change in the sensor.

One exemplary embodiment of a device, among others, includes: a conductometric gas sensor including a n-type substrate having a porous layer, wherein a plurality of nanostructures are disposed on a portion of the porous layer, wherein the nanostructure provides a fractional coverage on the porous layer, wherein the sensor is configured to allow light to illuminate the porous silicon layer, wherein the conductometric gas sensor is operative to transduce the presence of a gas into an impedance change in the presence of light, wherein the impedance change correlates to the gas concentration.

Other devices, systems, methods, features, and advantages of the present disclosure will be or become apparent to one with skill in the art upon examination of the following detailed description. It is intended that all such additional devices, systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1.1A illustrates UV-visible reflectance spectra of (1) $TiO_2$ nanocolloid particles; (2) Degussa P25 $TiO_2$ powder; (3) Degussa P25 $TiO_2$ powder nitridated with triethyl-amine; and (4) nitridated $TiO_{2-x}N_x$ nanocolloid particles. FIG. 1.1B illustrates the pore structure of etched n-type PS. FIG. 1.1C illustrates a schematic representation of portion of porous silicon (PS) nanopore coated microstructure (large grey structure) treated with active $TiO_2$ and $TiO_{2-x}N_x$ nanostructures (grey/white spheres) acting to enhance solar pumped reversible sensing. FIG. 1.1D illustrates a schematic of n-type extrinsic semi-conductor level structure and populations.

FIG. 1.2A illustrates a SEM image of undecorated porous silicon pore structure. The pore is approximately one micron in diameter and 4 microns in length. FIG. 1.2B illustrates a SEM image of porous silicon structure deposited with $TiO_2$. Some of the $TiO_2$ nanostructures (10-20 nm) are encircled in white. FIG. 1.2C illustrates a XPS spectrum for the decorated porous structure showing the overall XPS spectrum including background peaks. FIG. 1.1D illustrates a close-up of Ti 2p XPS region.

FIG. 1.3 is a comparison of responses for a PS interface exposed to white light (black dash), to UV light (gray), and in the absence of light (black). The magnitude of the response changes upon UV and white light exposure are identical to those in the absence of light. The gray-black dashed saw-tooth boxes indicate the analyte concentration and the range over which this concentration is exposed to the sensor interface. The numbers in the figure denote the ppm concentration of these exposures.

FIG. 1.4A illustrates a response corresponding to decreasing resistance as $NH_3$ contributes electrons to $TiO_2$ (black dashed) and $TiO_{2-x}N_x$ (grey) treated PS interfaces and to an untreated (black) PS interface. The $TiO_{2-x}N_x$ treated interface is notably more basic (less acidic) than the untreated PS interface. The $TiO_2$ treated PS corresponds to a more acidic interface. FIG. 1.4B illustrates a response to $NH_3$ of a $TiO_2$ treated PS interface without light exposure (black dashed) and exposed to "white light" (grey dashed) and UV radiation (grey). The untreated PS response is inserted for comparison. FIG. 1.4C illustrates a response of a $TiO_{2-x}N_x$ treated PS interface with no light exposure (black) and exposed to UV (grey) and white light (black dashed). Light exposure produces a moderately higher response at higher analyte concentrations.

FIG. 1.5 is a comparison of responses to 1, 2, 3, 4, 5, and 10 ppm $NO_2$ for (FIG. 1.5A) a PS interface consisting of an untreated n-type surface with (FIG. 1.5B) a $TiO_2$ nanostructure deposited PS interfaces for low $TiO_2$ deposition, with (FIG. 1.5C) that which corresponds to the overlap of the response observed for the untreated PS interface (black) to an interface modified with an intermediate concentration of $TiO_2$ (gray), with (FIG. 1.5D) a $TiO_2$ nanostructure deposited PS interface for $TiO_2$ depositions notably higher than those associated with (FIG. 1.5B) and (FIG. 1.5C). Whereas the response curve for the untreated n-type interface corresponds to an increase in resistance with $NO_2$ concentration, the $TiO_2$ decorated surface, at moderate concentrations, displays a decrease in resistance (increase in conductance) as $TiO_2$ now facilitates electron extraction from $NO_2$. The signal begins to saturate between 3 and 4 ppm. FIG. 1.5E illustrates a $TiO_{2-x}N_x$ treated PS interface obtained by treating the $TiO_2$ surface (FIG. 1.5D) which has now been made more basic. The grey dashed saw-tooth boxes indicate the analyte concentration and the range over which this concentration is exposed to the sensor interface.

FIG. 1.6A illustrates a response corresponding to increasing resistance as $NO_2$ extracts electrons from a $TiO_2$ treated PS interface compared to the same interface exposed to UV and white light. The response corresponds to a decrease in resistance for the UV pumped interface. FIGS. 1.6B and 1.6C illustrate the responses to $NO_2$ of two $TiO_{2-x}N_x$ treated PS interfaces without light exposure and exposed to white light. FIG. 1.6B corresponds to a lower fractional deposition such that $NO_2$ dominates $TiO_2$ (FIG. 1.6C) corresponds to a significantly higher fractional deposition. The grey dashed saw-tooth boxes indicate the analyte concentration and the range over which this concentration is exposed to the sensor interface. The white light exposure greatly enhances response. See text for discussion.

FIG. 1.7 is a close up view of the response of a $TiO_{2-x}N_x$ decorated PS interface at an $NO_2$ concentration of 10 ppm. The response at first begins to rise during the initial exposure to $NO_2$ and subsequently decreases rising again sharply as the $NO_2$ flow ceases.

FIG. 1.8 illustrates the response of an untreated porous silicon sensor to $NO_2$, to $NO_2$ in the presence of ultraviolet light excitation, and to $NO_2$ in the presence of white light excitation.

FIG. 2.1 illustrates a schematic representation of PS sensor interface structure.

FIG. 2.2A illustrates a close up side view of a hybrid porous silicon film. FIG. 2.2B illustrates a nanoparticle tin-oxide coating on the porous silicon micropores. FIG. 2.2C illustrates 10 to 30 nm $Au_xO$ nanostructures on the porous silicon micropores.

FIG. 2.3 illustrates a porous Si gas sensor schematic. The resistance change is measured via precision microprobes when the porous silicon interface is exposed to a test gas. A SiC layer also serves as an insulation layer as the resistance response of the porous layer is measured through gold contacts.

FIG. 2.4A illustrates a configuration for gas sensor testing and FIG. 2.4B illustrates a top view of sensor showing the PS surface between gold pads for electrical connection.

FIGS. 2.5A and 2.5B illustrate the variation of the position of the Fermi level with temperature.

FIG. 2.6 illustrates a comparison of responses for sensors having an untreated PS interface with those treated with gold or tin to form $SnO_x$ (x=1,2) and gold clustered oxide $Au_xO$ nanostructured island deposits (FIG. 2.2). Note that the three bases, $NH_3$, NO, and CO introduced to the treated "p-type" silicon result in a positive resistance change and that the relative responses to the strong (hard) base $NH_3$ and the weak (soft) bases NO and CO are distinct. The significant differences in relative response are maintained with improved interfaces whose S/N is up to two orders of magnitude greater (Seals et al. 2002; Lewis et al. 2005; Ozdemir and Gole 2008b). This represents earlier data whose resistance response (sensitivity) has been greatly improved whereas the ratios of resistance have remained the same.

FIG. 2.7 illustrates a $PH_3$ response to an electroless $Au_xO$ coating. Here, 1, 2, 3, 4, 5 ppm of $PH_3$ is pulsed onto the sensor surface every 300 s. For the first 1800 s an $N_2$ purge is applied for resistance stabilization.

FIG. 2.8 illustrates a response of $NO_2$ to a p-type PS sensor. Note that upon the introduction of $NO_2$ the resistance of the system "bottoms-out" as conductance is maximized.

FIG. 2.9 illustrates XPS spectra for the metal-based nanostructure deposited PS sensors and fitting curves to the spectra. FIG. 2.9A illustrates an XPS stectrum of a dominantly SnO deposited sensor. SnO ($Sn^{2+}$) has peaks in the range of 485.6-487.0 eV, $SnO_2$ ($Sn^{4+}$) has peaks in the range of 486.1-487.1 eV. FIG. 2.9B illustrates an XPS spectrum of a dominantly $NiO_x$ deposited sensor. Nickel has an oxidation peak ($2p_{1/2}$) located ~871.8 eV for NiO ($Ni^{2+}$) and has peaks ($2p_{3/2}$) in the range of 853.6-857.2 eV. $Ni_2O_3$ ($Ni^{3+}$) shows peaks from 855.8 eV to 856.5 eV. FIG. 2.9C illustrates an XPS spectrum for a dominantly $Cu_xO$ deposited PS surface. CuO ($Cu^{2+}$) has peaks ($2p_{1/2}$) in the range of 952.5-952.7 eV and has peaks ($2p_{3/2}$) in the range of 933.3-934.3 eV. $Cu_2O$ ($Cu^{1+}$) has peaks in the range of 932.0-932.8 eV. FIG. 2.9D illustrates an XPS spectrum of Au $4f_{5/2}$ and Au $4f_{7/2}$ doublets (NIST 2003) which demonstrate minimal oxidation.

FIG. 2.10 illustrates estimated hard and soft acidities and basicities based on resistance changes relative to a p-type porous silicon interface.

FIGS. 2.11A-C illustrates the response of an n-type PS micro/nanostructured interface to 1, 2, 3, 4, 5 and 10 ppm $NO_2$ (A) and $NH_3$ (C) and 1-5 ppm NO (B). These gases were pulsed onto the PS interface with a 300 s half-cycle followed by a 300 s half-cycle UHP cleaning. The system was purged with UHP nitrogen 1800 s before operation. See text for discussion.

FIGS. 2.12A-G illustrates the comparison of responses for 1, 2, 3, 4, 5, and 10 ppm NO for A, E, G sensors having an untreated n-type PS interface with those treated with B $TiO_2$, C $SnO_x$, D NiO, F $Cu_xO$, and H $Au_xO$ fractional nanostructured island depositions. The untreated PS interface in A is that treated with $TiO_2$ in B. The response for the untreated PS interface in A is duplicated precisely for the untreated PS interfaces to which we compare in C for $SnO_x$ and D for NiO. The untreated PS responses in E and G correlate with the $Cu_xOF$ and $Au_xO$ responses in H respectively. NO was pulsed onto these interfaces with a 300 s half-cycle followed by a 300 s half-cycle UHP cleaning. The system was purged with UHP nitrogen for 1800 s before operation.

FIG. 2.13A illustrates a TEM image and FIG. 2.13B illustrates an EDS (inset) of Pd nanoparticles on $SnO_2$ nanowires.

FIG. 2.14A illustrates a low magnification TEM image of an 800° C.-annealed, core-shell nanowire. FIG. 2.14B illustrates a corresponding XRD Spectrum.

FIG. 2.15A illustrates a schematic view of the formation of electron depleted regions beneath and in the immediate vicinity of two Pd nanoparticles. FIG. 2.15B illustrates the response of a pristine (dashed line) and Pd-functionalized (solid line) nanostructure to sequential oxygen and hydrogen pulses at 473° K (top pane) and 543° K (bottom).

FIG. 2.16 illustrates a gas sensor response to the pulsing of ammonia between 0 and 5 ppm in research grade $N_2$.

FIG. 2.17 illustrates a FFT analysis of a gas pulsing experiment performed on a sensor (right) compared to the signal of a device responding to the same external noise in the absence of no gas pulsing (left). The raw signal of each sensor is shown (top) as well as the filtered FFT of the sensors (bottom). Separate peaks are generated at a pulsing frequency (0.0167 Hz) and the heating frequency (0.0042 Hz) (Lewis et al. 2007).

FIGS. 2.18A and B illustrates an FFT of a PS gas response a) before filtering and b) after filtering.

FIG. 2.19 illustrates a response to $NH_3$ after a sensor is subjected to a rejuvenation process. The contaminated sensor response is in blue, the rejuvenated sensor response is in black.

FIGS. 2.20A-C illustrate a comparison of photocatalytic degredation of methylene blue for $TiO_{2-x}N_x$ (FIG. 2.20A) nanoparticles and nitrided Degussa P25 (FIG. 2.20B). In FIG. 2.20C, white column indicates Degussa P25; black center column indicates nitrided Degussa; grey column indicates $TiO_{2-x}N_x$ nanocolloid (Chen et al. 2005; Gole et al. 2004).

FIG. 2.21 illustrates the selectivity of a PS device to $NH_3$ in 20 ppm $NO_R$. The response time (<10 seconds) of the gas sensor is also demonstrated.

FIG. 2.22 illustrates a comparison of a metal oxide (usually $SnO_2$ or $WO_3$) elevated temperature (150-500° C.) heat controlled sensors separated from their electronics by a channel with a heat sunk PS sensor operating at room temperature and capable of operation to temperatures of at least 80° C.

FIG. 2.23 illustrates SEM micrographs of a porous silicon filter. In the top images, the tips of the pores can be seen before (A) and after (B) they begin to spread out in their face directions. The second row of images show the front (C) and back (D) of a filter. Note that pore spreading is significant in the filter back. The final image (E) represents the direct Lift-off of PS-based film-filter (~20 microns) from the surface of an etched PS film. Pore diameter is approximately one micron.

FIGS. 2.24A and B illustrate a comparison of responses to 1, 2, 3, 4, 5, and 10 ppm $NO_2$ for A a particular untreated n-type PS interface and B an interface treated with a fractional deposition of nanostructured $SnO_x$. $NO_2$ was pulsed onto the interfaces with a 300 s half cycle followed by a 300 s half cycle UHP nitrogen cleaning FIG. 2.24B is suggested to result, at least in part, from the chemisorptive $SnO_x$—$NO_2$— interaction.

FIG. 2.25 illustrates Tables A, B, and C. Table A describes hard and soft acids and bases. Table 2/2 describes the relative increase in response (increase in resistance) of $SnO_2$, NiO, $Cu_xO$, and gold clustered oxide, $Au_xO$ (x>>1) treated "p-type" PS interfaces relative to the untreated interface. Table B constitutes a response matrix to the gases $PH_3$, NO, $NH_3$, and $SO_2$. Table C describes the relative increase or decrease in resistance (decrease or increase in conductance) of $TiO_2$, $SnO_x$, NiO, $Cu_xO$, and gold clustered oxide, $Au_xO$ treated "n-type" PS interfaces. The table constitutes a response matrix for the gases NO, $NO_2$, and $NH_3$. * indicates decrease in resistance with analyte exposure ** indicates initial response.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that any pair of intervening values in the stated range are encompassed within the disclosure although they may not be specifically recited, subject to any specifically excluded limit in the stated range (e.g., if the range is 1 to 100, then the range of 10 to 20 is also included and can be claimed even if not specifically recited).

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, material science, and the like, which are within the skill of the art. Such techniques are explained fully in the literature.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

DEFINITIONS

The term "detectable" refers to the ability to detect a signal over the background signal.

The term "detectable signal" is a signal derived from an impedance change upon the interaction of a gas with a porous silicon layer or a porous silicon layer having a nanostructured deposit on the porous silicon layer. The detectable signal is detectable and distinguishable from other background signals. In other words, there is a measurable and statistically significant difference (e.g., a statistically significant difference is enough of a difference to distinguish among the detectable signal and the background, such as about 0.1%, 1%, 3%, 5%, 10%, 15%, 20%, 25%, 30%, 40% or more difference between the detectable signal and the background) between the detectable signal and the background. Standards and/or calibration curves and/or arrays of porous silicon sensors can be used to determine the relative intensity of the detectable signal and/or the background.

Discussion

Embodiments of the present disclosure include sensors, arrays of sensors, devices including sensors, methods of making sensors, methods of using sensors, and the like, whereupon with illumination with light the sensor has enhanced sensitivity. In an embodiment, the present disclosure includes porous silicon (PS) sensors, arrays of PS sensors, devices including PS sensors, methods of making PS sensors, methods of using PS gas sensors, and the like.

Typically, a sensor is not exposed to light due to the nature of its construction and/or because light deteriorates the sensor or sensor performance. An advantage of an embodiment of the present disclosure is that the sensitivity of the sensor can be enhanced (e.g., about 150% or more) when exposed to visible and/or ultraviolet light as compared to the same sensor that is not exposed to light. Thus, the sensor or sensor system can be configured so that a region (e.g., porous silicon) of the sensor is illuminated by light (e.g., natural and/or artificial light). Additional details will be described herein.

Embodiments of the present disclosure can be understood based on the Inverse Hard/Soft Acid/Base (IHSAB) principle/approach. The Inverse Hard/Soft Acid/Base (IHSAB) principle/approach, as it correlates with a basis in physisorption (electron transduction), complements the HSAB principle for hard/soft acid/base interactions and can be correlated with a basis in density functional theory (DFT). The basis for correlation follows the principle that soft-soft acid/base interactions produce significant covalent bonding and hard-hard combinations produce significant ionic bonding. The HSAB principle states that hard acids prefer to coordinate to hard bases and soft acids prefer to coordinate to soft bases. In contrast, the driving principle to promote physisorption (electron transduction) represents the inverse of that necessary to form strong chemical bonds. This principle is manifest through the interactions of metal oxide nanostructures as they influence the nature of the majority carriers in a p- or n-type semiconductor. In an embodiment, nanoporous silicon layers positioned on porous silicon (PS) micropores facilitate the deposition of nanostructured metal/metal oxides which provide distinctly higher variable sensitivities and selectivity for a given extrinsic semiconductor interface. In an embodiment, the PS surface is treated with fractional depositions (e.g., islands of nanostructures), much less than a monolayer to insure that the nanostructures do not begin to cross talk and, in so doing diminish signal to noise. This deposition can be made to produce a dominant physisorptive (sensors) or chemisorptive (micro-reactors) character at the semiconductor interface as the deposited nanostructures act to focus the nature of the surface interaction. However, the nature of the extrinsic semiconductor, the manner in which its donor and/or acceptor levels can be manipulated, and its transformation to intrinsic character also represent important variables.

For example, light (e.g., visible and/or UV light) absorbed by a photocatalyst disposed on the surface of an n-type semiconductor sensor (e.g., $TiO_2$ disposed on porous silicon) at room temperature can enhance electron transfer that can be used to improve a sensing process by modifying the conductivity due to the concentration of available electrons in an n-type extrinsic semiconductor interface. Embodiments of the present disclosure can use this feature to enhance (e.g., about 50% or more, about 100% or more, or about 150% or more) the sensitivity of the sensor relative to the same sensor that is not illuminated by light.

An embodiment of the present disclosure describes a conductometric gas sensor that is operative to measure an impedance change that corresponds to a gas concentration (e.g., a gas concentration can be determined based on the impedance change or the magnitude of the impedance change and this concentration can be independently evaluated for calibration) when illuminated with light. More particularly, the conductometric sensor transduces the presence of a gas into an impedance signal, which is measured by another device in communication with the conductometric sensor. Therefore, the term "measure" used in reference to the conductometric sensor can include the conductometric sensor in combination with another circuit or device (e.g., impedance analyzer, sensor and shunt circuit, and the like) to measure the impedance (e.g., the detectable signal). The conductometric sensor can be used to detect gases or liquids. In particular, conductometric sensors, in accordance with the present disclosure, have a rapid and reversible response to analyte gases at room temperature while being illuminated by light.

In an embodiment, the n-type semiconductor is PS, so the sensor can be referred to as a conductometric PS gas sensor (also referred to as a "PS gas sensor" or "conductometric PS sensor"). Although some embodiments of the present disclosure are described as PS, other n-type semiconductor materials can be used and include a porous layer. There is no intention to limit embodiments of the present disclosure to PS materials and other materials, such as those described herein, can be used.

In an embodiment, the conductometric PS gas sensor can be made from an n-type PS substrate. In an embodiment, a conductometric PS gas sensor made from n-type PS can operate at a lower concentrations than p-type PS based conductometric PS gas sensors to extend down to the lowest parts per billion (ppb) less than 100 ppb, less than about 75 ppb, less than about 50 ppb, less than about 35 ppb, about 1 to 100 ppb, about 1 to 75 ppb, about 1 to 50 ppb, about 1 to 35 ppb), while p-type PS based conductometric PS gas sensors operate in a linear fashion at pressures higher (greater than 5 ppm) than n-type PS based conductometric PS gas sensors. Thus, an embodiment of the present disclosure can include both p-type and n-type PS based conductometric PS gas sensors that can be used in a wide dynamic range of gas concentrations. In general, these detection levels could be obtained where a different n-type semiconductor is being used. Some detection abilities for some specific gases are given in the Examples, and these illustrate the general sensitivity of the sensor which can be extended to other gases or gas mixtures.

Embodiments of the present disclosure provide for a concept that is predictive of significant and predictable changes in the conductometric sensor (e.g., conductometric PS sensor) sensitivity for a variety of gases when exposed to light. Rapidly responding, reversible, sensitive, and selective conductometric PS sensors can be formed (1) with a highly efficient electrical contact to a porous silicon layer (e.g., a nanopore covered microporous layer), while also including (2) deposited nanostructures (e.g., nanostructures as nanostructured fractional deposits, which enhance the sensitivity of the sensor illuminated by light), using embodiments of the present disclosure.

In an embodiment, the nanostructures can be deposited as distinctly variable nanostructures that can be chosen to be deposited on a portion (e.g, distinct islands) of the porous silicon layer, where the resulting conductometric PS sensor provides a range of sensitivities for a given analyte using a concept complementary to that of hard and soft acid-base interactions (HSAB) and commensurate with a basis in dominant physisorption. The physisorption interaction involves electron transduction between the gas and nanostructured deposit. The physisorption interaction may involve a change in the electronic orbital patterns of the nanostructured deposit but the key is the analyte gas and orbital miss-match which leads to weak interaction. A physisorption interaction is a reversible interaction of the nanostructured deposit with the gas. A physisorption interaction is not a chemisorption reaction that involves a chemical reaction that may not be reversible. The concept, based on the reversible interaction of hard acids and bases with soft bases and acids corresponds (1) to the inverse of the HSAB concept and (2) to the selection of a conductometric PS sensor and a porous silicon surface (e.g., nanostructures islands) and analyte materials, which do not undergo strong covalent or ionic bonding but rather represent a much weaker orbital interaction where a significant HOMO-LUMO and additional orbital mismatches dominate the interaction as a reversible physisorption interaction (electron transduction). For example, at 300° K, the donor level population has been depleted sufficiently so that there are a significant number of levels available for population when a basic analyte interacts with the decorated semiconductor interface, contributes electrons to the donor levels, enhances the majority charge carrier concentration, and increases conductance. This process can eventually "top out" the level population. Similarly, an acidic analyte, as it withdraws electrons, decreases conductance, depletes and can eventually "bottom out" the donor level population. Embodiments of the present disclosure provide for notably higher sensitivities and selectivity based on impedance changes.

An embodiment of the present disclosure can be advantageous for one or more of the following reasons: (1) enhanced sensitivity when exposed to light relative to the same sensor that is not illuminated, (2) its operation at room temperature as well as at a single, readily accessible, temperature with an insensitivity to temperature drift, (3) its potential operation in a heat-sunk configuration allowing operation to a surface temperature of 80° C. even in highly elevated temperature environments (in sharp contrast to metal oxide sensors), (4) its ease of deposition with a diversity of gas-selective materials to form sensor arrays, (5) its low cost of fabrication, (6) its low cost and ease of rejuvenation after contamination, (7) its low cost of operation, and/or (8) its ability to rapidly assess false positives by operating the sensor in a pulsed gas mode.

It should be noted that the time frame for measuring the gas concentration depends, in part, on the experimental configuration for gas delivery and the particular application and gas being measured. The presence of the gas can be measured in a time frame less than or equal to 2 seconds in some embodiments which can be dictated by the gas delivery system, while in other embodiments, the time frame for a precise concentration measurement may be longer. In an embodiment, the sensor itself responds in less than 2 seconds. It should be noted that impedance includes contributions from one or more of resistance, capacitance, and inductance, and measurement of impedance includes the measurement of one or more of resistance, capacitance, and inductance. In an embodiment, the impedance analyzer measures the resistance and capacitance only.

Embodiments of the present disclosure can be used to measure the concentration of a gas or a mixture of gases when the gas or the gas mixture is known or substantially known, while being illuminated by light. For example, if the environment that the conductometric PS sensor is to be used in is known to include ammonia, the conductometric PS sensor can be used to measure the concentration of ammonia. In another example, if the environment that the conductometric PS sensor is to be used is known to include ammonia and $H_2S$, then an array matrix of conductometric PS sensors (e.g., 2, 3, 4, 6, 8, or more) can be used to measure the concentration of each gas or the relative concentration of each gas, where one or more portions of the array are illuminated by light. In an embodiment, the array of conductometric PS sensors can be designed so that each of the conductometric PS sensors has a greater sensitivity for detection of a specific gas. In addition, the array of conductometric PS sensors allows the concentration of the gases to be compared to one another on relative terms.

In an embodiment, the conductometric PS sensor includes a silicon substrate (n-type), a protective layer on a portion of the silicon substrate, an n-type PS layer (or region) on a portion of the silicon substrate that is not covered by the protective layer, and two or more distinct gold contacts disposed onto a portion of the PS region and the protective layer. A plurality of nanostructures (sometimes referred to as a "nanostructured deposits") can be disposed in a fractional manner (e.g., non-contiguous islands) on and/or within the n-type PS layer that is not covered by the contacts, which enables the conductometric PS sensor to respond more strongly to certain gases relative to others depending on the nanostructures used.

In an embodiment, the device and/or system including the conductometric PS sensor is configured so that the PS layer can be illuminated by light (e.g., visible and/or UV light). In an embodiment, the light can have an energy of about 1 lumen/cm-sterad-nm to about 500 lumen/cm-sterad-nm (e.g, the radiation level of the sun) or about 1 lumen/cm-sterad-nm to about 100 lumen/cm-sterad-nm. In an embodiment, the light energy can be adjusted according to the desired detection level, so in some instances a low light energy is sufficient to achieve the desired detection level.

In an embodiment, the device and/or system includes a controllable light source (e.g., LED or other light source that can be operated at a desired wavelength(s)) that can illuminate the PS layer. In an embodiment, the device, system, and/or sensor can be configured to allow for the PS layer to be illuminated by light (e.g., natural and/or artificial) from the surrounding area. For example, the device, system, and/or sensor can include a window or an opening that permits light to illuminate the PS layer. In an embodiment, the window can include a material transparent to visible light and/or UV light such as glass or a filter, so that the PS layer is separated from the source of the light, whether the light source is part of the device or system, or if the light source is natural light. In another embodiment, there is not a barrier between the source of the light and the PS layer and the light enters through an opening to the PS layer.

In an embodiment, the PS layer can be optionally illuminated by one or of both natural and artificial light depending on the operational environment to which the sensor is disposed. In an embodiment, the device or system may be positioned outside or placed so that natural sunlight shines on the PS layer for a certain time period, in which case artificial light is not needed during that time period. Artificial light can be used to illuminate the PS layer during times that natural sunlight does not illuminate or does not sufficiently illuminate (e.g., night time, cloud cover, etc) the PS layer. In this regard, the device or system can be designed so that illumination of the PS layer is monitored and controlled.

In an embodiment, the protective layer can include, but is not limited to, a silicon carbide layer, a silicon nitride layer, a silicon oxynitride ($SiO_xN_y$) layer, an insulating dielectric film, a ceramic layer, and combinations thereof. In an effort to be clear, the protective layer may be referred to as the silicon carbide layer hereinafter, but the protective layer could be any one of the layers described above in other embodiments.

In an embodiment, the n-type PS layer can include a macroporous/nanoporous hybrid framework. The nanopores are superimposed on the walls of the macropores. In an embodiment, the macropores can be about 0.5 to 20 μm deep and about 1 to 3 μm in diameter. In an embodiment, the nanopores can be about 1 to 20 nanometers in diameter.

In an embodiment, the contact can be disposed on and within the macroporous and nanoporous hybrid framework as well as extend above the n-type PS layer and onto the protective layer (e.g., silicon carbide layer). In other words, the material fills in a portion of the n-type PS layer and then forms a layer on top of the n-type PS layer. The contacts are distinct and separated from one another by a space or area (e.g., a portion of the PS layer and a portion of the protective layer). In an embodiment, the contact can include one or more contact portions. In other words, one portion can be disposed on the n-type PS layer and one portion disposed on the protective layer, but the two portions are contiguous in that a single metal layer extends from the n-type PS layer onto the top of the n-type PS layer and onto the protective layer. The contacts can be made of a metal or a combination of metals such as, for example, gold. In an embodiment, the contact includes a pre-coating layer usually titanium, and a metal layer usually gold, disposed onto the pre-coating layer. The pre-coating layer can be used to improve the electrical connection of the contact to the n-type PS layer.

As mentioned above, the exposed portion of the n-type PS layer not covered by the contacts can have a plurality of nanostructures deposited (e.g., nanostructure islands) on and/or within the n-type PS layer (e.g., a combined macroporous/nanoporous hybrid framework). The nanostructures can include, but are not limited to, a metal material, a metal oxide material, a metal oxynitride material, and combinations thereof. In an embodiment, the nanostructures can be discrete and/or clustered nanostructures and/or nanomaterials on and/or with the n-type PS layer. In another embodiment, the nanostructures can be deposited onto and/or within discrete areas of the n-type PS layer.

In an embodiment, the nanostructure can include a nanoparticle such as a nanosphere. In an embodiment, the nanostructure could be a nanowire, a nanodisk, or a nanobelt. In an embodiment, the nanoparticle can be uncoated or coated. For example, the nanostructure can be made of metals such as silicon (Si), tin (Sn), chromium (Cr), iron (Fe), nickel (Ni), silver (Ag), titanium (Ti), cobalt (Co), zinc (Zn), platinum (Pt), palladium (Pd), osmium (Os), gold (Au), lead (Pb), iridium (Ir), rhodium (Rh), ruthenium (Ru), molybdenum (Mo), vanadium (V), aluminum (Al), metal oxides of each of these, or metal oxynitrides of each of these. In an embodiment, the metal oxide nanostructure can be converted to a metal oxynitride nanostructure in situ. In an embodiment, the nanostructure can be made of: aluminum oxide ($Al_2O_3$, $AlO_x$, x is 1 to 2), aluminum oxynitride, silicon oxide ($SiO_x$, x is 1 to 4), silicon oxynitride, tin oxide ($SnO_x$, x is 2 to 4), tin oxynitride, chromia ($Cr_2O_3$), chrome oxynitride, iron oxide ($Fe_2O_3$, $Fe_3O_4$, or FeO), iron oxynitride, nickel oxide (NiO), nickel oxynitride, silver oxide (AgO), silver oxynitride, cobalt oxide ($Co_2O_3$, $Co_3O_4$, or CoO), zinc oxide (ZnO), platinum oxide (PtO), palladium oxide (PdO), vanadium oxide ($VO_2$), molybdenum oxide ($MoO_2$), lead oxide (PbO), titanium oxide ($TiO_2$), titanium nitride ($TiN_1$), titanium oxynitride ($TiO_{2-x}N_x$), clustered oxides of each of these, other metal oxides, and a combination thereof. In a particular embodiment, the nanostructure can include titanium oxide ($TiO_2$) nanoparticles and/or titanium oxynitride ($TiO_{2-x}N_x$) nanoparticles. In an embodiment, the titanium oxynitride nanoparticles can be formed in situ. Using a variety of metal and metal oxide materials, the conductometric PS sensor can be designed to provide selectivity for a particular gas.

In an embodiment, each nanostructure, a group of nanostructures, or a cluster of nanostructures, form an island on the n-type PS layer. In an embodiment, the islands are spaced apart so there is no cross talk between the islands that would impede, substantially impede (e.g., impede about 50% or more, about 75% or more, about 90% or more, or about 50 to 90%, relative to no impedance), or substantially interfere (e.g., interfere about 80% or more, about 90% or more, or about 95% or more, relative to no interference) with the detection of the gas(es) of interest.

Embodiments of the conductometric PS sensor having a plurality of nanostructures on the n-type PS layer can provide enhanced sensitivity and selectivity to certain gases while being illuminated with light. In particular, concentrations of select gases can be measured in the presence with one or more additional gases, where selected gases are more strongly sensed (e.g., impedance change detected). In an embodiment, the selectivity to one gas over one or more others can be controlled by selection of the type or combination of types of nanoparticles.

As briefly mentioned above, the conductometric PS sensor responds and is operative to measure an impedance change (e.g., an impedance magnitude change) across a first contact and a second contact that corresponds to a concentration of a gas in contact with the PS surface, while being illuminated with light. The sensitivity of the conductometric PS sensor is defined as the relative increase or decrease in impedance over a time frame following exposure to a concentration of a gas of interest. It should also be noted that the sensitivity is, in part, a function of the analyte gas of interest, the nature of the nanostructure deposites, and whether the extrinsic semiconductor is n- or p-type. In particular, relative to p-type conductometric PS sensors, the n-type conductometric PS sensors operate at lower relative gas concentrations for a particular analyte gas.

The operating parameters of the conductometric PS sensor include, but are not limited to, a bias voltage, an AC voltage frequency, an AC voltage amplitude and combinations thereof. The conductometric PS sensors operate at a bias voltage between about 10 and 3000 millivolts DC. Also one can use an AC voltage frequency between 100 and 100,000 Hz, and an AC voltage amplitude between 1 and 1000 millivolts, or a combination thereof.

As mentioned briefly above, the impedance change can be measured with an impedance analyzer, a sensor and shunt circuit, or other impedance measurement devices. An embodiment of the sensor and shunt circuit uses a high impedance resistor in parallel with the sensor (conductometric PS sensor or components thereof). The resistor shunts the stray capacitance (removes high frequency noise), resulting in a resistive measurement.

The conductometric PS sensor can be used in a variety of ways including, but not limited to, a stand-alone detector device or system, or a device or system including an array of stand-alone detectors (e.g., one or more types of n-type conductometric PS sensors and one or more types of p-type conductometric PS sensors), where in each instance the light can be produced using an artificial light source(s) within or separate from the device or system and/or natural light can be used. The conductometric PS sensor can be used to detect gases (e.g., combustion generated gases such as carbon monoxide, carbon dioxide, sulfur dioxides, nitrogen oxides, and hydrogen sulfide) while illuminating the PS layer. In particular, conductometric PS sensors, in accordance with the present disclosure, can provide a rapid and reversible response to analyte gases (e.g., including hydrogen chloride (HCl), ammonia ($NH_3$), phosphine ($PH_3$), carbon monoxide (CO), sulfur dioxide ($SO_2$), hydrogen sulfide ($H_2S$) nitric oxide ($NO_x$), and toluene) at room temperature while being illuminated by light. Additional details regarding analyte gases are described in the Examples.

In addition, the conductometric PS sensor can be used as an array, where multiple conductometric PS sensors (e.g., one or more types of n-type conductometric PS sensors and one or more types of p-type conductometric PS sensors) are uniquely sensitive to different gases of interest thereby enabling an array to measure the concentration of multiple gases simultaneously (e.g., an appropriately treated conductometric PS sensor can be made to respond more strongly to one gas over a second gas), where each PS sensor can include its own light source or a single light source can be used. In addition, an array of conductometric PS sensors can be used to enhance sensing selectivity as the array of conductometric PS sensors provide multiple data points per tested sample which can be analyzed in a matrix format to provide selectivity for one gas over another based on the individual conductometric PS sensors within the conductometric PS sensor array. Thus, an array of conductometric PS sensors includes conductometric PS sensors sensitive to one gas over another and, in this sense, to select gases. In this regard, the array of conductometric PS sensors can be used to detect multiple analytes simultaneously.

Embodiments of the present disclosure also include methods of making conductometric PS sensors. In general, the conductometric PS sensor can be fabricated by first providing an n-type silicon substrate (or other appropriate substrate) having a protective layer, such as a silicon carbide layer, disposed on a first portion of the silicon substrate. Then, a first area on the silicon substrate is converted into a n-type PS layer, where the first area does not have a silicon carbide layer disposed thereon. Next, a first contact (e.g., a first contact pre-coating (e.g., Ti or Cr) and the first contact (e.g., Au)) is formed onto a first portion of the n-type PS layer and onto a first portion of the silicon carbide layer. The first portion of the silicon carbide layer is contiguous with the first portion of the n-type PS layer as described above. A second contact (e.g., a second contact pre-coating (e.g., Ti or Cr) and the second contact (e.g., Au)) is formed onto a second portion of the n-type PS layer and onto a second portion of the silicon carbide layer. The second portion of the silicon carbide layer is contiguous with the second portion of the n-type PS layer as described above. A third portion of the n-type PS layer is between the contacted first portion and the second portion of the n-type PS layer. The first and second contacts can be formed at the same time. Specifically, the first and the second contact pre-coatings are formed and then the first and second contacts are formed on the first and second contact pre-coatings, respectively. The first and second contact pre-coatings are advantageous in that the first and second contacts enable a superior electrical connection to be formed. In addition, the first and second contacts can be formed using a shadow mask technique. One or more types of nanostructures can be fractionally disposed on the n-type PS layer, where the nanostructure(s) form islands on the n-type PS layer.

Additional fabrication steps can be conducted. For example, an additional fabrication step includes cleaning the n-type PS layer with a mixture of one part hydrochloric acid (e.g., about 44%) in about five parts methanol for about four hours. In addition, a fabrication step for forming a nanostructured deposit on the porous silicon layer can be performed.

In an embodiment, the silicon substrate can be replaced with any extrinsic n-type semiconductor (e.g., GaP, InP, CdTe, and the like) onto which a porous microstructure can be generated. In an embodiment, the silicon substrate can include wafers, such as, but not limited to, n- or $n^+$-type doped wafers, n- or $n^+$-type phosphorous doped wafers. In an embodiment, the silicon substrate can include wafers, such as, but not limited to, n- or $n^+$-type doped silicon wafers, n- or $n^+$-type phosphorous doped silicon wafers.

In an embodiment, other materials can be used in place of the silicon carbide layer such as, but not limited to, a silicon nitride layer, a $SiO_xN_y$ layer, an insulating dielectric film, and a ceramic layer.

In an embodiment, the n-type PS layer can be prepared by electrochemically etching a portion of the silicon substrate with acetonitrile, hydrofluoric acid, tetrabutylammoniumperchlorate (TBAP), and water, for example. Additional details regarding the preparation of the n-type PS layer are presented in more detail herein.

In an embodiment, the first contact pre-coating layer and the second contact pre-coating layer can be made from titanium or chromium, for example, and can be about 100 to 300 angstroms thick or about 200 angstroms thick. The first contact pre-coating and the second contact pre-coating can be disposed onto the two portions of the PS substrate via techniques such as, but not limited to, electron-beam evaporation, sputtering, electroless plating, and electroplating.

In an embodiment, the first and second contacts and can be made of metals, such as, but not limited to, gold (Au), and can be about 1000 to 4000 angstroms thick or about 3000 to 5000 angstroms thick to facilitate wire bonding. The first contact and the second contact can be disposed onto the two portions of the PS substrate via techniques such as, but not limited to, electron-beam evaporation, sputtering, electroless plating, and electroplating.

In an embodiment, the nanostructures can be can be disposed using techniques such, but not limited to, electron-beam evaporation, sputtering, silk-screen printing, electroless plating, and electroplating.

After the conductometric PS sensor is formed, the conductometric PS sensor can be validated. In this regard, embodiments of this disclosure include methods of selecting a conductometric PS sensor having certain performance characteristics, methods of analyzing the data measured using the conductometric PS sensor, and methods of measuring the concentration of a gas. In addition, the method of validating includes detecting false positives (e.g., determining that an impedance change is from the gas of interest and not a response caused by another source). Furthermore, the present disclosure provides methods of analyzing data for the conductometric PS sensor as well as for other devices and sensors.

EXAMPLES

Now having described the embodiments of the present disclosure, in general, the following examples describe some additional embodiments of the present disclosure. While embodiments of the present disclosure are described in connection with the examples and the corresponding text and figures, there is no intent to limit embodiments of the present disclosure to this description. On the contrary, the intent is to cover all alternatives, modifications, and equivalents included within the spirit and scope of the embodiments of the present disclosure.

Example 1

Visible and UV light are demonstrated to significantly enhance the sensing properties of an n-type porous silicon (PS) extrinsic semiconductor interface to which $TiO_2$ and oxynitride, $TiO_{2-x}N_x$, photocatalytic nanostructures are fractionally deposited. The acid/base chemistry of $NH_3$, a moderately strong base, and $NO_2$, a moderately strong acid, couples to the majority charge carriers of the doped semiconductor as the strong acid, $TiO_2$, enhances the extraction of electrons from $NH_3$ and the more basic $TiO_{2-x}N_x$ decreases the efficiency of electron extraction relative to the untreated interface. In contrast, $NO_2$ and a $TiO_2$ or $TiO_{2-x}N_x$ nanostructure decorated PS interface compete for the available electrons leading to a distinct time dependent electron transduction dynamics as a function of $TiO_2$ and $TiO_{2-x}N_x$ concentration. Only small concentrations of $TiO_2$ and its oxynitride and no self-assembly are required to enhance the response of the decorated interface. With light intensities less than a few lumens/cm²-sterad-nm, responses are enhanced by up to 150% through interaction with visible (and UV) radiation. These light intensities should be compared to the sun's radiation level, ~500 lumens/cm²-sterad-nm suggesting the possibility of solar pumped sensors. The behavior which we observe in these systems is largely explained by the recently developed Inverse Hard and Soft Acid/Base (IHSAB) concept.

Introduction:

Where electrical power is at a premium, the ability to create a sensor response at room temperature using only white light (or minimal UV light) excitation can provide a valuable asset. Since white light represents the major component of the solar spectrum, a light absorption process that subsequently leads to directed electron transduction corresponds to "solar pumped" sensing. Sensors which operate in the absence of or with minimal battery power and can be based on solar energy offer a significant development in our ability to detect analytes and, if properly configured, sequester and destroy analytes.

The cost and accessibility of UV photons has made it desirable to develop highly stable and inexpensive pollutant mediating photocatalysts which have significant activity under visible light excitation utilizing the solar spectrum or interior room lighting[1]. These photocatalysts can also offer the potential for the significant improvement of sensor devices[2]. Here, we have used the strong acid, $TiO_2$, and its visible light absorbing and more basic counterpart, $TiO_{2-x}N_x$, as the agents to mediate electron transduction at a treated extrinsic semiconductor interface. This study demonstrates that solar and/or interior room lighting absorbed by a photocatalyst at room temperature can enhance electron transfer that can be used to improve a sensing process by modifying the conductivity due to the concentration of available electrons in an n-type extrinsic semiconductor interface.

To demonstrate white light enhanced sensing we combine a metal oxide nano-photocatalyst with a porous n-type extrinsic silicon semiconductor interface. We form a light accessable nanostructure decorated nanopore coated microporous array[2,3] (FIG. 1.1) to which the active nanostructures are deposited. We describe results obtained as nanostructured acidic $TiO_2$ and its visible light absorbing counterpart, $TiO_{2-x}N_x$, to which we introduce considerable basic character, are deposited, in fractional deposition, to an n-type porous silicon (PS) interface and optically pumped. The observations made for the doped systems are compared to and gauged by the electron transduction observed in the absence of light as well as that observed for the untreated PS interface. The nanostructure deposition[2,3] must be maintained at a sufficiently low level so as to avoid cross-talk between the nanostructures which can lead to a noisy device and the loss of functionality.

FIG. 1.1(D) represents a schematic diagram of the donor level population and the level structure as a function of temperature for an n-type extrinsic semiconductor. At 300° K, the donor level population has been depleted sufficiently so that there are a significant number of levels available for population when a basic analyte interacts with the decorated semiconductor interface, contributes electrons to the donor levels, enhances the majority charge carrier concentration, and increases conductance. This process can eventually "top out" the level population.[4] Similarly, an acidic analyte, as it withdraws electrons, and decreases conductance, depletes and can eventually "bottom out" the donor level population. If we deposit nanostructures of $TiO_2$ and $TiO_{2-x}N_x$ to the PS interface these processes can be influenced, directed, and enhanced both by the nanostructure deposition and through optical excitation of the nanostructures. The energy level and density of states structure for $TiO_2$ and its oxynitride have been discussed previously[1,4] as have the onsets for optical pumping.[5-7] The energy levels shift notably on conversion to $TiO_{2-x}N_x$, however, the change in electronic level structure as a function of temperature range in these experiments varies by a very small energy increment[1] as kT is only of the order 208 cm$^{-1}$ (0.025 eV) at 298K and kΔT is a small fraction of this amount.

Results:

FIGS. 1.2(A) and (B) correspond to SEM images which compare the pore structure for the undecorated porous silicon surface and that for the $TiO_2$ decorated pores. The corresponding XPS spectra associated with the TiO$_2$ decorated pores are depicted in FIGS. 1.2(C) and (D).

The responses in FIGS. 1.3 and 1.4 demonstrate results obtained when NH$_3$ interacts with both an untreated and a nano-photocatalyst (TiO$_2$, TiO$_{2-x}$N$_x$) deposited n-type PS interface, 2×5 mm in total dimension (see FIG. 1.1). NH$_3$, as a Brönsted base, donates electrons to the n-type PS interface, increasing the donor electron (FIG. 1.1(D)) majority charge carrier concentration and the conductance as measured by a decreasing resistance. FIG. 1.3 demonstrates the expected decreasing resistance and, as well, indicates that both white light and UV light have no effect on the response of an "untreated" PS interface to NH$_3$. This PS response can be viewed as a backdrop for comparison to the data in FIG. 1.4.

The response to 1-5 and 10 ppm of NH$_3$ for an interface treated with a deposition of "acidic" TiO$_2$ nanostructures, and[3-6] this same interface where the deposited nanostructures are converted in-situ from TiO$_2$ to the more basic TiO$_{2-x}$N$_x$ is compared to that for an untreated PS interface in FIG. 1.4(A). TiO$_2$, a strong (hard) acid, enhances the capture of electrons, and increases conductance (decreases resistance) relative to the undecorated interface. TiO$_{2-x}$N$_x$, once formed, through in-situ treatment of the TiO$_2$ deposited surface, has gained considerable basic character[8] and does not capture electrons as efficiently as does the untreated PS interface. Therefore, the interface conductance decreases. The observed trends are explained within the framework of the Inverse Hard/Soft Acid/Base concept[3,4] which we will briefly outline.

FIG. 1.4(B) indicates the response of a TiO$_2$ nanostructure treated PS interface before and during exposure to both "white light" and UV radiation. Visible radiation has a negligible effect on both the TiO$_2$ treated and the untreated PS interface. When illuminated by UV light, the signal from the TiO$_2$ decorated sensor interface is improved by well over 100%. The UV light source emits radiation whose energy (3.4 eV (365 nm Mercury)) exceeds the 3.2 eV bandgap of anatase TiO$_2$. This process facilitates the transfer of electrons to the decorated PS interface leading to an increase in conductance as TiO$_2$ becomes more acidic on optical excitation and thus attracts electrons more effectively. The exposure of this interface to a 25 Watt "white light" source provides no increase in conductance over that of the TiO$_2$ treated interface. The slight increase in resistance for white light excitation indicates the effect of a slight interface heating (carefully avoided in all additional experiments). The signal observed in the absence of surface heating is identical to that of the untreated PS interface. Optical pumping of the TiO$_2$ decorated interface and the enhancement of interface sensitivity occurs at energies exceeding the TiO$_2$ bandgap.

FIG. 1.4(C) depicts the response of a TiO$_{2-x}$N$_x$ treated interface to UV and white light. Here, the response of the sensor, as manifest by an increase in conductance, is seen to increase by 100+% as a result of UV and "white light" excitation as the electron withdrawing power of the TiO$_{2-x}$N$_x$, which becomes more acidic on excitation, increases. However, this increase occurs for a strong base, NH$_3$, whose contribution of electrons to the n-type semiconductor may be sufficient to "top out" the donor level population.[3,4,9] It is apparent that we have observed the optical pumping of the TiO$_{2-x}$N$_x$ decorated PS interface at energies well into the visible spectral region. The ability to electronically excite TiO$_{2-x}$N$_x$ with visible radiation is consistent with its "effective bandgap" which is of order 2 eV.[1,5-7]

The temperature dependence for an n-type semiconductor (FIG. 1.1(D)), with donor levels just below the conduction band, provides a basis for electron transfer to and from the extrinsic semiconductor. At 0° K, the donar level lies at an energy E$_d$ (≈0.025 eV.)/2 below the conduction band. E$_d$ corresponds to the donor level ionization energy. At moderate temperatures, a major portion of the donor level population has been depleted into the conduction band and the semiconductor reverts to that of an intrinsic material at temperatures above 600 K[10]. The Fermi level has shifted to the energy E$_{Fi}$≈E$_g$/2 where E$_g$ is the intrinsic semiconductor bandgap energy. If an analyte donates electrons to the decorated n-type PS interface and these electrons are not impeded by chemical bond formation, the majority charge carriers will increase within the donor levels and, consequently, the conductance will increase. The addition of electrons to an n-type system can contribute to the eventual saturation of the donor level population. The data in FIGS. 1.4(A) and 1.4(B) demonstrate a saturating effect as the change in resistance decrease[4] as a function of increasing concentration begins to decrease between 3 and 4 ppm.

The responses in FIGS. 1.5 and 1.6 demonstrate results obtained when the moderate Lewis acid, NO$_2$, interacts with and attempts to extract electrons from a TiO$_2$ and TiO$_{2-x}$N$_x$ nanostructure decorated n-type interface. Here, the balance between the electron withdrawing power of NO$_2$ and that of the metal oxide and oxynitride decorated semiconductor interface must be considered. If the electron withdrawing power of NO$_2$ dominates, this analyte depletes electrons from the majority charge carrier concentration, decreases conductance, and increases sensor resistance.[4] However, at a sufficient concentration, the strong acid TiO$_2$ can reverse this process. The mode of interaction and the ultimate sensitivity (ppb) of the interface depends on the relative acid strength of the analyte and that of the fractionally deposited nanostructures.[3,4]

FIG. 1.5 demonstrates the effect of TiO$_2$ fractional nanostructured depositions on the response of the PS interface to NO$_2$. The untreated PS interface (FIG. 1.5(A)) displays a significant increase in resistance as NO$_2$ attracts electrons and depletes majority carriers. FIGS. 1.5(B) corresponds to the response at low TiO$_2$ deposition times (≤10 s), conditions that do not produce sufficient concentrations of nanostructured TiO$_2$ to facilitate its ability to compete with NO$_2$, attracting electrons to the PS interface. The response to NO$_2$, as it extracts electrons, corresponds to a resistance increase (conductance decrease). FIG. 1.5(C) demonstrates the effect that an intermediate TiO$_2$ fractional nanostructured deposition (20 s) has on the response of an n-type PS interface to NO$_2$. The fractionally deposited strong acid, TiO$_2$ now competes effectively with the moderately strong acid, NO$_2$, for the available electrons. At NO$_2$ analyte concentrations in excess of 2 ppm, as the response begins to rapidly increase with the introduction of NO$_2$ (resistance increase), it is suddenly and rapidly quenched. This behavior, associated with the dynamics of electron transduction, is more pronounced at higher analyte concentrations.

As NO$_2$ is introduced to the decorated PS interface and attempts to extract electrons, the resistance rises rapidly to a point where the electron depletion reaches a limiting value. Here, the nanostructured TiO$_2$ islands, coupled to the PS interface, compete with and counteract the extraction of electrons by NO$_2$, preventing further electron withdrawal, and reversing the flow of electrons so as to increase the donor and conduction level electron concentrations. This is manifest by a sharp decrease in the resistance. The effect increases in direct proportion to concentration[9]. The dynamic nature of this interplay is further evident as the resistance drops to a minimum value and then begins to again increase as $NO_2$ is removed. As $NO_2$ is introduced in a new cycle the spike-like increase in resistance is again observed followed again by a sharp drop in resistance. The process of interaction is a dynamic one as $TiO_2$ and $NO_2$ vie for the available electrons.

At higher fractional depositions (FIG. 1.5(D)—30 s deposition time) the $TiO_2$ coupled to the PS interface overcomes the electron withdrawing power of $NO_2$ and the response is that of a system which attracts electrons to the decorated PS interface, leading to a decrease in resistance (increase in conductance).

To obtain the data in FIG. 1.5(E) we have converted the $TiO_2$ nanostructure deposit of FIG. 1.5(D) in-situ to the corresponding oxynitride, $TiO_{2-x}N_x$, diminishing the ability of the deposited nanostructures to attract electrons. At $NO_2$ concentrations ≤5 ppm, the system again responds to the analyte by removing electrons from $NO_2$. This corresponds to a decrease in resistance although the decrease is notably less than that for the $TiO_2$ decorated system (FIG. 1.5(D)). However, an $NO_2$ concentration of 10 ppm is now sufficient to reverse this response, leading to a positive resistance change which results from a dominant electron extraction by $NO_2$. It is against the dynamic changes outlined in FIG. 1.5 that we consider the response upon exposure to visible and ultraviolet light.

The data in FIG. 1.6(A) compares the response of a $TiO_2$ treated n-type PS interface to the responses for this same interface subsequently exposed to UV and "white light" excitation for $NO_2$ concentrations of 1-5 and 10 ppm. This experiment was carried out at a sufficiently low $TiO_2$ concentration so that $NO_2$ dominates $TiO_2$ depleting the majority charge carriers from the extrinsic semiconductor interface[3,4] (FIG. 1.5(B)). The depletion saturates at a concentration of 10 ppm as the resistance increase does not double that at 5 ppm. However, as indicated previously (FIG. 1.5(c)), nanostructured "acidic" $TiO_2$ islands, as hard acids, act to prevent electron withdrawal, increasing the donor and conduction level electron concentrations. Therefore, at sufficiently high $TiO_2$ depositions, the conductance will increase (decreasing resistance). FIG. 1.6(A) demonstrates that at the lower $TiO_2$ depositions, the introduction of "white light" somewhat diminishes the ability of $TiO_2$ to compete with $NO_2$ as indicated by a slight increase in resistance. By contrast, the exposure to UV light creates an interface which competes so effectively for the available electrons that the resistance response decreases and subsequently reverses. This corresponds to a conductance increase (resistance decrease) with analyte concentration as the treated interface extracts electrons from $NO_2$. The effect, apparent with increasing $NO_2$ concentration, is quite pronounced at 10 ppm where one observes a significant signal reversal relative to the $TiO_2$ treated interface that is not exposed to UV radiation. Optical pumping has created a strongly acidic electronically excited $TiO_2^*$ modified interface which is much more efficient at attracting and transferring electrons to the PS interface.

FIG. 1.6(B) depicts the response of a $TiO_{2-x}N_x$ treated PS interface. The conversion to $TiO_{2-x}N_x$ creates a more basic site that does not compete nearly as effectively with the acidic $NO_2$ for electrons. In addition, the more basic $TiO_{2-x}N_x$ fractional deposition contributes electrons more effectively than can $TiO_2$[4,8,11]. When the decorated sensor is exposed to a low level of "white light" its enhanced basicity, which also translates to visible light absorption, results in an enhanced electron transfer from $TiO_{2-x}N_x$ to $NO_2$. The interface resistance response is seen to increase to levels which are well over 100% for the lowest concentrations (1-3 ppm) used in this study. While the response increases linearly with exposure for the lowest concentrations it begins to saturate at concentrations in excess of 3 ppm. At 5 ppm the signal observed with and without white light excitation is virtually identical as the oxynitride surface, at this $NO_2$ analyte concentration, begins to counter electron extraction by $NO_2$. The increased $NO_2$ concentration now induces a more rapid response from the oxynitride decorated interface and a back extraction as the $TiO_{2-x}N_x$ interface no longer allows the extraction of additional electrons even in the presence of "white light" excitation. At a 10 ppm $NO_2$ exposure (FIG. 1.7), the response of the $TiO_{2-x}N_x$ interface at first increases with $NO_2$ electron extraction, however, it begins to decrease with time in comparison to the lower $NO_2$ concentrations as the enhanced ability of $NO_2$ to extract electrons from the decorated oxynitride surface is countered by the far more acidic "white light" excited decorated surface. The more expanded view in FIG. 1.7 demonstrates that the observed dynamic behavior is analogous to the back transfer process depicted in FIG. 1.5(C). Here, as the $NO_2$ is introduced to the sensor interface and the electron extraction process increases rapidly, the response again rises to a resistance response comparable to the peak of the 5 ppm response. The resistance is then seen to decrease as a function of time, indicating the back transfer of electrons to the interface and an increase in conductance as the considerably more acidic $TiO_{2-x}N_x^*$ interface is now more efficiently extracting electrons. As the $NO_2$ concentration is rapidly removed, there is a corresponding spiked increase in resistance. This is a dynamic electron transduction process analogous to those observed in FIG. 1.5(C) but now resulting from the interaction of a strongly acidic $TiO_{2-x}N_x^*$ excited state on the PS interface.

FIG. 1.6(C) depicts the response of an oxynitride treated interface where the $TiO_{2-x}N_x$ is optimized at a considerably higher fractional deposition level analogous to that in FIGS. 1.5(D) and 1.5(E). At concentration levels of 1-5 ppm $NO_2$, this leads to a dominance of the oxynitride. Electrons, extracted from $NO_2$, contribute to the majority charge carrier concentration and a decrease in resistance. However, in an opposite sense to the dynamic behavior observed in FIG. 1.6(B), an $NO_2$ concentration of 10 ppm is sufficient to overcome the $TiO_{2-x}N_x$ decorated interface and the response now corresponds to a resistance increase as $NO_2$ now dominates and majority charge carriers are removed. The introduction of "white light" clearly enhances the electron capturing power of the oxynitride as all of the responses now show a significant decrease in resistance (over 100%) versus the unexposed oxynitride treated surface. Even more striking is the complete reversal of the response for the 10 ppm $NO_2$ exposure. The responses in FIGS. 1.6(B) and (C) clearly demonstrate that "white light" excitation greatly amplifies the sensitivity of the decorated interface. The data demonstrates the manifestation of the optical pumping of the $TiO_{2-x}N_x$ decorated PS interface at energies well into the visible as might be expected from the light response curves indicated in FIG. 1.1. However, the more concentrated oxynitride, while more basic than $TiO_2$, still possesses a sufficient acidic character to overcome the electron withdrawing power of $NO_2$.

We find that, "white light" excitation enhances the response both when $NO_2$ dominates the oxynitride decorated interface and when the decorated interface dominates $NO_2$. In one case, FIG. 1.6(B), the increased signal is manifest by a resistance increase whereas, in the second example, FIG.

1.6(C), by a conductance increase. The effect of optical pumping is to amplify the signal obtained at both regimes of nanostructure modification.

The results presented in FIGS. 1.6(A) and (B) must be considered with respect to the response of $NO_2$ to light as it interacts with the PS interface. FIG. 1.8 demonstrates that the response to $NO_2$, which corresponds to an increased resistance, decreases for both white light and UV excitation as $NO_2$ is extracting electrons at a decreased rate. This decrease is counter to the increase in resistance observed in FIG. 1.6(B) suggesting that the observed increase in resistance in the presence of $TiO_{2-x}N_x$ represents a lower bound. The data in FIG. 1.8 would suggest a decrease in electron extraction by $NO_2$ with optical pumping. However, $NO_2$ in the presence of PS alone still extracts electrons, counter to the data in FIG. 1.6(A) that demonstrates the interface extracts electrons under UV excitation. The optically pumped conversion of $TiO_2$ and $TiO_{2-x}N_x$ to their acidic excited states produces a dominating interface upon UV and visible excitation.

Discussion:

The Inverse Hard and Soft Acid/Base (IHSAB) concept [3,4] allows the minimization of chemical bonding to maximize electron transfer at an extrinsic semiconductor interface. The coupling of analyte/interface acid-base chemistry, provides for a balance between surface electron transduction and chemisorption, and outlines a framework for active metal oxide or metal oxynitride nanostructures to utilize these differences. The semiconductor interface is modified by introducing additional metal oxide "island" sites in fractional deposition. These nanostructures form a superstructure on the semiconductor. The nanostructures focus electron transduction to couple with the majority charge carrier concentration of an extrinsic p- or n-type[3,4] semiconductor and the transfer of electrons to (basic) or from (acidic) analytes. If an analyte donates electrons to an n-type semiconductor, the majority charge carriers, electrons, and the population of the donor levels increase. The dynamics of this process is strongly influenced by the fractional nanostructure coverage of the semiconductor interface. While the increase or decrease in conductance associated with the response to a given analyte is determined predominantly by the p or n-type character of the extrinsic semiconductor interface, the dynamics of conduction[3,4,9] can be modified as a result of the acid/base strength of the fractionally deposited nanostructures. This can be exploited to enhance sensor sensitivity and selectivity. The prepared interfaces are superior to traditional metal oxide systems as they not only operate at room temperature but also can function over a broad range of environments and stable, readily accessible, elevated temperatures.[12] The nanostructure deposition[2,3,4] requires no self-assembly but must be maintained at a sufficiently low level in order to avoid cross-talk between the nanostructures that can lead to a noisy device and the eventual loss of functionality.

The results obtained in this study indicate that the electron transduction dominated interaction of an analyte is strongly influenced by light absorption. The semiconductor interface can be modified through treatment with nanostructured metal oxides, many of which are photocatalysts of varying degrees and levels of acidity. These oxides can also be converted to more basic oxynitrides. This provides a range of materials which, when properly engaged provide a variable enhancement of the response from a given extrinsic semiconductor interface to ensure sensitive and selective directed physisorption that can be enhanced through solar pumping.

The results shown above outline a means for the significant improvement of nanostructure treated environments, where electrical or battery power is at a premium. Here, solar radiation can be used to significantly enhance the sensor response. The average spectral brightness of the sun is its luminance divided by the bandwidth of the sun's visible output, which extends over 300 nm for the visible wavelength region, 400-700 nm. The average spectral brightness of the sun is $L_{v\lambda} \approx 1.5 \times 10^5$ lumens/$cm^2$-steradian/300 nm=500 lumens/$cm^2$-sterad-nm. The light impingent on the sensors leading to the observed responses, obtained from an incandescent light bulb, positioned 10 cm from the sensor interface in the current experiments, corresponds, at most, to a few lumen/$cm^2$-sterad-nm. This light level can easily be obtained with solar radiation. The insertion of a chopper, allowing one to lock onto the impinging radiation, will further improve the signal to noise. While these sensor suites are readily assembled we again caution that a fractional deposition of the $TiO_2$ and $TiO_{2-x}N_x$ is required[3,4,9]. The deposition process should be carefully monitored to avoid over depositing and/or the creation of a surface coating.[3,4] Further, the optical pumping of the surfaces must also be done in a manner which does not lead to significant thermal excitation of the $TiO_2$ and $TiO_{2-x}N_x$ nanostructure treated surface. Both coating, as opposed to fractional deposition, and thermal excitation are found to greatly diminish sensitivity.

Conclusions:

$TiO_2$ nanostructure island sites deposited to a sensor interface can greatly enhance the surface acidity, however, the deposition process must be limited to avoid crosstalk between the nanostructures. The sensitivity to $NH_3$ is greatly enhanced by $TiO_2$ deposition and increases as UV light impingent on the sensor increases the acidic character of $TiO_2$. $NO_2$, as a moderate acid, extracts electrons from a PS interface and treatment with limited concentrations of $TiO_2$ enhances this process. UV light reverses this process, increasing the acidity of the optically pumped $TiO_2$ treated interface which extracts electrons from the moderately acidic $NO_2$. In-situ nitridation of the deposited $TiO_2$ to form the oxynitride, $TiO_{2-x}N_x$, enhances the visible light response, basicity, and sensitivity of the decorated interface. At low fractional oxynitride depositions, $NO_2$ dominates $TiO_{2-x}N_x$ and white light excitation increases sensor response. With higher deposition, white light increases the sensor response in the form of an increased conductance as the $TiO_{2-x}N_x$ decorated interface extracts electrons. With average light intensities less than a few lumens/$cm^2$-sterad-nm, it is possible to enhance responses by up to 150% through interaction with visible (and UV) radiation. These light intensities should be compared to the sun's radiation level, ~500 lumens/$cm^2$-sterad-nm suggesting the possibility of solar pumped sensing.

Experimental:

$TiO_2$ nanoparticle colloidal solutions (anatase phase) were prepared through the controlled hydrolysis of titanium (IV) tetraisopropoxide in water. TEM demonstrates that the nanoparticles range in size from approximately 3 to 11 nm. They are stable for extended periods under refrigeration[5,6]. Active $TiO_{2-x}N_x$ photocatalysts tuned to absorb across the visible spectral region (FIG. 1.1) can be formed, in seconds, from the direct nitridation of the anatase $TiO_2$ nanocolloid solutions with alkyl ammonium compounds[5]. The absorption onset of the catalytically active[5,6] anatase $TiO_{2-x}N_x$ extends well into the visible region at a wavelength of about 550 nm (FIG. 1.1). By comparison, Degussa P25 $TiO_2$ is nitridated over a period of several days at a much lower efficiency[6]. While the $TiO_2$ nanocolloid reflectance spectrum is, as expected, blue shifted relative to the larger (~30 nm) Degussa P25 structures, it is striking that the nitridated $TiO_{2-x}N_x$ nanocolloids display a reflectance spectrum considerably red shifted from that of a Degussa sample. This red shift forms the basis for a "visible light" absorbing[5,6] photocatalyst that can be deposited to an appropriate semiconductor, forming effective electron transducing sites for the passage of electrons from analyte to interface with minimal chemical bond formation.

To create the framework to develop highly efficient light trapping[13] nanostructure modified interfaces on n-type PS, a nanopore coated microporous interface must be generate[2] (FIG. 1.1). The PS interface is generated by electrochemical anodization of 1-20 ohm-cm, n-type (phosphorous doped) (100) silicon wafers (Wafer World). The anodization of the n-type wafers is carried out under topside illumination using a Blak-Ray mercury lamp. After the wafer is etched in a 1:1 solution of HF and ethanol, the prepared n-type anodized sample is placed in methanol for a short period and then transferred to a dilute HF solution for a 30 minute period. This process creates a porous structure with pore diameters of order 0.5-0.7 μm and pore depths varying from 50 to 75 μm[14] (FIG. 1.1). These "light harvesting" interfaces, in combination with $TiO_2$ and $TiO_{2-x}N_x$, provide the means for enhancing the visible and UV response of the interface.

Before anodization, an insulation layer of SiC (≈1000 angstroms) is coated onto the c-Si substrate by PEVCD methods and windows of 2×5 mm are opened in this layer by Reactive Ion Etching (RIE). SiC makes it possible to form the hybrid micro/nanoporous PS structure in the specified windows during electrochemical anodization. Because of its resistance to HF, SiC aids the placement of gold contacts exclusively on the porous layer for resistance measurements and acts as an electrical insulator on the doped silicon. The formation of low resistance gold contacts has been discussed in detail previously[2,3]. The PS hybrid arrays of nanopore covered micropores are tested at room temperature for their individual sensor response. The selection of the nanostructures and the variable surface sensitivities that are produced as they form in-situ metal oxide deposits, introduces a distinct systematics of design, which can be predictably formatted. The approach is unique in that the nanostructures are deposited fractionally to the PS micropores and this fractional deposition does not require any time consuming self-assembly within the pores. This is not a coating technique or one that requires an exacting structural film arrangement but is, in fact, a much simpler process. The untreated PS hybrid structures are exposed to dilute (DI) solutions containing $TiO_2$ for 10 to 30 seconds and are placed in DI $H_2O$ and MeOH for consecutive 120 second periods. The metal oxide is treated in-situ to form the oxynitride. The metal oxide depositions when characterized before deposition have partially transformed to amorphous structures displaying weak diffraction patterns. Therefore, it is difficult to envision their crystallization during the short deposition and subsequent surface cleaning process. After deposition the decorated surfaces are cleaned for 120 s in DI and 120 s in methanol.

In each case, the analyte gas being sensed is brought to the hybrid surface after entrainment at room temperature in UHP nitrogen (Matheson 99.999+%). The system is purged with UHP nitrogen for a minimum of 30 minutes before use. The typical resistances for the base PS structures range between 300 and 5,000 ohms at room temperature. The gas flow for the analyte and the entraining UHP nitrogen is controlled by MKS type 1179A mass flow controllers. The mass flow controllers used to control the analyte gas and the entraining nitrogen flow respond in less than 2 seconds. The diffusion time of the analyte gas to the sensors, which provides the longest system time constant, varies from four to five seconds for the lowest analyte concentrations to of order 1 to 2 seconds for concentrations greater than 2 ppm. These are the delay times for the observation of a signal due to the analyte in the supply line. The sensors respond to the analyte gas on a time scale much less than two seconds. The change in resistance is measured in one-second intervals using a DC current. This voltage bias used in these experiments is 3 volts to obtain an optimum signal to noise ratio. A NI DAQPad-6015 is used for gathering data and supplying the DC current. Labview software is used to control the experiment and record the results. MATLAB is used in the analysis of the data.

REFERENCES

[1] R. Asahi, T. Morikawa, T. Ohwaki, K. Aoki, and Y. Taga, *Science*, 2001, 293, 269. UV radiation: $7.199 per kWh from a Synchrotron ring at 100-200 kW power, Handbook of Laser Technology and Applications, Colin E. Webb and Julian D. C. Jones (2004); Electricity: $0.034 per kWh, "avoidance cost" cited by Entergy Corporation for taking electricity from Green generators of electricity making less than 1 MW of power.

[2] S. Ozdemir, and J. L. Gole, *Current Opinions in Solid State and Materials Science*, 2008, 11, 92.

[3] J. L. Gole, and S, Ozdemir, *Chem Phys Chem.*, 2010, 11, 2573.

[4] J. L. Gole, E. C. Goode, and W. Laminack, *Chem Phys Chem*, 2012 13, 549-561.

[5] J. L. Gole, J. D. Stout, C. Burda, Lou, Y. B.; and Chen, X. B.; *Journal of Physical Chemistry B*, 2004, 108, 1230.

[6] X. B. Chen, Y. B. Lou, A. C. S. Samia, C. Burda, and J. L. Gole; *Advanced Functional Materials*, 2005, 15, 41.

[7] a) H. Irie, Y. Watanabe, K. Hashimoto, *J. Phys. Chem. B* 2003, 107, 5483. b) Sano, T.; Negishi, N.; Koike, K.; Takeuchi, K.; Matsuzawa, S. *J. Mater. Chem.* 2004, 14, 380. c) O. Diwald, T. L. Thompson, E. G. Goralski, S. D. Walck, J. T. Yates Jr, *J. Phys. Chem. B* 2004, 108, 52. d) Torres, G. R.; Lindgren, T.; Lu, J.; Grandqvist, C. G., and Lindquist, S. E.; *J. Phys. Chem. B*, 2004, 108, 5995.

[8] Caitlin Baker, Jeffrey Kenvin, Mark White, and J. L. Gole, to be published.

[9] W. Laminack, N. Pouse, and J. L. Gole, *ECS J. Solid State Sci. Tech.* 2012, 1, Q25-Q34. doi:10.1149/2.002202jss

[10] M. N. Rudden, and J. Wilson, *Elements of Solid State Physics*, John Wiley and Sons editors.

[11] J. L. Gole, W. Laminack, *Bellstein J. of Nanotechnology*, 2013, 4, 20-31.

[12] S. Ozdemir, T. Osburn, and J. L. Gole, *J. Electrochem. Soc.*, 2011 158(7), J201-J207.

[13] A. J. Nozik, *Inorg. Chem.* 2005, 44, 6893; (b) T. Gerfin, M. Graezel and L. Walder, in *Progress in Inorganic Chemistry*, ed. D. K. Kenneth, 2007 pp. 345-393.

[14] C. Levy-Clement, A. Lagoubi, M. and Tomkiewicz, *J. Electrochem. Soc.* 1994 141, 958.

Example 2

Brief Introduction

A unique new approach to sensor design and construction has been conceptualized and initially validated. Implemented in basic science and technology, the Inverse Hard/Soft Acid/Base (IHSAB) model links chemical selectivity to the mechanism of sensor response for both doped semiconductor and nanowire sensors. This IHSAB model provides a simple-to-use prescription for design, which relates rationally and generally the physics and chemistry of specific nanostructure interfaces. The model combines the basic tenants of acid/base chemistry and semiconductor physics so as to form a road map for the implementation of readily constructed, cost effective, rapidly responding, deployable devices, sensitive to the ppb level. The mechanism of selectivity relies on the use of a nanopore coated microchannel array, which combines optimized analyte diffusion with maximum interface interaction. The nanoporous coating of the microchannel provides a unique phase match for the subsequent fractional deposition of select nanostructure islands that decorate the microchannel. The materials selected for the nanostructured islands serve the role of guiding antennas to force a dominantly physisorbtive (vs. chemisorbtive) interaction at the decorated extrinsic semiconductor interface. The process can be reversed for microreactor applications. The selection of these nanostructures and the variable and controllable physisorbed (reversible) interaction they introduce for sensor applications, is well predicted by the IHSAB model. The IHSAB model the coupling of analyte/interface acid-base interactions with the properties of the majority carriers in an extrinsic semiconductor. The approach is unique in that the nanostructures are deposited fractionally to semiconductor micropores; this fractional deposition DOES NOT require any time consuming self-assembly within the pores and is far simpler to implement than traditional thin film or alternate coating techniques. The selection of the nanostructures that are deposited to the nanopore covered microchannels and the variable surface sensitivities that are produced, as they form in-situ metal/metal oxide deposits, can now be predicted not in a random fashion or based on limited previous observations, but in a clearly designed procedure based on established molecular properties.

Introduction—the IHSAB Model for Porous Silicon Sensors and Microreactors

Despite significant effort, much of the basic science and technology that can provide a general means to link sensor and micro-reactor design, in a framework applicable to detect and transform gas phase analytes and analytes in aqueous solution, has not yet been developed. In this chapter we will outline a novel, rational, and general approach to generate efficient interfaces which are being designed to detect, sequester, and destroy harmful analytes. At the heart of the conceptual approach is the combination of the basic tenants of acid/base chemistry and semiconductor physics This structured approach can be demonstrated to be relatively simple to follow and implement, leading to the future likelihood of cost effective, deployable devices sensitive to the ppb level. This can provide systems operating in an unsaturated mode over a wide temperature and pressure range, complemented by pulsed mode operation, which ensures low energy consumption and high analyte selectivity. The defining constraints offered by the combination of acid/base and semiconductor theory can enable the selection of device materials which target specific gas analytes. The degree to which this combination allows the tailoring of interfaces, through an understanding of their physics and chemistry, offers the means to construct a framework for analyte sensing and transformation. Further, the extension of this concept for sensor and microreactor development, on appropriate extrinsic semiconductor interfaces, might be coupled with solar energy conversion to enhance the potential for combining conductometric sensor suites and active photocatalysts, with application to the development of solar pumped sensing.

The enhanced activity of nanoscale structures can have a profound effect on the development and mediation of MEMS/NEMS sensing/microreactor technology, providing new inroads to create hybrid devices with greatly enhanced sensitivity, selectivity, and chemical transformation efficiency. Within this framework, we consider a new approach to the formation of optimal sensor interfaces and arrays and transducing interfaces that can function across a broad temperature and pressure range (Seals et al. 2002; Lewis et al. 2005, 2007; Gole and Ozdemir 2010). The method of sensor design shows the potential to replace traditional metal oxide sensor systems (usually $SnO_2$-based), especially in elevated temperature environments. Also inherent to this approach is the developing general concept of nanostructure directed physisorption (electron transduction) versus chemisorption at a doped semiconductor interface. Coupling the trends in the acid/base character of an analyte and an extrinsic semiconductor interface with the inherent nature of majority charge carriers in p and n-type semiconductors affords the potential to design a sensitive and controllable means of transferring electrons to build distinct sensor matrix arrays or modify in a controlled manner chemical transformations at an interface. In complement, the modification of this approach to sensor design to produce strong chemical interactions and dominant chemisorptions, has potential broader implications for microreactor technology including the sequestering and destruction of contaminants. The coupling of acid/base and semiconductor technology facilitates analyte-semiconductor interactions. This promotes enhanced sensor and microreactor capability and an enhanced combined microstructure-directed nanostructure conversion capability via the action of modifying nanostructures as they are introduced to a nanopore covered microporous semiconductor interface (Gole and Ozdemir 2010; Gole et al. 2011).

The Inverse Hard/Soft Acid/Base (IHSAB) principle/approach, as it correlates with a basis in physisorption (electron transduction), complements the HSAB principle for hard/soft acid/base interactions first put forth by Pearson (1963, 1990, 1997, 2005) and later correlated with density functional theory (DFT) (Parr et al. 1978; Yang et al. 1984; Yang and Parr 1985; Parr and Yang 1989; Geerlings et al. 2003) and Chemical Reaction Theory by Parr and Pearson (1983), Cohen and Wasserman (2007), and others (Zhan et al. 2003). The basis for correlation follows the principle that soft-soft acid/base interactions produce significant covalent bonding and hard-hard combinations produce significant ionic bonding. The HSAB principle states that hard acids prefer to coordinate to hard bases and soft acids prefer to coordinate to soft bases. In contrast, the driving principle to promote physisorption (electron transduction) represents the inverse of that necessary to form strong chemical bonds (Gole et al. 2011; Gole and Ozdemir 2010). This principle is manifest through the interactions of metal oxide nanostructures as they influence the nature of the majority carriers in a p- or n-type semiconductor. Nanoporous silicon layers positioned on porous silicon (PS) micropores facilitate the deposition of nanostructured metal/metal oxides which provide distinctly higher variable sensitivities and selectivity for a given extrinsic semiconductor interface. It is necessary that one treat the PS surface with fractional depositions, much less than a monolayer to insure that the nanostructures do not begin to cross talk and, in so doing diminish signal to noise. This deposition can be made to produce a dominant physisorptive (sensors) or chemisorptive (micro-reactors) character at the semiconductor interface as the deposited nanostructures act to focus the nature of the surface interaction. However, the nature of the extrinsic semiconductor, the manner in which its donor and/or acceptor levels can be manipulated, and its transformation to intrinsic character also represent important variables.

The dynamic natures of "n" and "p-type" silicon extrinsic semiconductors must be evaluated and compared, focusing on the controlled manipulation of these semiconductors as they are modified with nanostructures and interact with gaseous or aqueous analytes. The observed semiconductor responses correlate well with the temperature dependence of an extrinsic semiconductor as it is manipulated in the transformation to intrinsic character. This is intimately tied to the population of donor or acceptor levels, and the inherent mobilities of electrons. When considering the inherent mobilities of electrons and holes, it is not surprising that the response of modified n-type semiconductors is found to exceed that of comparable p-type systems. The IHSAB concept can be extended to address the properties of several additional semiconductor interfaces including nanowires. The results obtained not only pertain to sensor and micro-reactor array design but also suggest the importance of the dynamic changes created as the majority charge carrier concentrations of the interacting extrinsic semiconductors are manipulated and their Fermi energies are modified through chemical and light interaction.

The Interface on Extrinsic Semiconductors

The widespread use of interfaces for chemical sensors and reactive transduction, including that introduced by catalysis, is a function of stability, speed, ease of manufacture, ease of calibration, and ease of use. Recently Korotchenkov and Chou (2010) have discussed these requirements and the advantages of porous silicon (PS). It is a crystalline material of large interfacial surface area, which is microelectronics (CMOS) compatible and can be simply fabricated with inexpensive equipment. However, with this simple mode of fabrication, it has been necessary to overcome problems of stability and reproducibility by applying several new fabrication and testing methods (Kottke et al. 2009; Ozdemir and Gole 2010a; Korotcenkov and Cho 2010). When this is done, it is possible to generate devices with continued improvements in sensitivity, which can operate for several months and be readily rejuvenated.

Porous silicon (PS) nano/microporous interfaces, illustrated in FIGS. 2.1 and 2.2, are produced by a simple hybrid etch procedure described in detail elsewhere (Levy-Clement et al. 1994; Foell et al. 2002; Ozdemir and Gole 2008a) creating the desired interfacial support structure. The format for design and fabrication is applicable to virtually any extrinsic semiconductor into which a nanopore coated microporous framework can be generated.

The silicon structure or layers and the porous silicon (PS) structures, devices, and methods, can be replaced with any alternate extrinsic semiconductor (e.g., GaP, InP, CdTe) onto which a porous microstructure can be generated. Further, the configuration in FIG. 2.1 can be adapted to form a pass-through microporous membrane (Campbell et al. 2008; Gole et al. 2009). This greatly broadens the range of nanostructure-interface combinations that can be potentially exploited, as the alternate extrinsic semiconductors can be a p-type, a $p^+$-type, a n-type, or a $n^+$-type substrate.

A nanoporous (shown in green) coated micropore array (FIG. 2.1) with micropores ideally 1-1.5 microns in diameter. The arrays from p, n, $p^+$, and $n^+$ extrinsic semiconductor substrates are fabricated using a variety of anodization techniques discussed in detail elsewhere (Levy-Clement et al. 1994; Foell et al. 2002; Ozdemir and Gole 2008a). Before anodization, a silicon wafer is cleaned in HF (49%) and a SiC layer 1000 angstroms in thickness is coated onto the polished surface of the silicon wafer by Plasma Enhanced Chemical Vapor Deposition (PECVD). SiC is used since this layer is highly durable in HF-based solutions (Nassiopoulos 1997). 2 mm×5 mm windows were opened in the SiC layer by Reactive Ion Etching (RIE). After the anodization process, a gold layer (3500-5000° A) is coated onto the sensor by an e-beam evaporation method. These processes create the overall sensor depicted in FIG. 2.3. The conductometric PS gas sensors typically operate in the 1-5 V range, but it is possible to use the sensors with a 100 mV or smaller bias voltage (Seals et al. 2002; Lewis et al. 2005).

The nanoporous coating process (FIG. 2.1) provides a phase matching for the subsequent deposition of selected nanostructured islands (FIG. 2.1, FIG. 2.2). These surface-attached nanoparticles possess unique size dependent and electronic structural properties that form a basis for extrinsic silicon, measured by circuitry (ex: microprobes as in FIGS. 2.3 and 2.4) attached to the electrodes shown in FIGS. 2.1 and 2.3 as gold contacts (Ozdemir and Gole 2010a). The nanopore covered microporous structure of the interface has been created specifically to facilitate highly efficient gaseous diffusion (Fickian) to the highly active nanostructure (FIG. 2.1) modified nanoporous (FIG. 2.1) coating (Ozdemir and Gole 2010b). While the room temperature operation of this interface serves many applications, the appropriate installation on heat sinks can allow operation at several hundred degrees C. This provides a key element whereby the developed interface can operate under conditions which are not amenable to typical metal oxide systems. Further, when coated with nanoparticle photo-catalysts, the interface can operate as a nanostructure-modified microreactor for efficient chemical transformations.

The approach to interface development in PS sensors also follows a basic concept that is elucidated in a distinct systematics of design. The selection of the nanostructures and the variable surface sensitivities that are produced as they form in-situ metal oxide deposits are predictable (Gole et al. 2011; Gole and Ozdemir 2010). The chemical concepts of acids and bases are coupled with the extrinsic properties of a semiconductor support structure to provide an ordered approach to the generation of an activity matrix for a given analyte gas. The nanopore coated micropores can be treated with a wide array of selective nanostructures (metals, metal oxides, or catalysts-FIG. 2.1) deposited into the microporous channels. This process can be made to create a selective environment for either the physisorption (electron transduction) or the chemisorption of an analyte by correctly correlating the acidic or basic character of the nanostructure modified interface with the acid/base characteristics of the analyte of interest. Further, the degree of physisorption (electron transduction) vs. chemisorption can be varied to create a matrix (array) of responses for a sensor (physisorption (electron transduction) dominated) or a variable degree of chemical activity to produce chemical transformation (chemisorption dominated). Acidic analytes act to withdraw electrons from the nanostructure modified semiconductor interface whereas basic analytes act to donate electrons. As the nanostructure islands are chosen to force degrees of physisorption (electron transduction) they also act as antennas, to increase the sensor sensitivity. The nano-size of these deposits provides for high sensitivities that vary as a function of nanostructure, creating the framework for selectivity.

In the physisorption (electron transduction) dominated mode, amenable to the formation of a reversible sensor response, the transfer to or removal of an electron from the semiconductor surface produces an interaction with the majority charge carriers of the semiconductor which greatly increases or decreases the resistance of a nanostructure modified PS interface (Gole et al. 2011; Gole and Ozdemir 2010). The response will depend both on whether the analyte is an acid or a base and whether the semiconductor is "p-type" or "n-type."

The IHSAB Concept as the Basis for Nanostructure-Directed Physisorption (Electron Transduction) at Sensor Interfaces The concept of chemical hardness/softness first developed by Pearson (Gole et al. 2011) is based on the nature of metal ion complexation in aqueous solution and is a generalization of the Lewis acid/base concept. The HSAB concept, as it is correlated with chemical reactivity theory (CRT), was given a deep foundation in terms of density function theory by Parr and coworkers (Parr et al. 1978; Yang et al. 1984; Yang and Parr 1985; Parr and Yang 1989; Geerlings et al. 2003), following an initial correlation with molecular properties established by Pearson (1963, 1988, 1990, 1997, 2005). More recently, conflicts underlying the correlation of the DFT and CRT theories have been largely resolved by Cohen and Wasserman (2007) to obtain a further refinement of the concepts of electronegativity and hardness.

The properties of acids and bases can be described as hard and soft based upon the correlation of several atomic/molecular properties which include the ionization potential, I, the electron affinity, A, and the chemical potential, $\mu$, in connection with the HOMO-LUMO gap concept from molecular orbital (MO) theory as the Kohn-Sham orbitals replace the MOs (Parr and Yang 1989; Geerlings et al. 2003; Yang et al. 1984; Parr et al. 1978; Yang and Parr 1985).

Examples in terms of the groups of hard, borderline, and soft acids and bases are given in Table 2/1 (Pearson 1988). For a soft acid, the acceptor atom is of low positive charge, large size, and has easily polarizable outer electrons. The acceptor atom of a hard acid is of small size and not easily polarized. In a soft base, in precise contrast to a hard base, the donor atom is of low electronegativity, easily oxidized and highly polarizable with low-lying empty molecular orbitals. The HSAB principle was initially based on empirical observations. However, as it groups acids and bases, the HSAB basis has been developed in terms of DFT. The basis follows the principle that soft-soft combinations depend mainly on covalent bonding and hard-hard combinations depend mainly on ionic bonding. Further the HSAB principle states that hard acids prefer to coordinate to hard basis whereas soft acids prefer to coordinate to soft bases (Gole et al. 2011).

Within the HSAB-DFT framework, the electronic chemical potential (Pearson 1963, 1990, 1997, 2005; Parr and Yang 1989; Geerlings et al. 2003; Yang et al. 1984; Parr et al. 1978; Yang and Parr 1985; Zhan et al. 2003) given by Equation (3.1), $$\mu = \left(\frac{\partial E(N)}{\partial N}\right)_{v_e} = \left(\frac{\delta E}{\delta \rho}\right)_{v_e} \quad (3.1)$$

is a global quantity. Here E(N) is the ground state energy of a system of N electrons in the electrostatic potential energy, $v_e$, due to its nuclei (fixed) and E is a functional (Eq. (3.1)) of the electron density, $\rho$. The three point finite difference approximation for $\partial E(N)/\partial N$ gives $\mu \approx -(I+A)/2$ with I the ionization potential and A the electronegativity so that $\mu$ is the negative of the Mulliken electronegativity $\chi_M$ (Equation (2)):

$$\chi_M \approx -\mu \approx \frac{(I+A)}{2} \quad (3.2)$$

The absolute hardness of a species, $\eta$ (Pearson 1963, 1988, 1990, 1997, 2005; Parr et al. 1978; Yang et al. 1984; Yang and Parr 1985; Parr and Yang 1989; Geerlings et al. 2003; Zhan et al. 2003), is defined by Eq. (3.3):

$$\eta = \left(\frac{\partial^2 E(n)}{\partial N^2}\right)_{v_e} = \left(\frac{\partial \mu}{\partial N}\right)_{v_e} \approx (I-A) \quad (3.3)$$

and the absolute softness (Yang and Parr 1985) is the inverse of the hardness (Eq. (3.4)):

$$S = \eta^{-1} = \left(\frac{\partial N}{\partial \mu}\right)_{v_e} \quad (3.4)$$

The approximation in Eq. (3.3) arises from the use of the finite difference formula.

Unlike the chemical potential, the hardness is not constrained to be constant everywhere throughout a system, having local values for which $\eta$ is simply a global average. Parr and coworkers (Parr and Yang 1989; Geerlings et al. 2003; Yang et al. 1984; Parr et al. 1978; Yang and Parr 1985) have defined a local hardness that corresponds to the change in chemical potential with electron density in different parts of a molecule, complex or simply a system. Cohen and Wasserman (2007), in their formulation of CRT, define a generalization to include a hardness matrix that incorporates both the self-hardness of individual species and the mutual hardness for pairs of species combining in a system. They also provide a description of local softness as they demonstrate how the reactivity of a species depends on its chemical context. Within this context, as interacting constituents separate, the hardness matrix becomes diagonal in the self-hardness. It is possible to establish a more general description of electronegativity (Eq. 2) equalization. Cohen and Wasserman's (2007) generalization realizes that reactivity indices are chemical-content dependent, not unique properties of an isolated system as an electron can move on and off of a species, interacting with its chemical environment. The electron need be associated with that species only part of the time as, for example, when a Lewis acid/Lewis base interaction takes place. Of equal importance are the correlations which define the connection between CRT and DFT theories as they can be used to provide a description of those molecular orbitals (MO's) involved in the process of electron transfer from an acid to a base.

Within the context outlined, if two systems B and C are brought together, electrons will flow from the system of lower $\chi$ (Eq. (3.2)) to that of higher $\chi$ to equilibrate the chemical potentials. If we consider that in solid-solid interactions, the equilibration of the Fermi levels is the analog of the chemical potential, it is not difficult to envision the extrapolation of these concepts to the interaction of a molecule with an interface.

Within the context of interacting molecular systems B and C, as a first approximation to an acid-base interaction, the fractional number of electrons transferred can be defined by Gole et al. (2011)

$$\Delta N = \frac{\chi_C - \chi_B}{2(\eta_C + \eta_B)} \quad (3.5)$$

where the difference in electronegativity drives the electron transfer and the sum of the hardness parameters acts as a resistance. This expression, while approximate, is useful because it expresses the nature of the initial interaction between B and C using properties of the isolated systems providing the backdrop for the first order categorizations given in Table 2/1. Whereas the absolute chemical potential and hardness are molecular parameters, the flow of electrons is from a specific occupied molecular orbital of B to a specific empty orbital in C so that the overlap between the exchanging orbitals will be critical in determining energy change and the nature of chemical interaction.

The correlation of hardness and softness with molecular orbital theory follows readily from the Frontier orbital concept of chemical reactivity theory (Fukui et al. 1952). Within the context of Koopman's theorem, the frontier orbital energies can be correlated with the expressions for chemical potential (Eqs. (3.1) and (3.2)), hardness (Eq. (3.3)), and softness (Eq. (3.4)) as $$-\epsilon_{HOMO} = I, \quad -\epsilon_{LUMO} = A \quad (3.6)$$

where now the concept of hardness reduces to the statement: hard molecules have a large HOMO-LUMO gap and soft molecules have a small HOMO-LUMO gap (Pearson 1988). This concept must be carefully applied. In formal DFT, the location to which the electron transits corresponding to the electron affinity is not the LUMO but actually the first excited state. In practice, the application of the concept in this manner usually applies, but it is not formally rigorous (Dixon 2010). A further issue in MO theory is that for an infinite basis set, if the EA is negative, the HOMO-LUMO gap is equal to the IP. This means that the outlined concept must be applied carefully to systems that do not have a positive EA and bind an electron (Dixon 2010). The criteria that hard acids prefer to coordinate to hard bases and soft acids to soft bases is, in one sense, a HOMO-LUMO matching criteria. Politzer (1987) has shown that the softness of atoms correlates with their polarizability whereas Huheey (1978) has shown that softness is the ability to accept charge. Within this framework, we promote a HOMO-LUMO mismatch to induce physisorption (electron transduction).

The foundation of the HSAB concept can be used in complement to create a framework for chemisorptive interactions and the formation of a micro-reactor interface. In contrast, to create sensitive, rapidly responding, and reversible PS gas sensors, processes that lead to strong ionic or covalent bonding must be avoided. The following sections of this monograph emphasize that a general approach to conductometric chemical sensor development should follow the inverse of the HSAB concept of acid-base chemical interaction. The changes in response to nanoparticle modified PS interfaces outlined in the following discussion can be correlated with this inverse (IHSAB) behavior.

The Extrinsic Semiconductor Framework

The position of the Fermi level varies with temperature for n-type and p-type semiconductors as shown in FIG. 2.5 (Rudden and Wilson 1993). This temperature dependence forms a basis for our considerations of electron transfer to and from an extrinsic semiconductor the nature of the interaction with majority carriers in that semiconductor, and the corresponding influence that this transfer has on the semiconductor conductance and transduction (Gole et al. 2011). For an n-type semiconductor, donor electron levels lie just below the conduction band (FIG. 2.5A). At 0° K, the Fermi level lies at an energy $E_d$ ($\approx 0.025$ eV.)/2 below the conduction band. Here $E_d$ corresponds to the donor level ionization energy for an n-type system. At moderate temperatures, the vast majority of donor level electrons have been excited into the conduction band as eventually the semiconductor almost reverts to that of an intrinsic material at temperatures above 600 K. At this point, the Fermi level has shifted to the energy $E_{Fi} \approx E_g/2$ where $E_g$ is the intrinsic semiconductor bandgap energy. A similar situation holds for a p-type semiconductor (FIG. 2.5B) as electrons are excited to acceptor levels (holes are excited into the valence band) at an energy $E_a \approx 0.036$ eV (Rudden and Wilson 1993) above the valence band. At 0° K, the Fermi level lies at an energy $E_a/2$ above the valence band, however, FIG. 2.5B depicts the corresponding shift of $E_{Fp}$ as it transcends with temperature to the value $E_{Fi} \approx E_g/2$ for the corresponding intrinsic semiconductor.

A basic analyte can donate electrons to a "p-type" porous silicon (PS) semiconductor surface and these electrons can fill empty acceptor levels or combine with holes. This reduces the number and the formation of majority charge carriers, leading to an increased resistance. The process is effectively reversed for an "n-type" semiconductor as the majority charge carriers, electrons, increase within the donor levels that are not populated at room temperature, and therefore the conductance increases and the resistance decreases. The opposite effect should be observed for an acidic analyte as it withdraws electrons. From the temperature dependent behavior depicted in FIG. 2.5, it is apparent that vacant donor level sites and valence band hole sites increase with temperature. It is also apparent that the addition of electrons to an n-type system should contribute to and eventually "top-out" the donor level population, whereas the removal of electrons and increase in resistance is very much analogous to the effect of temperature rise. In contrast, the removal of electrons from a p-type system can potentially maximize conductance (decrease resistance to a minimum value), whereas an influx of electrons is very much analogous to the effect of temperature rise. These effects, resulting from analyte interface interactions, the preparation of the interface, and the population of donor and/or acceptor levels, have now been clearly observed for several of the sensor systems we consider. Further, the Fermi level shifts that accompany these dynamic interactions are significant. They must also be considered if one is to correctly evaluate solar pumping experiments.

If the extrinsic semiconductor interface is now modified by introducing additional metal oxide "island" sites (FIG. 2.1) in fractional deposition, these nanostructures form a superstructure on the semiconductor interface. These nanostructures act as antennas to influence the transit of electrons to and from the semiconductor interface on which they are deposited and the available donor and acceptor levels.

In a p-type porous silicon (PS), semiconductor surface electrons are being excited from a valence band either into acceptor levels or the conduction band as holes. These represent the majority charge carriers that are created in the valence band. If an analyte donates electrons to a p-type semiconductor, these electrons can combine with holes, thus reducing the number of majority charge carriers, leading to an increased resistance. To first order, the process should be reversed for an n-type semiconductor as the majority charge carriers, electrons, increase the population of the donor levels. If an analyte donates electrons the conductance increases, and the resistance, is expected to decrease. However, the process is more complex, in part, because the majority charge carriers, now electrons, have higher mobilities. The dynamics of these charge carriers can be influenced by the fractional nanostructure coverage of the semiconductor interface. While the increase or decrease in resistance (decrease or increase in conductance) associated with the response to a given analyte is determined predominantly by the p or n-type character of the selectively nanostructure modified semiconductor interface, the dynamics of conduction (Laminack et al. 2012) can be modified as a result of the acid/base strength of the fractionally deposited nanostructures.

Following the framework of the IHSAB concept (Gole and Ozdemir 2010; Gole et al. 2011), selected nanostructured islands (FIG. 2.1), are placed on the semiconductor to act as antennas to promote physisorption (electron transduction). The HSAB principle manifest at surfaces (Parr and Yang 1989; Geerlings et al. 2003; Gole and Ozdemir 2010; Yang et al. 1984; Parr et al. 1978; Yang and Parr 1985 Pearson 1963, 1990, 1997, 2005; Gole et al. 2011), promotes chemisorption. These two principles can be applied in complement to the behavior of an extrinsic semiconductor to provide a range of responses. Thus, a matrix of signatures for a given analyte in a physisorption (electron transduction) dominated sensor mode or, with appropriate modification, a range of reactions in a microreactor configuration might be developed.

Physisorption (Electron Transduction) and the Response of a Nanostructure Modified Sensor Platform The introduction of nanostructures to the nanopore coated microporous framework can selectively modify the resistance response of the PS interface. The selection of the nanostructures that are deposited to the nanopore covered microchannels and the variable surface sensitivities that are produced, as they form in-situ metal/metal oxide deposits, can be predicted in a clearly designed implementation of the outlined concepts above. These predictions are based on established molecular properties, as the chemical concepts of acids and bases are coupled with the extrinsic properties of a semiconductor support structure. As the nanopore coated micropores of a p- or n-type PS surface (hybrid PS) are treated with a wide array of selective nanostructures deposited into the microporous channels, they create a selective environment for either the physisorption (electron transduction) or the chemisorption of an analyte by correctly correlating the acidic or basic character of the nanostructure modified interface with the acid/base characteristics of the analyte of interest. Physisorption (electron transduction) can be made to dominate chemisorption by applying the IHSAB principle and can be varied to create a matrix (array) of sensing responses. Alternatively, the HSAB concept applied to a semiconductor surface might be used to create a variable degree of chemical activity (chemisorption dominated).

Basic analytes contribute electrons whereas acidic electrolytes act to withdraw electrons from the nanostructure modified semiconductor interface. When chosen to force degrees of physisorption (electron transduction), the nanostructured metal oxide islands also act as antennas to increase the sensor sensitivity. In this physisorption (electron transduction) dominated mode, amenable to the formation of a reversible sensor response, the transfer to or removal of an electron from the semiconductor surface results in a modification of the semiconductor majority charge carriers, which greatly increases or decreases the resistance response of the modified PS interface. As we have noted, this will depend both on whether the analyte is an acid or a base and whether the semiconductor is p-type or n-type.

Lewis acids accept electrons and Lewis bases donate electrons. They can be classified in a range from hard to soft where these categorizations are a function of several properties including the electron affinity and ionization potential (Gole, et al. 2011). Hard acids react with hard bases to form strong ionic bonds and soft acids react with soft bases to form strong covalent bonds (HSAB concept (Pearson 1963, 1990, 1997, 2005; Parr and Yang 1989; Geerlings et al. 2003; Yang et al. 1984; Parr et al. 1978; Yang and Parr 1985; Zhan et al. 2003; Cohen and Wasserman 2007; Parr and Pearson 1983)) accompanied by a strong matchup of molecular orbitals (MO's). In a gas-surface interaction this produces strong chemisorption. The IHSAB concept is based on the reversible interaction of hard-acid surfaces with analytes that represent soft bases or hard-base surfaces with analytes that represent soft acids. It requires the combination of a modified semiconductor interface and analyte materials which can be used to direct a strongly dominant electron transduction (vs. chemisorption) interaction (avoiding the formation of a strong bond which inhibits reversibility). For example, as demonstrated in FIG. 2.6, the fractional in-situ nanostructure deposition of $SnO_2$, a strong acid, to a p-type PS interface leads to a maximum impedance increase for the weak base NO. In contrast, a weak acid, $Au_xO$ ($x \gg 1$), nanostructure deposition leads to a maximum impedance increase for the strong bases $NH_3$ and $PH_3$ (FIG. 2.7). The corresponding impedance change for an acidic analyte on the modified p-type PS interface decreases, exemplified for the moderate acid $NO_2$ in FIG. 2.8. These impedance changes are easily measured, show significant variation and are reproducible. Importantly, the increase or decrease in impedance is dictated predominantly by the nature of the semiconductor interface, especially for p-type systems. The data for the gas phase bases in Table 2/2 correspond to comparisons of the positive resistance change produced as $SnO_x$, NiO, $Cu_xO$, and $Au_xO$ ($x \gg 1$) fractional nanostructure deposits are used to modify an untreated PS interface. FIG. 2.9 demonstrates that the nature of these deposits have been verified by XPS spectroscopy. Here, the magnitude of the response changes observed relative to an untreated PS interface forms the basis for the materials positioning diagram in FIG. 2.10.

To first order, the interactions are reversed for an "n-type" semiconductor where the majority charge carriers, electrons, can be made to increase upon "physisorbed" interaction with a basic analyte (conductivity increases as resistance decreases) and decrease upon interaction with an acidic analyte. However, the increased mobility of donor level electrons, in contrast to holes, is also manifest as is the effect of the fractionally deposited nanostructured oxides. Table C (FIG. 2.25) compares and contrasts the details of analyte interaction on primarily n-type PS for the strong base $NH_3$, the amphoteric NO radical, and the moderate acid $NO_2$. The n-type PS interface is treated with fractional nanostructured depositions of nanostructured oxides including $TiO_2$, $SnO_x$, NiO, $Cu_xO$, and $Au_xO$ (Gole et al. 2011). The data in Table C (FIG. 2.25) should be compared with the results obtained for the fractional deposition of nanostructures on a p-type PS interface (B (FIG. 2.25)). This comparison indicates that there are clear and significant differences between the n- and p-type systems. However, at the same time, there is an underlying complementary structure created by the nanostructure deposits.

The concentration of $SnO_x$ and $Au_xO$ nanostructures deposited to the PS interface to produce the enhanced sensitivities relative to PS indicated in FIG. 2.6, is notably less than the nanostructure deposition illustrated in FIG. 2.2. It is necessary that the deposited nanostructures be sparsely interspersed onto the micro/nanoporous framework to avoid crosstalk. Table B (FIG. 2.25) as it summarizes the results for several nanostructure modified p-type PS surfaces for the gases $NH_3$, $PH_3$, and NO at one ppm level, indicates significant differences for the ratios of resistance change given for the various nanostructure deposited interfaces relative to an untreated PS structure. In addition, the data (FIG. 2.6) obtained for CO, a weak base, demonstrates a significant response increase upon exposure of this gas to an $SnO_2$ (hard acid, Table 2/1) nanostructure coated surface whereas the data obtained for $H_2S$ (Gole et al. 2004) (an intermediate base, Table A (FIG. 2.25)) indicates a significant increase in response (1.5-2) for an $Au_xO$ nanostructured oxide (weak acid) deposited interface. The $SnO_x$ deposited sensors, in particular, allow the room temperature detection of CO at the sub-ppm level notably below the sensitivity of other PS sensors (Foucaran et al. 1997; Moseley 1997; Schechter et al. 1995). This $SnO_2$ deposited sensor can be compared with PS-based sensors whose resistances exceed hundreds of kΩ operating on a 2 V bias (Foucaran et al. 1997), $SnO_2$ sensors operating at 300° C.-500° C. (Moseley 1997) and similar gas sensors operating at 2-5 V (Schechter et al. 1995). The data obtained for $SO_2$ (Table B (FIG. 2.25)) demonstrate that this radical acts like a moderate base in the absence of a hydrating environment.

The basic hybrid PS sensor micro/nanoporous surface has been considerably improved through the refinement of etch techniques. With this improvement, electroless gold treatments of the improved PS interface have led to a substantial increase in sensitivity (signal/noise) for ammonia (Ozdemir and Gole 2008b) so that responses in the several hundred ohm/ppm range are possible. This forms the basis for low ppb concentration detection at sensitivity ratios relative to untreated PS as indicated in Table B. The relative sensitivity ratios in Table B and C are maintained quite closely over time and as detection sensitivity is improved. The results obtained for phosphine, exemplified in FIG. 2.7 and summarized in Table B, are difficult to obtain as $PH_3$ is known to display an even greater degree of interaction with a nanostructured surface and have a higher sticking coefficient than $NH_3$ (Lewis et al. 2005; Ozdemir and Gole 2010a). The tendency toward the equilibration of adsorption and desorption, also manifest in ammonia, can produce a gradual increase in the sensor baseline. Although we operate the sensors in an unsaturated mode (Lewis et al. 2005; Ozdemir and Gole 2010a), the sensor response and recovery time scales are distinctly different. The observed drift can also result from weak chemisorptions of $PH_3$ superimposed on a dominant physisorption (electron transduction) (Ozdemir and Gole 2010a). Purging the sensor surface with ultrahigh purity (UHP) nitrogen for longer durations, following exposure to the 300 s $PH_3$ gas pulse (FIG. 2.7), enhances the return to the initial baseline (Gole and Ozdemir 2010; Lewis et al. 2005; Ozdemir and Gole 2010a). This return to baseline can be further improved by more tightly constraining the gas flow path to the sensor surface from its current design for operation at atmospheric pressure. In addition, the application of FFT pulsing techniques, considered in a following section, can be used to average out the effects of this baseline drift (Lewis et al. 2007).

FIGS. 2.6 and 2.7 and Table B suggest that the proper combination of nanocoating techniques could be used to produce combinations of array-based multiple sensor devices of varying sensitivity to a variety of basic gases. The matrix of array responses could be correlated to selectively analyze gas mixtures. For example, a sensor array consisting of an untreated $SnO_x$ nanostructure coated and gold clustered oxide nanostructure coated sensor can be used to sensitively test for the presence and relative concentrations of ammonia and nitric oxide (current limits NO<500 ppb, $NH_3$<50 ppb). A nanostructured $PS/SnO_2/Au_xO$ sensor combination could provide the basis for developing a sensitive room temperature detector that could be installed as a simple sensor system for asthmatics (Lewis et al. 2005; Gole and Ozdemir 2010) where one requires the ability to simultaneously monitor the increase in NO, $NH_3$, and $NO_2$.

Table C has summarized data for several nanostructure modified n-type PS interfaces. $NO_2$ represents a moderate acid (Ervin et al. 1988) whereas $NH_3$ corresponds to a strong base (Grant et al. 2009). We expect these analytes to induce the opposite response from an n-type and p-type semiconductor interface. NO, however, is an amphoteric free radical (Travers et al. 1989) and, for this reason, its interactions are far less straightforward. In FIG. 2.11, we summarize the response changes for an untreated n-type PS interface to $NO_2$, NO, and $NH_3$. Here, the surfaces are carefully purged of hydroxyl and hydrocarbon contamination before they are characterized. The positive resistance changes for $NO_2$ and NO vary linearly and correspond to an exposure to 1, 2, 3, 4, 5 ppm (10 for $NO_2$) of test gas. The recorded signal for $NO_2$ on n-type PS is that of an acid which has a significant electron affinity (Ervin et al. 1988) and withdraws electrons from the PS interface. In contrast, as $NO_2$ withdraws electrons from p-type PS (FIG. 2.8), we observe a decrease in resistance. The recorded signal for NO on n-type PS corresponds to 100 Ohms/ppm which considerably exceeds the 2 Ohm/ppm signal recorded for p-type PS (Ozdemir et al. 2011). For both n- and p-type PS, the observed change in response corresponds to an increased resistance. Thus, with n-type PS, the amphoteric NO radical acts like an acid withdrawing electrons whereas with p-type PS, the NO radical (Travers et al. 1989) acts like a weak base, contributing electrons but at a much lower rate. The response for the moderately strong base, $NH_3$ (FIG. 2.11A) (Grant et al. 2009), corresponds to a significant drop in resistance. This response, which corresponds to an increase in conductance as $NH_3$ contributes electrons to the majority carriers (donor level electrons) is linear to 4 ppm, begins to saturate at pressures in excess of 5 ppm and is partially quenched at 10 ppm.

With the outlined data, it is possible to consider whether the underlying IHSAB principle described above dictates the response observed for several sensor, basic and acidic gas, interactions. The principle can then be extended to the detection of additional gases with the development of a selective nanostructure deposition approach that facilitates physisorption/electron transduction. By monitoring the trends in hard and soft acid and base behavior, first order selections can be made for the appropriate modification of the PS hybrid interface with nanostructured metal/metal oxide coatings to create a range of selectivities as is apparent from Tables B and C (FIG. 2.25) for a number of gases (Ozdemir and Gole 2008b, 2010a; Wang et al. 2011). The development of selective nanostructured coatings that reversibly complex with a gas can be based in an IHSAB concept which relies, counter to that of Pearson et al. (Pearson 1963, 1990, 1997, 2005; Parr and Pearson 1983) on the combination of hard Lewis acids with soft Lewis bases or soft Lewis acids with hard Lewis bases (counter to that of Pearson et al. (Parr and Pearson 1983; Pearson 1963, 1990, 1997, 2005). To establish this combination, we follow the trends established for the classification of the hard and soft nature of acids and bases (Pearson 1963, 1990, 1997, 2005; Parr and Yang 1989; Geerlings et al. 2003; Yang et al. 1984; Parr et al. 1978; Yang and Parr 1985; Zhan et al. 2003; Cohen and Wasserman 2007; Parr and Pearson 1983).

A first order comparison of the response data in Table B with the exemplary list of hard, borderline and soft acids and bases in Table A clearly demonstrates that hard bases such as ammonia (and ~phosphine) respond most strongly (resistance change) when exposed to a nanostructured $Au_xO$ surface corresponding to the soft acid ($Au^{0, +1}$). The data outlined in Table 2/2 corresponds to a rise in resistance (decrease in conductance) as $NH_3$ contributes electrons to a p-type PS interface, canceling the majority carriers which are holes. This is most easily done for $Au_xO$. In contrast, as $NH_3$ contributes electrons to an n-type PS interface, we observe a decrease in resistance (increase in conductance) as $NH_3$ contributes to the majority carriers which are electrons. However, if we compare the data for $NH_3$ in Tables B and C, we see that they follow a very similar trend. This trend correlates with the mismatch of analyte and nanostructure modified PS interface MO's and the mismatch in hard and soft acid/base character. In contrast to the strong bases $NH_3$ and $PH_3$, the soft bases CO and NO display a maximum response (change in resistance) upon interaction with the borderline to hard acid $SnO_x$ ($Sn^{+2, +4}$). Note also the minimum response of the untreated PS surface to CO and the subsequent decrease for the $Au_xO$ nanostructure treated surface displayed in FIG. 2.6. These properties have not changed over an extended period as we observe no clearly measurable response with an untreated and gold nanostructure treated PS surface. For CO, the decrease in an already small, almost negligible, resistance response versus hybrid PS is consistent with the expected effect of chemisorption for the interaction of a weak acid with a weak base to create a covalent chemical bond that does not facilitate electron transfer.

The responses outlined in Table B, in concert with FIGS. 4 and 5 and Table A, can be correlated further as one generates the materials positioning depicted in FIG. 2.10. This positioning diagram is generated based on the relative responses to the analytes studied as they are exposed to several nanostructured deposits. The results obtained remain constant over an extended period. We position the five bases $NH_3$, $PH_3$, $H_2S$, NO, and CO relative to the porous silicon ($Si^{+1\ to\ +4}$) (Wang et al. 2011) and the PS modified acidic interfaces generated with a nanostructured $TiO_2$ ($Ti^{+4}$), $SnO_x$ ($Sn^{+2,+4}$), $Al_2O_3$ ($Al^{+3}$), NiO ($Ni^{+2}$), $Cu_xO$ ($Cu^{+1,+2}$), and $Au_xO$ ($Au^{0,+1}$) deposit. The rationale for the positioning of $H_2S$ in FIG. 2.3 is the correlation of the relative responses for one ppm $H_2S$ with an $Au_xO$ deposited surface compared to an untreated PS surface (Ozdemir and Gole 2010b) and to the data for $NH_3$, $PH_3$, and NO in Table B. Based on ionization potential as well as proton affinity data, $H_2S$ lies close to the soft acid side of $PH_3$. The basis for the positioning of CO is its virtually non-existent response to $Au_xO$ and its substantial response to $SnO_2$ summarized in FIG. 2.6. Data for $Al_2O_3$ deposits has been generated only for phosphine for which the response is found to be virtually identical to the hybrid PS interface. Thus, the acid strength of the alumina modified PS surface as well as the untreated PS surface and the base strength of $PH_3$ are closely aligned.

There are several additional factors contributing to the construction of FIG. 2.10. A larger resistance change associated with $SnO_2$ suggests that ammonia lies closer to porous silicon than to the extremely strong $Sn^{+4}$ acid site. The inherently hard basic character of ammonia is also consistent with the strong resistance change observed for its interaction with the $Au_xO$ nanostructure deposited surface (Table B, FIG. 2.25). The behavior of ammonia is also strongly mimicked by phosphine, which displays an expected strong increased resistance change relative to the p-type PS surface associated with the $Cu_xO$ and $Au_xO$ nanostructure modified interfaces. The results obtained with ammonia for an n-type PS interface (Table C) are quite similar. We observe a decrease in the magnitude of the resistance response increase relative to the untreated PS surface as a result of a ($Ni^{+2}$) oxide nanostructure deposition. This suggests that the ($Ni^{+2}$) treated surface lies to the soft acid side of the untreated hybrid PS interface. The remaining interactions with NO and $NH_3$ suggest a ($Ni^{+2}$) acid strength in closer proximity to untreated PS. This defines the broader relative response for the $Ni^{+2}$ and hybrid PS regions indicated in FIG. 2.10. As we have noted for phosphine, the responses to the hybrid PS structure and an $Al_2O_3$ nanostructure treated p-type PS surface appear virtually identical. Therefore, we anticipate that phosphine lies equally close to $Al_2O_3$ and PS with $NH_3$, a stronger base, on the hard base side of $PH_3$. This also suggests that the acid character of $Sn^{+4}$ considerably exceeds that of $Al^{+3}$. For $PH_3$, more recent results obtained working with surfaces treated with $TiO_2$ nanostructures prepared using sol-gel methods (Gole et al. 2004) show a significant increase in resistance, 4 to 5 times that of untreated PS, for p-type surfaces. Similarly, $NH_3$ shows a 3.5 to 4 fold increase in resistance compared to the untreated hybrid PS interface response to $NH_3$. These responses, thought to be dominated by the action of $Ti^{+4}$, suggest the response of a harder acid than $Sn^{+4}$ with the moderately strong bases, $NH_3$ and $PH_3$. As we will demonstrate, the extremely hard acid strength of $TiO_2$ can play a very significant role (Gole et al. 2011).

The NO radical has a considerably different molecular orbital makeup and electron shell structure than ammonia or phosphine and represents a weak base. The open shell nature of NO would suggest a very different interaction with hybrid PS and nanostructure treated PS surfaces. In addition, NO is in fact amphoteric as it can bind an electron, if only weakly, which $NH_3$ and $PH_3$ cannot. The behaviour of NO with p and n-type nanostructure treated PS is quite distinct. For the p-type PS interface (Table B), the soft base-hard acid interaction of NO with a $SnO_2$ nanostructured coating leads to a substantial resistance change relative top-type PS. This is the signature of the reversible interaction of a strongly acidic surface with a weak base. Further, the response to gold, copper, and nickel treated surfaces, while considerably muted relative to the tin treated surface, suggests that NO should be positioned directly below the copper ($Cu^{+1,+2}$) systems and intermediate to gold ($Au^{0,+1}$) and nickel ($Ni^{+2}$). The interaction of NO with $Ni^{+2}$ suggests a greater separation from nickel than from gold. While PS and $Ni^{+2}$ may lie in a similar intermediate region, the larger resistance change observed for NO with a $Ni^{+2}$ surface suggests that the ($Ni^{+2}$) modified PS surface lies to the hard acid side of PS, acting as a harder acid deposited to the PS surface. This again suggests a broader range for the relative response of the $Ni^{+2}$ and PS regions as indicated in FIG. 2.10. The results obtained for n-type PS appear to offer a very different picture. However, to understand the data in Table 3, the amphoteric character of NO and the hard acid character of both $SnO_2$ and $TiO_2$ must be considered. FIG. 2.11 demonstrates the response of an untreated PS interface to NO, the changes corresponding to a decrease in the semiconductor conductance as NO extracts electrons. However, because NO is amphoteric, the strong acidic character of $TiO_2$ and to a lesser degree $SnO_2$ overcomes the ability of NO to extract electrons. Instead electrons are extracted from NO and transferred to the n-type PS interface to increase the conductance. This is vividly demonstrated in FIG. 2.12.

FIG. 2.12 compares the response for a prepared n-type PS interface with that for the same PS interface treated with $TiO_2$, $SnO_x$, NiO, $Cu_xO$, and $Au_xO$ nanostructures. In all cases relative measurements for the treated and untreated PS samples exposed to NO at 1, 2, 3, 4, 5, and 10 ppm are considered. The stark changes observed for the $TiO_2$ and $SnO_2$ nanostructure treated PS interfaces (FIGS. 2.12B and 2.12C) are apparent as the conductance of these systems is reversed relative to the untreated device described below and in FIG. 2.11. The observed responses for the untreated samples are virtually linear to 5 ppm although a slight delay in the gas system flow to the sensor and its response is evident below 2 ppm. The observed response again does not double from 5 to 10 ppm, indicating the onset of saturation manifest as a decrease in the rate of conductance increase at the highest NO concentrations.

The variations in response observed for the nanostructure treated PS interfaces, while reflecting the donor level population, demonstrate the important role played by the deposited nanostructures and the nature of acid/base interaction they direct. The observed trends also correlate well with the relative responses observed as NO interacts with p-type PS (Table B, FIG. 2.25). The acid strength of the nanostructures deposited to the n-type PS interface decreases from the strongest acid $TiO_2$ to the weakest acid $Au_xO$ in the order $TiO_2 > SnO_x > NiO > Cu_xO > Au_xO$. FIGS. 2.12E-2.12H demonstrate that the deposition of both $Au_xO$ and $Cu_xO$ nanostructures increases the response of the PS interface (Table 2/3) and that the increase is greater for the weaker acid $Au_xO$. As observed for the nanostructure modified p-type interface, the data suggest that the acid/base strengths of NO and $Cu_xO$ are comparable. Here, $Au_xO$ and $Cu_xO$ act to enhance the electron withdrawing power of the NO radical, which suggests that they represent weaker acids on the n-type PS interface. The effect of the enhanced rate of transfer is apparent (FIGS. 2.12E and F) and evidenced by a decrease in the rate of conductance increase with concentration and a decrease in response with time at the highest concentrations.

NiO displays an intriguing intermediate acid behavior. FIG. 2.12D demonstrates that at the lowest NO concentrations the response of the n-type PS interface is enhanced as the ratio of the responses (2 ppm/1 ppm) increases significantly relative to that for the untreated n-type PS. However, at an NO concentration of 3 ppm, the dynamic response at first increases to a maximum, subsequently decreases, oscillates and again increases. This dynamic behavior is even more pronounced at 4, 5, and 10 ppm. As the NO concentration increases, the transfer of electrons to NO increases to a maximum. However, this transfer reaches a limit when the decorated n-type PS interface is sufficiently depleted that it acts as a stronger acid than the amphoteric NO radical. At this point electrons are extracted from NO (acting as a base) accompanied by a decrease in the measured dynamic resistance (increase in conductance) as the semiconductor donor levels are repopulated. Thus, at the lowest concentrations the NiO nanostructure deposited interface mimics the dynamic behavior of the weak acids $Cu_xO$ and $Au_xO$ and at higher concentrations it is transmuted to a surface similar to that treated with the stronger nanostructured acids $TiO_2$ and $SnO_x$. As a function of concentration, NO acts as both an acid and a base. However, the intermediate behavior observed for NiO also appears to correlate with the results obtained for p-type systems as exemplified in FIG. 2.10. Here again, NO as an analyte interacting with the p-type PS interface was placed as a weak base (Seals et al. 2002) in a region close to the region between $Cu^{+2}$ and $Ni^{+2}$. This is, in effect, the fulcrum region for the Acid/Base Diagram 10, which is also observed for the n-type PS interface.

The Underlying IHSAB Principle

The underlying IHSAB principle, which we describe briefly above dictates the physisorption (electron transduction) directed response observed for a number of basic, acidic, and amphoteric analytes as they interact with nanostructure deposited p and n-type PS extrinsic semiconductor interfaces. A first order comparison of the response data in FIG. 2.25, Tables A and B with the exemplary list of hard, borderline and soft acids and bases in Table A demonstrates that hard bases such as $NH_3$ respond most strongly when exposed to an $Au_xO$ nanostructure treated PS surface. Within the framework of the IHSAB principle, this is not surprising since $Au_xO$ is a soft acid ($Au^{0,+1}$). The results which we obtain for the amphoteric NO radical demonstrate the importance of the relative acidity (Table A) of nanostructured metal oxide deposits, which is more strongly manifest on an n-type as opposed to a p-type PS interface. Their ability to direct electron flow dictates whether NO acts as either a weak acid or weak base. The responses outlined in Table C, FIG. 2.11 and FIG. 2.12 for an n-type PS interface can be correlated to demonstrate consistency with the materials positioning diagram of FIG. 2.10. Because of the significant catalogue of information on metal oxides, this principle can be extended to the detection of additional gases with the development of a selective nanostructure deposition approach which facilitates reversible physisorption (electron transduction). By monitoring the trends in hard and soft acid and base behavior, first order selections can be made for the modification of the PS hybrid interface (or any extrinsic semiconductor interface into which a microporous structure can be formed) with nanostructured metal oxide deposits to create a range of selectivities for a number of gases.

The data in Tables A and B (FIG. 2.25) to correlate the materials positioning indicated in FIG. 2.10, within especially similar molecular analogs, with a focus to sensor array development. FIG. 2.10 is constructed within the framework of the acid and base character outlined in Table A considering, to first order, the hard acid strength which we associate with a $Ti^{+4}$ ($TiO_2$) or $Sn^{+4}$ ($SnO_2$) configuration, the soft acid strength to be associated with an $Au^{0,+1}$ ($Au_xO$) configuration, and the intermediate (borderline) acid strength we associate with the porous silicon hybrid surface. Here, the silicon oxidation state ($Si_xO_y$) is considered to vary from +1 to +4 (Wang et al. 2011). Superimposed relative to this structure, we insert the results outlined in Table 2/2 for the intermediate acid $Ni^{+2}$, the soft and intermediate acids $Cu^{+1,+2}$ and the comparatively strong acid state with which we associate $Al^{+3}$ ($Al_2O_3$) to begin to formulate a user's table for the IHSAB principle.

The introduction of the nanostructured metal oxides to the nanoporous PS surface modifies the sensing process by transforming the surface of the chemically sensitive doped PS nanoporous layer. The sensor resistance increases for "basic" gases which are oxidized (NO, CO, $NH_3$, $PH_3$, $H_2S$)

on p-type PS. This process is amplified through the interaction of a modified acidic metal oxide surface. If an electron is donated to a p-type PS surface, this process will act to reduce the number of majority carriers (holes) and thus will promote an increase in resistance. In contrast, the interaction of a gas that is reduced on p-type silicon, exemplified by the acidic gas $NO_2$, removes electrons from the p-type PS surface, increases the majority charge carriers and decreases resistance (FIG. 2.8) (Gole et al. 2011; Laminack et al. 2012; Ozdemir et al. 2011). In effect, the nanostructures act as antennas to transduce charge. The process is reversed for n-type interfaces.

The process of physisorption (electron transduction) must involve the interaction of high-lying occupied (low lying unoccupied) molecular orbitals of each individual gas. These gases are the electron donors (acceptors) with the electron acceptor (donor), represented by the acidic (basic) metal oxides used to modify the p or n-type PS interface. This process will differ from gas to gas with changes in the nanostructured deposit. However, the nature of the interaction, as it provides for increased physisorption (electron transduction) and minimizes chemical bond formation (chemisorption), therefore influencing the flow of electrons from a gaseous molecule to the sensor, provides the basis for the observed resistance changes. The presence of a fractional nanostructured oxide coating on the PS surface promotes further interaction with the interface. The process whereby a gas transfers or withdraws electrons as it interacts with that surface will be strongly influenced by the balance of chemical bonding, which greatly inhibits electron flow, and physical absorption, which can facilitate the process.

Given the limits of the system considered, we note the considerable increase in sensitivity inherent to the n-type vs. that observed for the p-type systems. The n-type systems, while displaying quenching at concentrations in excess of 5 ppm, are apparently capable of operation at much lower concentrations than the p-type systems, possibly extending to the low ppb or ppt levels. Concomitantly, the p-type systems appear to provide a linear response to notably higher pressures than do the n-type systems (Gole et al. 2011; Lewis et al. 2007; Lewis et al. 2005). As the pore structure for these systems can be further optimized, the sensitivity ranges can be expanded.

The precise details of the mechanism for the resistance change which appears to be characteristic of virtually all oxidized (increased resistance) and reduced (decrease in resistance), gases on the individually modified hybrid p-type PS interfaces and their counterparts in an n-type system will require further experimentation and modeling. If we, however, consider an appropriate sensor mechanism for interaction with oxide surface subgroups, the fractional nanostructure coating of either a p-type or an n-type sensor is consistent with the changes in resistance that we outline above. Basic analytes will provide an electron to the PS interface whereas acidic analytes will remove an electron, leading to a decrease or increase in the number of majority carriers. This, of course, will affect the observed conductance.

The temperature dependence shown in FIG. 2.5 for both p- and n-type semiconductors indicates that one can expect vacant donor levels for an n-type system and available holes for a p-type system at room temperature (Korotcenkov and Cho 2010). If an analyte acts to add electrons to the vacant donor electron levels of an n-type extrinsic semiconductor, it can be anticipated that the population of these levels will "top-out" and the resistance will reach a limiting lower value. This limit in resistance is likely demonstrated when NO, acting as a base is exposed to the $TiO_2$ decorated (FIG. 2.12*b*) n-type PS interface. An analogous decrease to a minimum resistance is observed for the p-type PS system. Where $NO_2$ extracts electrons and enhances conductance. FIG. 2.8 demonstrates the bottoming-out of the resistance associated with the removal of electrons as would be expected from FIG. 2.5. The outlined results obtained with $NO_2$ allow us to position this acid in FIG. 2.10.

The outlined correlations associated with FIG. 2.3 point to an additional aspect of the dynamic nature of these systems. The Fermi level is dynamic and the change in the Fermi level energy must be evaluated as we consider processes initiated with extrinsic semiconductor interfaces. This will have significant consequences as one attempts to employ these prepared interfaces in transduction processes which include any type of dynamic electron transfer and, for that matter, solar pumping involving these systems. While many approaches focus on the bandgap when considering interactions associated with an extrinsic semiconductor, this focus lacks appropriate dynamic considerations. The effect of process on energy increments in a dynamic system and especially on the Fermi level should be strongly considered.
Application to Nanowire Configurations The considerations we have outlined within the IHSAB framework can also be applied to semiconductor nanowire configurations. Li et al. (2010) have recently reported enhanced gas sensing for $H_2S$ by assembling Pd nanoparticles on $SnO_2$ nanowires (FIG. 2.13). These observations are readily explained within the IHSAB model. The interaction of $H_2S$, a moderate base, gives up electrons to the n-type $SnO_2$ nanowire. This process, which increases the majority carrier concentration and the conductance, is made more efficient due to the presence of the weak acid Pd nanoparticle islands. Here, the weak acid (Pd-Table 2/1) interacts with the moderately strong base, $H_2S$, promoting physisorption (electron transduction) and a more efficient electron transfer.

Kim et al. (2010) have studied gas sensing for $O_2$ on $In_2O_3$ nanowires enhanced with Pt nanoparticle depositions. These authors transformed continuous Pt shell layers into cubic Pt nanoparticles deposited to $In_2O_3$ (FIG. 2.14). "In an $O_2$ sensing test, the Pt-functionalized $In_2O_3$ nanowires revealed exceptionally higher sensitivity and faster response than did the bare $In_2O_3$ nanowires. Here again the IHSAB model explains the experimental observations. The interaction of $O_2$, a moderate base with p-type $In_2O_3$ leads to a decrease in conductance. A resultant increase in sensor resistance is again promoted by the weak acid Pt which promotes a "physisorbed" interaction with $O_2$.

Recently, Kolmakov et al. (2005) studied the response of a Pd-functionalized $SnO_2$ nanostructure to sequential hydrogen and oxygen pulses at 473 and 543 K (FIG. 2.15). Here, a strong increase in resistance is noted at both temperatures upon hydrogen introduction. No response is observed for oxygen at 473K but a drop in resistance is monitored at 543K. These results can be readily explained within the IHSAB model. The strong acid hydrogen interacts with n-type $SnO_2$, removing majority carriers and leading to an increase in resistance. At the higher temperatures, the formation of $O_2^-$, a moderate to strong base, on the $SnO_2$ surface provides additional electrons to increase conductance, again enhanced by the presence of the weak acid Pd nanostructured islands.
Application to Additional Semiconductors Finally we should note that the silicon or layers and the porous silicon (PS) structures, devices, and methods, described in the following discussion can be replaced with any alternate extrinsic semiconductor (e.g., GaP, InP, CdTe) onto which a porous microstructure can be generated (Levy-Clement et al. 1994). Further, the configuration in FIG. 2.1 can be adapted to a pass-through microporous membrane. This greatly broadens the range of nanostructure-interface combinations which can be potentially exploited as the alternate extrinsic semiconductors can be a p-type substrate, a p+-type substrate, or an n-type substrate.

Time Varying Operation and False Positives-Sensing in an Unsaturated Mode

To further improve the sensitivity and stability of the porous silicon sensors, we have developed the method of pulsed system frequency analysis (PSFA). Here, methods of acoustic theory are applied to signal analysis. The benefits of this approach include improved measurement sensitivity, isolation of periodic noise sources, and the ability to evaluate the trade-off between the precision and duration of measurement to aid the design of an experimental system. A defined gas pulsing technique is combined with FFT signal analysis to allow a sensor gas response to be measured, without saturation, and filtered on a drifting baseline, so as to eliminate false positives and the effects of external noise (as might be associated with pressure, temperature, and humidity variation). FIG. 2.16 depicts a test in which the concentration of ammonia (in $N_2$) being delivered to the sensor was pulsed between 0 and 5 ppm at a frequency of 1/60 s (0.017 Hz). The baseline for the device increases during the test as the adsorption and desorption of ammonia begin to equilibrate, however, the magnitude of the signal at the beginning and end of the pulsing sequence and throughout the sequence remains virtually the same as we operate in an unsaturated mode. The baseline can also be affected by low frequency changes in temperature and pressure, however, because of the pulsed mode of operation which has been introduced to run all of the sensor systems this drift can be both "locked out" and monitored (Lewis et al. 2007). By introducing an FFT analysis to the reversibly, linearly, responding, PS gas sensor, the gas response can be acquired and filtered on a drifting baseline or in the presence of external noise sources (FIGS. 2.17 and 2.18).

FIG. 2.17 shows an example of the raw data and the high fidelity outputs after FFT analysis and filtering with the PSFA technique. The benefits of this approach include improved measurement sensitivity, and isolation of periodic noise sources. This technique, closely aligned with the advantages of the PS versus other sensors, does not require stability in the baseline resistance or low thermal sensitivity. With this method, thermal noise, random fluctuations, and long settling times are mitigated. Additional benefits include the ability to detect gas signals when environmental signals are dominant, and the testing time can be greatly reduced. The FFT data analysis method for the PS gas sensor also offers the ability to operate below saturation and provides several safeguards against false positives. If the false positive is associated with the delivered gas, attributes of the "time-delay" module become unstable and the dataset is withdrawn (Lewis et al. 2007).

Sensor Rejuvenation

If a sensor is poisoned due to contamination or extensive exposure to a deleterious component of a gas mixture, which might be a strong acid, it is advantageous to have available a rejuvenation process. In most cases the rejuvenation of a sensor is difficult, at best; however, the simple open structure inherent to the porous silicon sensor facilitates this process. FIG. 2.19 demonstrates the results of a straightforward and repeatable rejuvenation process that can be applied to poisoned sensors (Ozdemir and Gole 2008b). This facilitates their cycling and decreases the long-term expense of a sensor device.

Summary of Sensor Attributes

A correctly developed porous interface sensor has several attributes. (1) its rapid response (~2 s), sensitivity (sub-ppm), and reversibility, (2) its operation at room temperature as well as at stable, readily accessible elevated temperatures with an insensitivity to temperature drift, (3) its potential operation in a heat-sunk configuration allowing reliable performance to a surface temperature of 80° C. even in highly elevated temperature (combustion or flue gas) environments (in sharp contrast to metal oxide sensors), (4) its ease of modification with a diversity of clearly mapped gas-selective nanostructured materials, providing a range of sensitivities for a given gas and the format for sensor arrays, (5) its low cost of fabrication usually with a single nanostructure modification, (6) its ease of operation combining micro- and nanotechnology, (7) its low power consumption (power requirements less than a watch battery), (8) its ease of rejuvenation following contamination, (9) its ability to rapidly assess false positive signals using FFT techniques, operating the sensor in a pulsed gas mode, and (10) its potential for use in the development of solar pumped sensors.

Extension to Phytocatalysis-Enhanced System

Photocatalysts, formed as the nanostructured metal oxides or their modification, can be used to further enhance the activity of the nanopore coated microporous PS interface (FIG. 2.1) through their interaction with solar radiation. In such a way, the sensor array configurations that we have been developing can be extended to behave as microreactors in which visible light absorbing quantum dot (QD) photocatalysts are placed within the pores of PS microarray and excited using PS electroluminescence or photoluminescence. Properly employed, these microreactors might then be used to form "solar pumped" sensors. The quantum dots are exemplified by the highly efficient light absorbing titania-based nanocolloids which we have produced in a nanoscale synthesis at room temperature, (Gole et al. 2004; Kumar et al. 2005; Chen et al. 2005; Gole et al. 2006a; Prokes and Carlos 2005; Lewis et al. 2007; Ogden et al. 2008; Gole, et al. 2010) and that can be nitridated in seconds to produce nitrogen doped, stable, and environmentally benign $TiO_{2-x}N_x$ photocatalysts whose optical response can be tuned across the entire visible region. Tunability throughout the visible is found to depend upon the degree of nanoparticle agglomeration and upon the ready ability to seed the nanoparticles with metals (metal ions) including Pd and additional active dopants including the transition metals (Chen et al. 2005). These photocatalyst are found to readily photodegrade methylene blue and gaseous ethylene. They can also be used to eliminate environmental contaminants.

FIG. 2.20 demonstrates the photocatalytic efficiency of nitrided anatase $TiO_{2-x}N_x$ quantum dots generated using the sol-gel technique and Degussa P25 (Chen et al. 2005), a well-known nanocatalyst. The photodegradation of methylene blue is not only 4 times more efficient than P25 at 390 nm, P25 at 390 nm, but also the nitrided quantum dots show a photocatalytic efficiency in the visible (540 nm) which virtually eclipses that of P25.

It is significant that these oxynitride ($TiO_{2-x}N_x$) quantum dots can be transformed from liquids to gels, and, in addition, can be placed on the PS surface in a sensor-microreactor based conformation in order to produce a photocatalytically enhanced "solar pumped sensor" response.

Mixed Gas Format

The sensors which we have outlined, operated for identification of a given analyte can be made to function in an array-based format on the bases of a row matrix response to a given analyte. They can be operated in a mixed gas format, creating a sensor array matrix. Sensor array selectivity is another very important sensor operating characteristic which must be demonstrated. However, we exemplify the inherent selectivity that a nano/microporous surface can display in a mixed gas configuration in FIG. 2.19. Here, with an untreated PS interface (even before treatment with $Au_xO$ nanostructures), the analysis for 1 and 3 ppm $NH_3$ can be carried out in the presence of 20 ppm $NO_x$ (Lewis et al. 2005). We note that the introduction of an $Au_xO$ nanostructured deposit can considerably improve the relative sensitivity to ammonia and that the introduction of a $SnO_x$ nanostructured deposit leads to a substantial increase in NO sensitivity. These three sensors, in tandem, produce three distinct responses to an $NH_3+NO$ mixture.

Comparison of Some Embodiments to Alternate Technologies

One can compare (Ozdemir et al. 2011) the positive aspects of an embodiment of the sensor platform with competing and complementary technologies that are currently available or in the process of becoming available. The two main sensor technologies are (1) Electrochemical based, and (2) Metal Oxide based sensors. Each of these technologies have unique advantages, however, both are also plagued with drawbacks. For example, electrochemical sensors are known for low power operation, rapid response, and insensitivity to humidity; but they have poor sensitivity and are inherently complex and expensive to produce and replace.

The metal oxide sensors (FIG. 2.22), when compared to electrochemical sensors are slightly less costly to produce, but are still significantly more complex than the technology that we propose. However, the main drawbacks of the metal oxide sensor include low sensitivity, poor selectivity, high power requirements, and most importantly, the need to operate at elevated temperatures. The latter requirement is a major drawback for several reasons. First, a power consuming heating element must be provided with the sensor housing to precisely control the temperature of the sensor element. This is, in large part, intimately tied to the correct identification of the gas of interest. A formaldehyde sensor will operate at one temperature whereas an ethanol sensor will operate at another. Otherwise the devices are virtually identical. Distinguishing one gas from another thus requires that the heating element and sensor be well separated (channel) from the remaining electronics. This in turn means that this configuration can be greatly affected by an impinging combustion or flue gas, rendering moot the correct identification of gaseous species in the flow. In contrast the PS sensor configuration depicted in FIG. 2.1 is far simpler and does not require the complexity of a system separated sensor/heater configuration. In a heat sunk environment, it is potentially capable of operation in a high temperature gas flow. This simplicity and capability of operation thus represents a revolutionary change. Further, the attributes of an extrinsic semiconductor technology developed by combining array generation through the coupling of acid/base chemistry with the properties of extrinsic semiconductors suggests a general road map for array development, and the importance of further understanding the nuances of this process. We provide an important element to combine with well-developed fabrication and CMOS technologies that greatly simplifies device fabrication and costs relative to optical technologies.

Chemisorption and the Analog of the HSAB Principle

As the IHSAB model applies to the general development of a sensor interface so to does an extrapolation of the HSAB model apply to the development of a Microreactor model. However, in order to develop the model it is necessary to modify the interface of FIG. 2.1 so that it is more compatible with microreactor design. This dictates that one attempt to develop flow-through configurations. It is significant that the oxynitride ($TiO_{2-x}N_x$) quantum dots which we have previously discussed can be transformed from liquids to gels, and, in addition, can be placed on the PS surface in a sensor-microreactor based conformation to produce a photocatalytically enhanced "solar pumped sensor" response. Of possibly greater importance to microreactor applications is a recently developed microfilter configuration (Campbell et al. 2008; Gole et al. 2009). This technology represents the first single step etch-liftoff procedure (one step separation) which allows the removal of macroporous PS layers. FIG. 2.23 demonstrates that filters with pore diameters ranging from 1 to 2 microns and thickness from 3 to 70 micrometers have been produced. These silicon-based filters carry a polarizing negative charge and represent an alternative to porous alumina films (pore diameter not yet in the one to three micron range) with a capability for operating at significantly elevated temperatures as compared to polymer films. Pt and Cu have been introduced to these filters to create an effective reducing surface.

Physisorption (Electron Transduction) Versus Chemisorption

In developing sensor and microreactor configurations using the IHSAB and HSAB concepts one need be continuously mindful of the dynamics of interaction as the process of electron transfer takes place. FIG. 2.24 demonstrates the effect which the strong acid $SnO_x$ has on the $NO_2$ interaction with the PS interface (Laminack et al. 2012). Here, both an acidic analyte and the nanostructure modified PS interface compete for electrons. If $NO_2$ and $SnO_x$ compete effectively for electrons, the competition might be expected to diminish the sensitivity of the interface and influence physisorption (electron transduction) as measured by a significant resistance change. One does observe a muted response after. However, the weak and diffuse nature of the observed response after $SnO_x$ treatment suggests that it is equally likely to be the result of the strong influence of chemisorption. While $NO_2$ is a moderate acid, $NO_2^-$, which can be formed as $NO_2$ extracts an electron from the n-type PS interface, corresponds to a moderate to strong base. Table 2/1 suggests that an n-type PS surface corresponds to a borderline acidic surface. For this reason, one might expect a chemical interaction (chemisorption) with $NO_2$ and $NO_2^-$ as dictated by the IHSAB/HSAB principle to be of only moderate effect. If, however, the PS surface is treated with nanostructured $SnO_x$, it is possible to obtain a strong chemical interaction between this strong acid and $NO_2^-$. The muted and diffuse response with concentration in FIG. 2.24b may signal this chemisorption. It is to be emphasized that the base strength of $NO_2^-$ and the acid strength of $SnO_x$ are much more closely matched than those of either the much stronger acid, $TiO_2$, or the weaker acids $Cu_xO$ and $Au_xO$. Thus (Gole and Ozdemir 2010) one anticipates a chemisorptive interaction.

REFERENCES

Each is Incorporated Herein by Reference

Andzelm J. (ed.) (1991) *Density Functional Methods in Chemistry*. Springer-Verlag, New York Campbell J., Corno J. A., Larsen N. and Gole J. L. (2008) Development of porous-silicon-based active microfilters. *J. Electrochem. Soc.* 155, D128-D132; DOI 10.1149/1.2811868

Chen X., Lou Y., Samia A. C. S., Burda C. and Gole J. L. (2005). Formation of oxynitride as the photocatalytic enhancing site in nitrogen-doped titania nanocatalysts: comparison to a commercial nanopowder. *Adv. Funct. Mater.* 15, 41-49; DOI: 10.1002/adfm.200400184

Cohen M. H. and Wasserman A. (2007). On the foundations of chemical reactivity theory. *J. Phys. Chem. A* 111, 2229-2242; DOI: 10.1021/jp066449h Dixon D. A. and Gole J. L. (1997). Suggested correlation between the visible photoluminescence and the fourier transform infrared spectrum of a porous silicon surface. *J. Phys. Chem. B* 101, 8098-8102; DOI: 10.1021/jp971177r.

Dixon D. A. and Gole J. L. (2005). Time dependent density functional theory predictions of the vertical excitation energies of silanones as models for the excitation process in porous silicon. *J. Phys. Chem. B* 109, 14830-14835; DOI: 10.1021/jp050538x Dixon D. A. (2010) Private discussions Ervin K. M., Ho J. and Lineberger W. C. (1988). Ultraviolet photoelectron spectrum of nitrite anion. *J. Phys. Chem.* 92, 5405-5412; DOI: 10.1021/j100330a017.

Foell H., Christophersen M., Carstenson J. and Hasse G. (2002). Formation and application of porous silicon. *Mater. Sci. Eng. R.* 280, 1-49;

Foucaran A., Pascal-Delannoy F., Giani A., Sackda A., Commette P. and Boyer P. (1997) Porous silicon layers used for gas sensor applications. *Thin Solid Films.* 297, 317-320; http://dx.doi.org/10.1016/S0040-6090(96)09437-0

Fukui K., Yonezawa T. and Shingu H. (1952) A molecular orbital theory of reactivity in aromatic hydrocarbons. *J. Chem. Phys.* 20, 722-725 DOI:10.1063/1.1700523

Geerlings P., De Proft F. and Langenaeker W. (2003) Conceptual density functional theory. *Chem. Rev.* 103, 1793-1874; DOI: 10.1021/cr990029p.

Gole J. L., Dudel F. P., Grantier D. and Dixon D. A. (1997) "Origin of porous silicon photoluminescence: evidence for a surface bound oxyhydride-like emitter," *Phys. Rev. B.* 56, 2137-2153; DOI:10.1103/PhysRevB.56.2137

Gole J. L. and Dixon D. A. (1998a) Potential role of silanone and silylenes in the photoluminescence-excitation, visible-photoluminescence-emission, and infrared spectra of porous silicon, *Phys. Rev. B.* 57, 12002-12016; DOI: 10.1103/PhysRevB.57.12002

Gole J. L. and Dixon D. A. (1998b) "Electrochemical methoxylation of an HF-etched porous silicon surface," *J. Phys. Chem. B.* 102, 1768-1774; DOI: 10.1021/jp980140j Gole J. L. and Dixon D. A. (1998c) "Evidence for oxide formation from single and multiphoton excitation of a porous silicon surface or silicon nanoparticles", *J. Appl. Phys.* 83, 5985-5990; doi:10.1063/1.367464

Gole J. L. and Dixon D. A., (2000) "Isomerization of fluorophors on a treated silicon surface,"*J. Phys. Chem. B.* 104, 1777-1782; DOI: 10.1021/jp9933469

Gole J. L., Fedorov A. G., Hesketh P. and Burda C. (2004) From nanostructures to porous silicon: sensors and photocatalytic reactors. *Phys. Stat. Sol. C.* 1(52), S188-197; DOI: 10.1002/pssc.200405139

Gole J. L., Stout J., Burda C., Lou Y. and Chen X. (2004). Highly efficient formation of visible light tunable $TiO_{2-x}N_x$ photocatalysts and their transformation at the nanoscale. *J. Phys. Chem. B.* 108, 1230-1240; DOI: 10.1021/jp030843n Gole J. L., Prokes S. M., Stout J. D., Glembocki O. J. and Yang R. (2006a) Unique properties of selectively formed $ZrO_x$ nanostructures—light enhancement from a metal oxide. *Adv. Mater.* 18, 664-667; DOI: 10.1002/adfm.200400184

Gole J. L., Veje, E., Egeberg, R. G., Ferreira da Silva A., Pepe I. and Dixon D. A. (2006b) Optical analysis of the light emission from porous silicon: a hybrid polyatom surface-coupled fluorophor, *J. Phys. Chem. B.* 110, 2064-2073; DOI: 10.1021/jp0555302

Gole J. L., Lewis S., and Lee S. (2007) Nanostructures and porous silicon: activity at interfaces in sensors and photocatalytic reactors. *Phys. Stat. Solids (a).* 204(5), 1417-1422; DOI: 10.1002/pssa.200674369

Gole J. L., Ozdemir S., Prokes S. and Shin H-C. (2009) Active microfiltered sensor interfaces, photocatalytic reactors, and microbatteries using combined micro/nanoporous interfaces. *Phys. Stat. Solid.* 6, 1773-1776; DOI: 10.1002/pssc.200881009

Gole J. L., Prokes S. M., Qiu X., Burda C. and Glembocki 0. J. (2010) Study of concentration-dependent cobalt ion doping of $TiO_2$ and $TiO_{2-x}N_x$ at the nanoscale. *Nanoscale.* 2, 1134-40; DOI: 10.1039/c0nr00125b Gole J. L. and Ozdemir S. (2010). Nanostructure directed physisorption vs. chemisorption at semiconductor interfaces: the inverse of the hard-soft acid-base (HSAB) concept. *Chem Phys Chem.* 11, 2573-2581; DOI: 10.1002/cphc.201000245

Gole J. L., Goude E. C. and Laminack W. (2012) Nanostructure driven analyte-interface electron transduction: a general approach to sensor and microreactor design. *Chem Phys Chem.* 13(2), 549-561; DOI: 10.1002/cphc.201100712

Grant D. J., Matus M. H., Anderson K. D., Camaioni D. M., Neufeldt S., Lane C. F. and Dixon D. A. (2009) Thermochemistry for the dehydrogenation of methyl-substituted ammonia borane compounds. *J. Phys. Chem. A.* 113, 6121-6132. DOI: 10.1021/jp902196d Grant G. H. and Richards W. G. (1995) *Computational Chemistry.* Oxford University Press, Oxford.

Hehre W. J., Radom L., Schleyer P. R. and Pople J. A. (1986) *Ab Initio Molecular Orbital Theory.* John Wiley and Sons, New York.

Hirst D. M. (1990) *A Computational Approach to Chemistry.* Blackwell Scientific, Oxford.

Huheey J. E. (1978) *Inorganic Chemistry.* 2nd ed. Harper and Row, New York.

Kim S. S., Park S. Y., Choi S-W., Kim H. S., Na H. A., Yang J. C. and Kim H. W. (2010) Significant enhancement of the sensing characteristics of $In_2O_3$ nanowires by functionalization with Pt nanoparticles. *Nanotechnology.* 21(41) 1-7; DOI:10.1088/0957-4484/21/41/415502

Kolmakov A., Klenov D. O., Lilach L., Stemmer S. and Moskovitz M. (2005) Enhanced gas sensing by individual $SnO_2$ nanowires and nanobelts functionalized with Pd catalyst particles. *Nanoletters.* 5, 667-673; DOI: 10.1021/n1050082v Korotcenkov G. and Cho B. K. 2010) Porous Semiconductors: Advanced Material for Gas Sensor Applications. *Crit. Rev. Solid St. Mater. Sci.* 35(1), 1-37; DOI 10.1080/10408430903245369

Kottke P. A. Fedorov A. G. and Gole J. L. (2009) Multiscale mass transport in porous silicon gas sensors. In: Schlesinger M. (ed.) *Modern Aspects of Electrochemistry*, Vol. 43. Springer, New York, N.Y., 139-168; http://dx.doi.org/10.1007/978-0-387-49582-8

Kumar S., Fedorov A. G. and Gole J. L. (2005) Photodegradation of ethylene using visible light responsive surfaces prepared from titania nanoparticle slurries. *Appl. Catal. B.* 57, 93-107; http://dx.doi.org/10.1016/j.apcatb.2004.10.012

Laminack W., Pouse N. and Gole J. L. (2012) The dynamic interaction of $NO_2$ with a nanostructure modified porous silicon matrix: the competition for donor level electrons. *J. Electrochem. Soc.* submitted Lévy-Clément C. (2002) Encyclopedia of Electrochemistry Chapter 3.2, Semiconductor electrodes and photoelectrochemistry, S. Licht, Editor, ISBN 3-527-30250-6 (Vol. 6 in "Encyclopedia on Electrochemistry," A. Bard, Series Editor), WILEY-VCH, Weinheim, Germany Levy-Clement C., Lagoubi A., and Tomkiewicz M. (1994) Morphology of porous $n^+$ type silicon obtained by photoelectrochemical etching. *J. Electrochem. Soc.* 141, 958-967; http://dx.doi.org/10.1149/1.205f65

Lewis S. E., DeBoer J. R., Gole J. L., and Hesketh P. J. (2005) Sensitive, selective, and analytical improvements to a porous silicon gas sensor. *Sens. Actuators B.* 110, 54-65; http://dx.doi.org/10.1016/j.snb.2005.01.014

Lewis S. E., DeBoer J. R., and Gole J. L. (2007) Pulsed system frequency analysis for device characterization and experimental design. *Sens. Actuators B.* 122(1), 20-29; http://dx.doi.org/10.1016/j.snb.2006.04.113

Li H., XU J., Zhu Y., Chen X., and Xiang X. (2010) Enhanced gas sensing by assembling Pd nanoparticles onto the surface of $SnO_2$ nanowires. *Talanta.* 82, 458-463; http://dx.doi.org/10.1016/j.talanta.2010.04.053

Moseley P. T. (1997) Solid state gas sensors. *Meas. Sci. Technol.* 8, 223-237; doi: 10.1088/0957-0233/8/3/003

Nassiopoulos A. G. (1997) Local formation and patterning of porous silicon. In: Canham L. (ed.), *Properties of Porous Silicon.* IEE-Books, London, 77-80.

NIST (2003) X-ray Photoelectron Spectroscopy Database, Version 3.5 National Institute of Standards and Technology, Gaithersburg, (http://srdata.nist.gov/xps/).

Ogden A., Fedorov A., Hong J., and Gole J. L. (2008) Maintaining particle size in the transformation of anatase to rutile titania nanostructures. *J. Phys. & Chem. of Solids,* 69, 2898-2906; DOI: 10.1016/j.jpcs.2008.07.016

Ozdemir S. and Gole J. L. (2008a) The potential of porous silicon gas sensors. *Currents opinions in Solid State and materials Science.* 11, 92-100; DOI: 10.1016/j.cossms.2008.06.003

Ozdemir S. and Gole J. L. (2008b) Porous silicon gas sensors for room temperature detection of ammonia and phosphine. Chemical Sensors 8: Chemical (Gas, Ion, Bio) Sensors and Analytical Systems, *ECS Transactions,* 16(11), 379-387; ISBN 1566776570, 9781566776578

Ozdemir S. and Gole J. L. (2010a) A phosphine detection matrix using nanostructure modified porous silicon gas sensors. *Sens. Actuators B.* 151, 274-280; http://dx.doi.org/10.1016/j.snb.2010.08.016

Ozdemir S. and Gole, J. L. (2010b) Gas transport and response in porous silicon sensors. Materials Research Society Spring Meeting, Apr. 5-9, 2010, San Francisco, Abstract K5.33.

Ozdemir S., Osburn T. and Gole J. L. (2011) Transient conversion of NO to $NO_2$ on a nanostructure modified porous silicon gas sensor detection matrix *J. Electrochem. Soc.* 158(7), J201-J207; http://dx.doi.org/10.1149/1.3583368

Parr R. G., Donnelly R. A., Levy M. and Palke W. E. (1978) Electronegativity: the density functional viewpoint *J. Chem. Phys.* 68, 3801-3807; DOI: 10.1063/1.436185

Parr R. G. and Pearson R. G. (1983) Absolute hardness: companion parameter to absolute electronegativity. *J. Am. Chem. Soc.* 105, 7512-7516. DOI: 10.1021/ja00364a005

Parr R. G. and Yang W. (1989) *Density functional theory of atoms and molecules.* Oxford University Press, New York.

Pearson R. G. (1963) Hard and soft acids and bases. *J. Am. Chem. Soc.* 85, 3533-3539; DOI: 10.1021/ja00905a001

Pearson R. G. (1988) Absolute electronegativity and hardness: application to inorganic chemistry. *Inorg. Chem.* 27, 734-740; DOI: 10.1021/ic00277a030

Pearson R. G. (1990) Hard and soft acids and bases—the evolution of a chemical concept. *Coord. Chem. Rev.* 100, 403-425; DOI 10.1016/0010-8545(90)85016-L Pearson R. G. (1997) *Chemical hardness.* Wiley-VCH, Weinheim.

Pearson R. G. (2005) Chemical hardness and density functional theory. *J. Chem. Sci.* 117, 369-377; DOI: 10.1007/BF02708340

Politzer P. (1987) A relationship between the charge capacity and the hardness of neutral atoms and groups. *J. Chem. Phys.* 86, 1072; doi:10.1063/1.452296

Prokes S. M. and Carlos W. E. (2005) Defect related optical behavior in surface modified $TiO_2$ nanostructures. *Adv. Funct. Mater.* 15, 161-167; DOI: 10.1002/adfm.200305109

Rudden M. N. and J. Wilson (eds.) (1993) *Elements of solid state physics.* John Wiley and Sons, New York, N.Y.

Schechter I., Ben-Chorin M. and Kux A. (1995) Gas sensing properties of porous silicon. *Anal. Chem.* 67, 3727-3732; DOI: 10.1021/ac00116a018

Seals L., Tse L. A., Hesketh P. J. and Gole J. L. (2002) Rapid, reversible, sensitive porous silicon gas sensor *J. Appl. Phys.,* 91, 2519-2523; doi:10.1063/1.1436556

Travers M. J, Cowles D. C. and Ellison G. B. (1989) Reinvestigation of the electron affinities of $O_2$ and NO *Chem. Phys. Lett.* 164, 449-455. http://dx.doi.org/10.1016/0009-2614(89)85237-6

Wang T., Gole J. L., White M. G., Watkins C., Street S. C., Fang Z. and Dixon D. A. (2011) The surprising average oxidation state of fumed silica and the nature of water binding to the silicon oxides and hydroxides, *Chem. Phys. Lett.* 501, 159-165 http://dx.doi.org/10.1016/j.cplett.2010.11.013

Yang W., Parr R. G. and Pucci R. (1984) Electron density, Kohn—Sham frontier orbitals, and Fukui functions *J. Chem. Phys.* 81, 2862-2863; DOI: 10.1063/1.447964

Yang W. and Parr R. G. (1985) Hardness, softness, and the Fukui function in the electronic theory of metals and catalysis *Proc. Natl. Acad. Sci. USA* 82, 6723-6726

Zhan, C. G., Nichols J. A. and Dixon D. A. (2003) Ionization potential, electron affinity, electronegativity, hardness, and electron excitation energy: molecular properties from density functional theory orbital energies. *J. Phys. Chem. A* 107, 4184-4195; DOI: 10.1021/jp0225774

Ziegler T. (1991) Approximate density functional theory as a practical tool in molecular energetics and dynamics. *Chem. Rev.* 91, 651-667; DOI: 10.1021/cr00005a001.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding based on numerical value and the measurement techniques. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

The invention claimed is:

1. A device, comprising:
a conductometric porous silicon gas sensor including a n-type silicon substrate having a porous silicon layer, wherein a plurality of nanostructures are disposed on a portion of the porous silicon layer to provide a fractional coverage on the porous silicon layer, wherein the sensor is configured to allow light to illuminate the porous silicon layer, wherein the conductometric porous silicon gas sensor is operative to transduce the presence of a gas into an impedance change when exposed to light, wherein the impedance change correlates to the gas concentration.

2. The device of claim 1, wherein the sensor includes a window or opening to allow light to illuminate the porous silicon layer.

3. The device of claim 1, wherein the light is from a light source selected from the group consisting of: the sun, an artificial light source, and a combination thereof.

4. The device of claim 3, wherein the light source is part of the device.

5. The device of claim 1, wherein the light is selected from the group consisting of: visible light, ultraviolet light, and a combination thereof.

6. The device of claim 5, wherein the nanostructure is selected from the group consisting of: aluminum oxide, aluminum oxynitride, silicon oxide, silicon oxynitride, tin oxide, tin oxynitride, chromia, chromium oxynitride, iron oxide, iron oxynitride, nickel oxide, nickel oxynitride, silver oxide, silver oxynitride, cobalt oxide, cobalt oxynitride, zinc oxide, zinc oxynitride, platinum oxide, platinum oxynitride, palladium oxide, palladium oxynitride, vanadium oxide, vanadium oxynitride, molybdenum oxide, molybdenum oxynitride, lead oxide, lead oxynitride, titanium oxide, titanium oxinitride, gold oxide, gold oxynitride, copper oxide, copper oxynitride, and a combination thereof.

7. The device of claim 5, wherein the nanostructure is selected from the group consisting of: $TiO_x$, x is 1 to 2; $TiO_{2-x}N_x$, x is 1 to 2; and a combination thereof.

8. The device of claim 7, wherein the nanostructure is a nanoparticle.

9. A method of detecting a concentration of a gas, comprising:
providing a conductometric porous silicon gas sensor including a n-type silicon substrate having a porous silicon layer, wherein a plurality of nanostructures are disposed on a portion of the porous silicon layer, wherein the conductometric porous silicon gas sensor is operative to transduce the presence of a gas into an impedance change when exposed to light, wherein the impedance change correlates to the gas concentration; wherein operation of the conductometric porous silicon gas sensor includes:
exposing the porous silicon layer to light;
introducing the gas to the sensor; and
measuring an impedance change in the sensor.

10. The method of claim 9, wherein the sensor includes a window or opening configured to allow light to illuminate the porous silicon layer.

11. The method of claim 9, wherein the light is selected from the group consisting of: visible light, ultraviolet light, and a combination thereof.

12. The method of claim 9, wherein the light is from a light source selected from the group consisting of: the sun, an artificial light source, and a combination thereof.

13. The method of claim 12, wherein the light source is part of the device.

14. The method of claim 9, further comprising: correlating the impedance change to the concentration of the gas.

15. The method of claim 14, wherein correlating includes computing a magnitude of the impedance change, computing the time over which the magnitude of the impedance change occurs, and computing a slope from the ratio of the magnitude of the impedance change and the time to determine the concentration of the gas.

16. A device, comprising:
a conductometric gas sensor including a n-type substrate having a porous layer, wherein a plurality of nanostructures are disposed on a portion of the porous layer, wherein the nanostructure provides a fractional coverage on the porous layer, wherein the sensor is configured to allow light to illuminate the porous silicon layer, wherein the conductometric gas sensor is operative to transduce the presence of a gas into an impedance change in the presence of light, wherein the impedance change correlates to the gas concentration.

17. The device of claim 16, wherein the sensor includes a window or an opening to allow light to illuminate the porous silicon layer.

18. The device of claim 16, wherein the light is from a light source selected from the group consisting of: the sun, an artificial light source, and a combination thereof.

19. The device of claim 18, wherein the light source is part of the device.

20. The device of claim 16, wherein the light is selected from the group consisting of: visible light, ultraviolet light, and a combination thereof.

21. The device of claim 16, wherein the n-type substrate is an extrinsic n-type semiconductor.

22. The device of claim 16, wherein the n-type substrate is selected from the group consisting of: silicon, GaP, InP, and CdTe.

23. The device of claim 16, wherein the n-type substrate is selected from the group consisting of: n- or $n^+$-type doped wafer and n- or $n^+$-type phosphorous doped wafer.

* * * * *